US011045235B2

(12) United States Patent
Johnson et al.

(10) Patent No.: US 11,045,235 B2
(45) Date of Patent: Jun. 29, 2021

(54) DENTAL OCCLUSION AND TENSION BAND TIES, SYSTEMS AND METHODS

(71) Applicant: REGENTS OF THE UNIVERSITY OF MINNESOTA, Minneapolis, MN (US)

(72) Inventors: Alan Wellington Johnson, Grand Forks, ND (US); Laura-Lee Farrell Brown, Maplewood, MN (US); Samuel C. Levine, Eden Prairie, MN (US); Christopher Rolfes, Saint Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 474 days.

(21) Appl. No.: 14/282,613

(22) Filed: May 20, 2014

(65) Prior Publication Data

US 2014/0343614 A1 Nov. 20, 2014

Related U.S. Application Data

(60) Provisional application No. 61/825,345, filed on May 20, 2013, provisional application No. 61/924,889, (Continued)

(51) Int. Cl.
*A61B 17/84* (2006.01)
*A61B 17/82* (2006.01)

(52) U.S. Cl.
CPC ............ *A61B 17/842* (2013.01); *A61B 17/82* (2013.01)

(58) Field of Classification Search
CPC .......... A61B 17/82; A61B 17/842; A61C 7/22; A61C 7/28; A61C 5/007
See application file for complete search history.

(56) References Cited

U.S. PATENT DOCUMENTS

| 3,022,557 A | 2/1962 | Logan |
| 4,813,869 A | 3/1989 | Gatewood |

(Continued)

FOREIGN PATENT DOCUMENTS

| CA | 2705492 | 5/2009 |
| EP | 0608592 A1 | 8/1994 |

(Continued)

OTHER PUBLICATIONS

Notification of Transmittal of the International Search Report and the Written Opinion of the International Searching Authority, or the Declaration, International Application No. PCT/US2014/038764, dated Sep. 25, 2014, 7 pages.

(Continued)

*Primary Examiner* — Samuel S Hanna
(74) *Attorney, Agent, or Firm* — Patterson Thuente Pedersen, PA

(57) ABSTRACT

Embodiments relate to devices, systems, kits and methods for achieving maxillo-mandibular fixation (MMF). In an embodiment, a system comprises a plurality of dental occlusion ties and/or tension band ties (referred to herein as "DO ties" and "TB ties," respectively). In another embodiment, a system or kit can comprise a plurality of one or both of DO ties and/or TB ties as well as a trimming tool, comfort caps or material, a lip/cheek retractor, and/or an instruction sheet. DO ties and TB ties can simplify the management of mandible fractures and maxilla fractures by helping re-establish precise dental occlusion for MMF.

7 Claims, 71 Drawing Sheets

Related U.S. Application Data filed on Jan. 8, 2014, provisional application No. 61/924,899, filed on Jan. 8, 2014, provisional application No. 61/924,906, filed on Jan. 8, 2014, provisional application No. 61/924,916, filed on Jan. 8, 2014, provisional application No. 61/924,920, filed on Jan. 8, 2014.

(56) References Cited

U.S. PATENT DOCUMENTS

| | | | |
|---|---|---|---|
| 4,968,248 A | 11/1990 | Divis | |
| 5,258,015 A * | 11/1993 | Li | A61B 17/0401 128/912 |
| 5,613,853 A | 3/1997 | Chasan | |
| 5,766,218 A | 6/1998 | Arnott | |
| 6,030,410 A | 2/2000 | Zurbrugg | |
| 6,050,998 A | 4/2000 | Fletcher | |
| 6,120,288 A | 9/2000 | Deslauriers | |
| 6,174,006 B1 * | 1/2001 | Burt | B65D 63/1081 24/16 PB |
| 6,257,884 B1 | 7/2001 | Chang | |
| 6,436,099 B1 * | 8/2002 | Drewry | A61B 17/7022 606/300 |
| 6,575,741 B2 | 6/2003 | Campbell | |
| 8,062,032 B2 | 11/2011 | Bulloch | |
| 8,414,581 B2 | 4/2013 | Shah et al. | |
| 2005/0282115 A1 | 12/2005 | Gedebou | |
| 2008/0262549 A1 | 10/2008 | Bennett et al. | |
| 2009/0148804 A1 | 6/2009 | Marcus | |
| 2010/0124727 A1 | 5/2010 | Shah | |
| 2011/0288551 A1 | 11/2011 | Walther | |
| 2012/0041441 A1 | 2/2012 | Bernstein | |
| 2013/0261625 A1 * | 10/2013 | Koch | A61B 17/1604 606/74 |

FOREIGN PATENT DOCUMENTS

| | | |
|---|---|---|
| JP | 2000/201941 A | 7/2000 |
| WO | WO 2011/063368 | 5/2011 |

OTHER PUBLICATIONS

Notification Concerning Transmittal of International Preliminary Report on Patentability, International Application No. PCT/US2014/038764, dated Dec. 3, 2015, 13 pages.

McGinn, Johnathan D., *Techniques of Maxillary-Mandibular Fixation*, Operative Techniques in Otolaryngology, vol. 19, No. 2, Jun. 2008, 6 pages.

DePuy Snythes, *RAPID IMF*, © 2015, 1 page.

Mercy-St John's Medical Research Institute, *PolyTrak: Intermaxillary Fixation System*, available at https://www.facebook.com/video/video.php?v=2396932435632, accessed on Jul. 1, 2013.

*Dental (Tooth) Anatomy*, Chapter 2, available at http://www.homesteadschools.com/dental/courses/Anatomy/Chapter2.htm, as of Sep. 8, 2015, 41 pages.

Wikimedia Commons, *File: Gingival Papillae.jpg*, last modified on May 10, 2015, 2 pages.

Engelstad, Mark E. et al., *Embrasure Wires for Intraoperative Maxillomandibular Fixation are Rapid and Effective*, Journal of Oral and Maxillofacial Surgery: Official Journal of the American Association of Oral and Maxillofacial Surgery, © 2011, pp. 120-124.

Canadian Examiner's Report, Canadian Application No. 2,912,211, dated Nov. 28, 2016, 4 pages.

Examination Report issued in Canadian Application No. 2,912,211, dated Sep. 27, 2017, 5 pages.

European Examination Report, Application No. 14 733 422.1, dated Nov. 20, 2018, 7 pages.

Examination Report, Canadian Application No. 2,912,211, dated Jul. 27, 2018, 51 pages.

Van der Walt, et al., Fixation of Mandible Fractures: A Simplified Method, vol. 65, No. 8, 358-63, Journal of South African Dental Association, Sep. 2010.

Office Action, U.S. Appl. No. 16/151,911, dated Oct. 16, 2020, 3 pages.

* cited by examiner

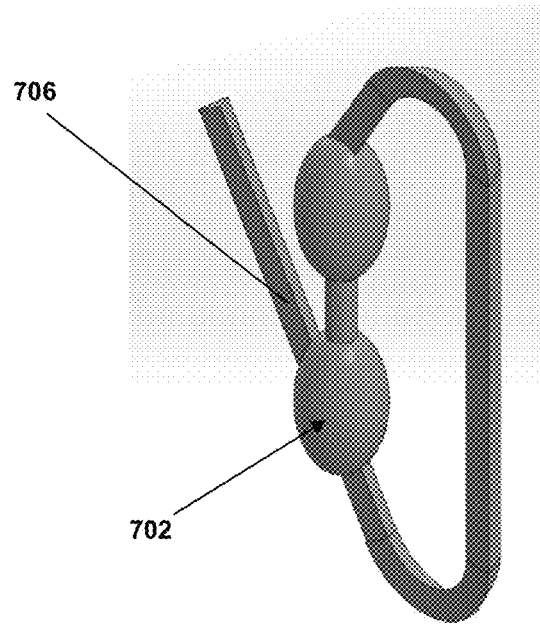
FIG. 32D
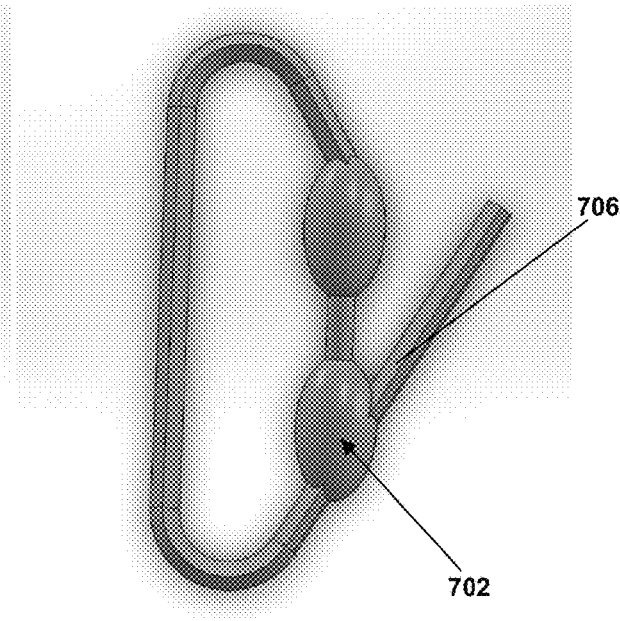
FIG. 32E
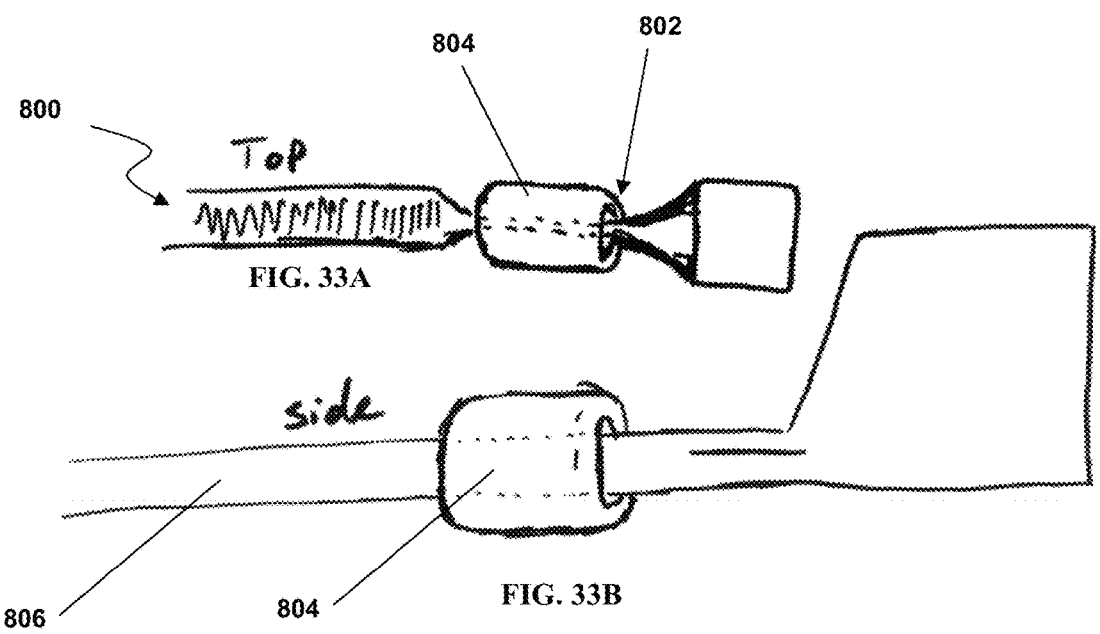
FIG. 33A
FIG. 33B

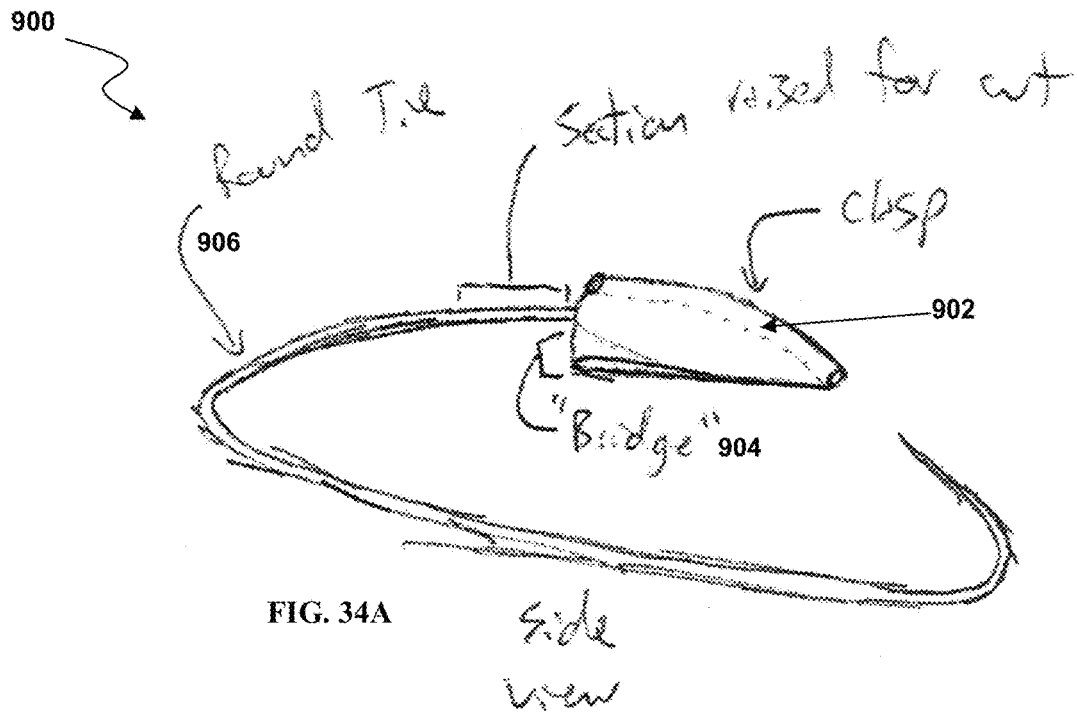
FIG. 34A
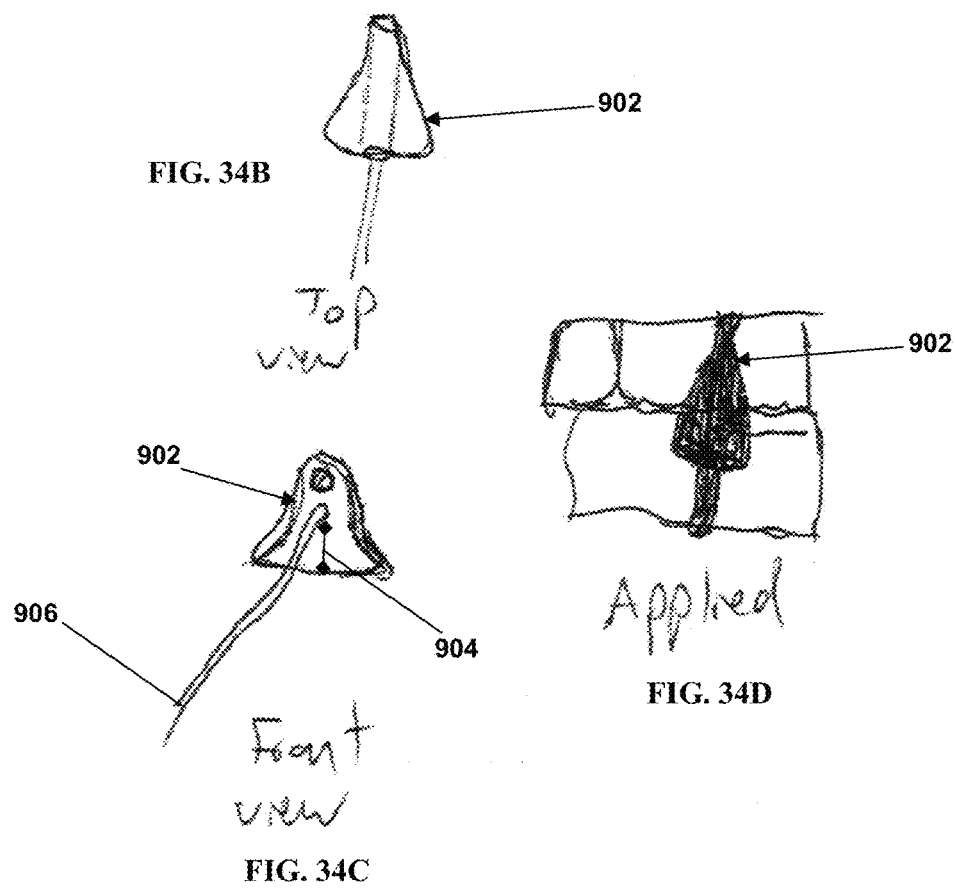
FIG. 34B
FIG. 34D
FIG. 34C

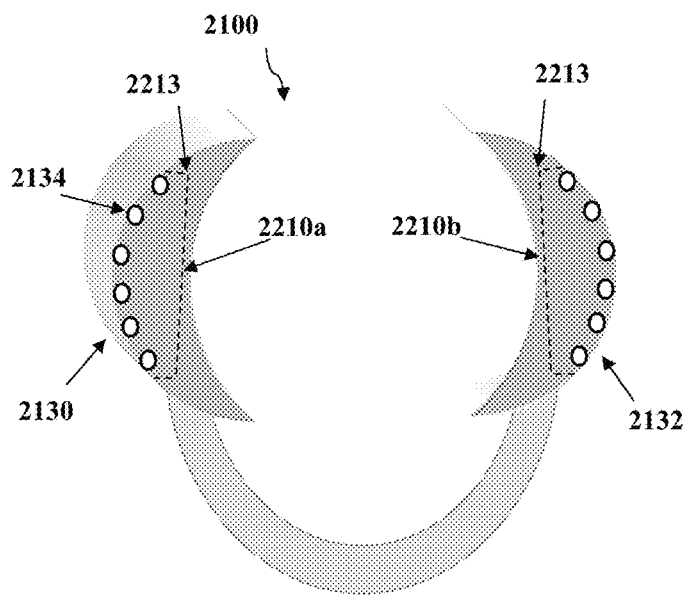
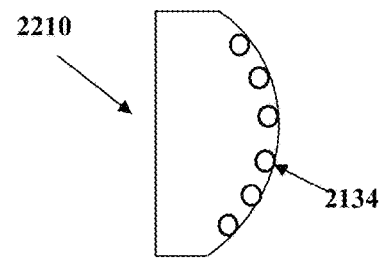
FIG. 51B
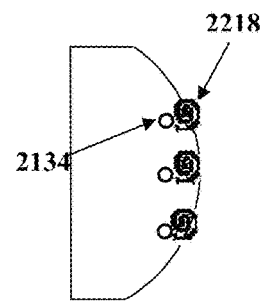
FIG. 51C
FIG. 51A
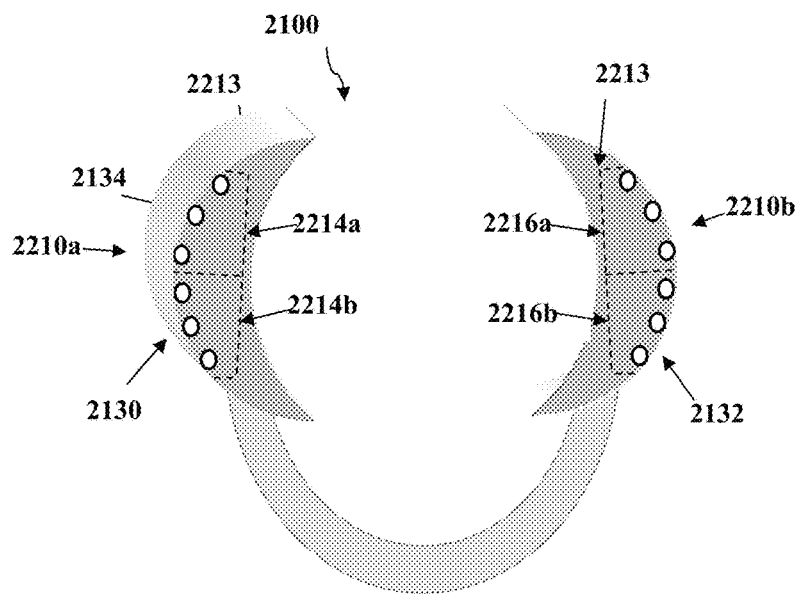
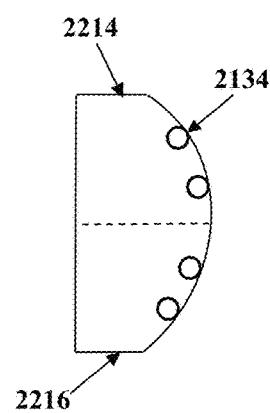
FIG. 52B
FIG. 52A

2100

2454
2452
2450
2102

2100

Human Pilot Sizing Experiment Data Compilation

| Tooth | Interdental space | Feeler Gauge (mm) | Feeler Gauge (inch) | Embrasure Sizer Number* | Embrasure Sizer Width (mm) |
|---|---|---|---|---|---|
| | 1 | NA | NA | NA | NA |
| | 2 | 0.076 | 0.003 | 11 | 1.13 |
| | 3 | 0.076 | 0.003 | 9 | 1.27 |
| | 4 | 0.076 | 0.003 | 9 | 1.27 |
| | 5 | 0.051 | 0.002 | 15 | 1.03 |
| | 6 | 0.063 | 0.0025 | 16 | 0.95 |
| | 7 | 0.076 | 0.003 | 14 | 1.07 |
| Midline | 8 | 0.076 | 0.003 | 17 | 0.88 |
| | 9 | 0.076 | 0.003 | 16 | 0.95 |
| | 10 | 0.076 | 0.003 | 15 | 1.03 |
| | 11 | 0.102 | 0.004 | 14 | 1.07 |
| | 12 | 0.076 | 0.003 | 9 | 1.27 |
| | 13 | 0.076 | 0.003 | 8 | 1.40 |
| | 14 | 0.063 | 0.0025 | 11 | 1.13 |
| | 15 | NA | NA | NA | NA |

FIG. 94A

DENTAL OCCLUSION AND TENSION BAND TIES, SYSTEMS AND METHODS

RELATED APPLICATIONS

The present application claims the benefit of U.S. Provisional Application No. 61/825,345 filed May 20, 2013, U.S. Provisional Application No. 61/924,889 filed Jan. 8, 2014, U.S. Provisional Application No. 61/924,899 filed Jan. 8, 2014, U.S. Provisional Application No. 61/924,906 filed Jan. 8, 2014, U.S. Provisional Application No. 61/924,916 filed Jan. 8, 2014, and U.S. Provisional Application No. 61/924,920 filed Jan. 8, 2014, each of which is incorporated herein by reference in its entirety.

TECHNICAL FIELD

The invention relates generally to maxillo-mandibular fixation (MMF) and more particularly to devices, systems, kits and methods for achieving MMF.

BACKGROUND

Mandible fractures are the second most common facial fractures behind nasal fractures. Like other fractures in the body, immobilization of the fractured segments is required for healing. For various fractures, immobilization can be achieved through casts, surgically-implanted hardware (plates, rods, screws), and other methods. Jaw fractures (mandible and maxilla) benefit from their unique connection to dentition. As the teeth are rigidly connected to the mandible and maxilla, jaw fractures can be immobilized by immobilizing the teeth in anatomic orientation. Placing the teeth in anatomic orientation (known as "dental occlusion") ensures that the cusps and the facets of the teeth fit appropriately as the fracture heals. The process of achieving this positioning is referred to as maxillo-mandibular fixation. The current leading technology to achieve maxillo-mandibular fixation (MMF) is "jaw wiring," commonly referred to as "arch bars" by facial trauma surgeons. Referring to FIG. 1A, arch bars have been a standard of care for decades and invariably require application under general anesthetic for patient tolerance. Alternative variations of jaw wiring include Ivy loops (FIG. 1B), Ernst ligatures (FIG. 1C), and screw fixation (FIG. 1D) approaches—all of which have achieved minimal adoption because of significant drawbacks. Wire-based MMF techniques commonly use 24 gauge stainless steel wires. The alternative wiring techniques (i.e., Ivy loops, Ernst ligatures) offer speed of application, but still require considerable manipulation by the surgeon in an operating room to apply them to the patient. The screw fixation techniques pose risks to tooth roots and to the gingiva (gums) and have also shown very limited clinician adoption.

All of these techniques, including the more widely adopted arch bars, induce considerable trauma to the gums and mucosa of the patient, causing considerable pain. Also, as these techniques are applied in the operating room under general anesthesia, they incur considerable cost due to the time-consuming nature of these techniques. Further, the metal wires used in these techniques can be rigid and pointed, placing the surgical team at risk for sharps injuries.

Thus, there is a need for improved devices, systems and methods for achieving maxillo-mandibular fixation in a manner that can minimize patient discomfort, avoid the intensive labor and financial demands of such approaches, and provide a safer application for the surgical team.

SUMMARY

Embodiments relate to devices, systems, kits and methods for achieving maxillo-mandibular fixation (MMF). In an embodiment, a system comprises a plurality of dental occlusion ties and/or tension band ties (referred to herein as "DO ties" and "TB ties," respectively). In another embodiment, a system or kit can comprise a plurality of one or both of DO ties and/or TB ties as well as a trimming tool, comfort caps or material, a lip/cheek retractor, and/or an instruction sheet. DO ties and TB ties can simplify the management of mandible fractures and maxilla fractures by helping re-establish precise dental occlusion for MMF. DO ties and TB ties can be used as the sole treatment for mandible fractures or can be used in combination with other techniques such as "internal fixation" (plating the fracture through an incision). In embodiments, methods of use and application require limited tissue disruption, application time, and sharps risk.

In embodiments, DO ties function to reinforce dental occlusion. In a common application, DO ties reinforce closure of the jaw to put the upper dentition in contact with the lower dentition.

In embodiments, TB ties function to hold a fracture in reduction. By spanning the site of a fracture and securing teeth that are rigidly fixed to either side of the fracture, TB ties can provide a force that inhibits the distraction or movement of bony segments at the site of fracture.

DO ties can be applied to any interdental space, such as the apical embrasure. TB ties can be applied around or between one or more teeth, dental implants, or equivalents to provide a number of functions, including but not limited to: support, corrective forces, temporary compression and long-term stabilization. In various embodiments, DO and TB ties can share the same interdental space or otherwise oppose, abut, interact or even interconnect with one another. DO ties and TB ties can be identical or different from one another, for example varying by a material, size, configuration, or other characteristic, though each is sufficiently flexible and/or configured for ease of application and subsequent removal. In other embodiments, DO ties can be offered in a range of materials, sizes or configurations, as can TB ties. Embodiments of the devices, systems and methods disclosed herein thereby can offer versatility in the management of jaw fractures, as any number of combinations of DO and TB ties can be applied to fixate the dentition.

The above summary is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 32D is a perspective view of the dental occlusion or tension band tie of FIG. 32C, according to an embodiment.

FIG. 32E is a side view of the dental occlusion or tension band tie of FIG. 32C, according to an embodiment.

FIG. 33A is a top view of a dental occlusion or tension band tie having a clasp with a floating bridge, according to an embodiment.

FIG. 33B is a side view of the dental occlusion or tension band tie of FIG. 33A, according to an embodiment.

FIG. 34A is a side view of a dental occlusion or tension band tie having a clasp with a raised entry point, according to an embodiment.

FIG. 34B is a top view of the dental occlusion or tension band tie of FIG. 34A, according to an embodiment.

FIG. 34C is a front view of the dental occlusion or tension band tie of FIG. 34A, according to an embodiment.

FIG. 34D is a side view of the dental occlusion or tension band tie of FIG. 34A in a locked position, according to an embodiment.

FIG. 51A depicts a front view of a cheek refractor and tie organizer, according to an embodiment.

FIG. 51B depicts a front view of a tie organizer, according to an embodiment.

FIG. 51C depicts a front view of a tie organizer, according to an embodiment.

FIG. 52A depicts a front view of a cheek retractor and tie organizer, according to an embodiment.

FIG. 52B depicts a front view of a tie organizer, according to an embodiment.

FIGS. 94A and 94B are composite images of data relating embrasure size to depth of insertion of a probe of the sizing device, according to an embodiment.

Figure 1:
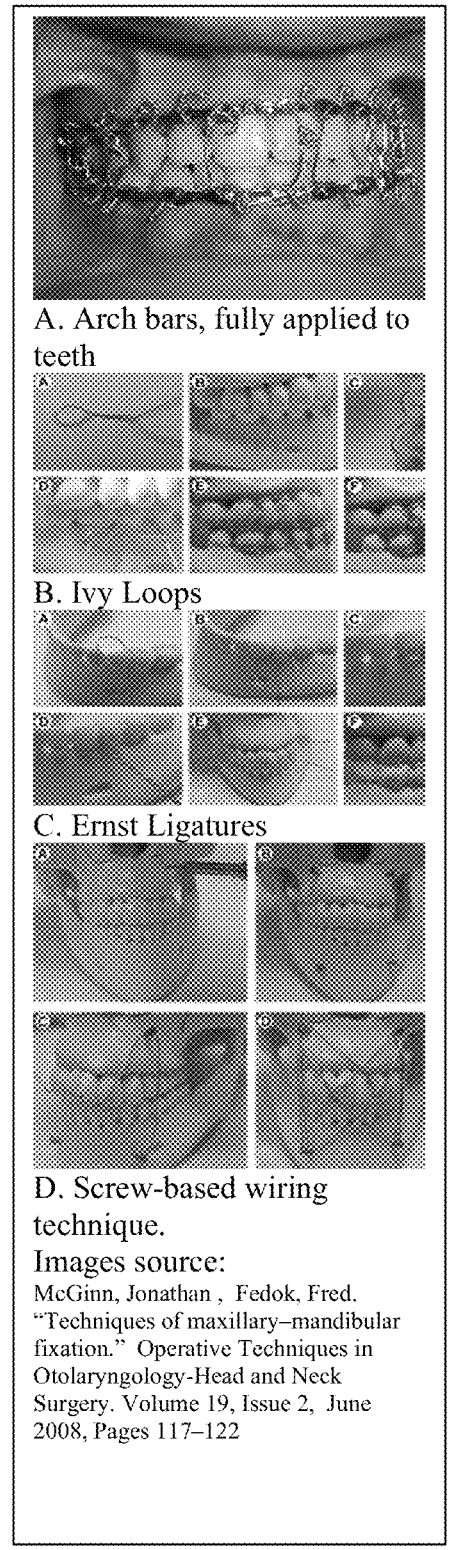
FIGS. 1A-1D depict conventional approaches to achieving maxillo-mandibular fixation.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Figure 2:
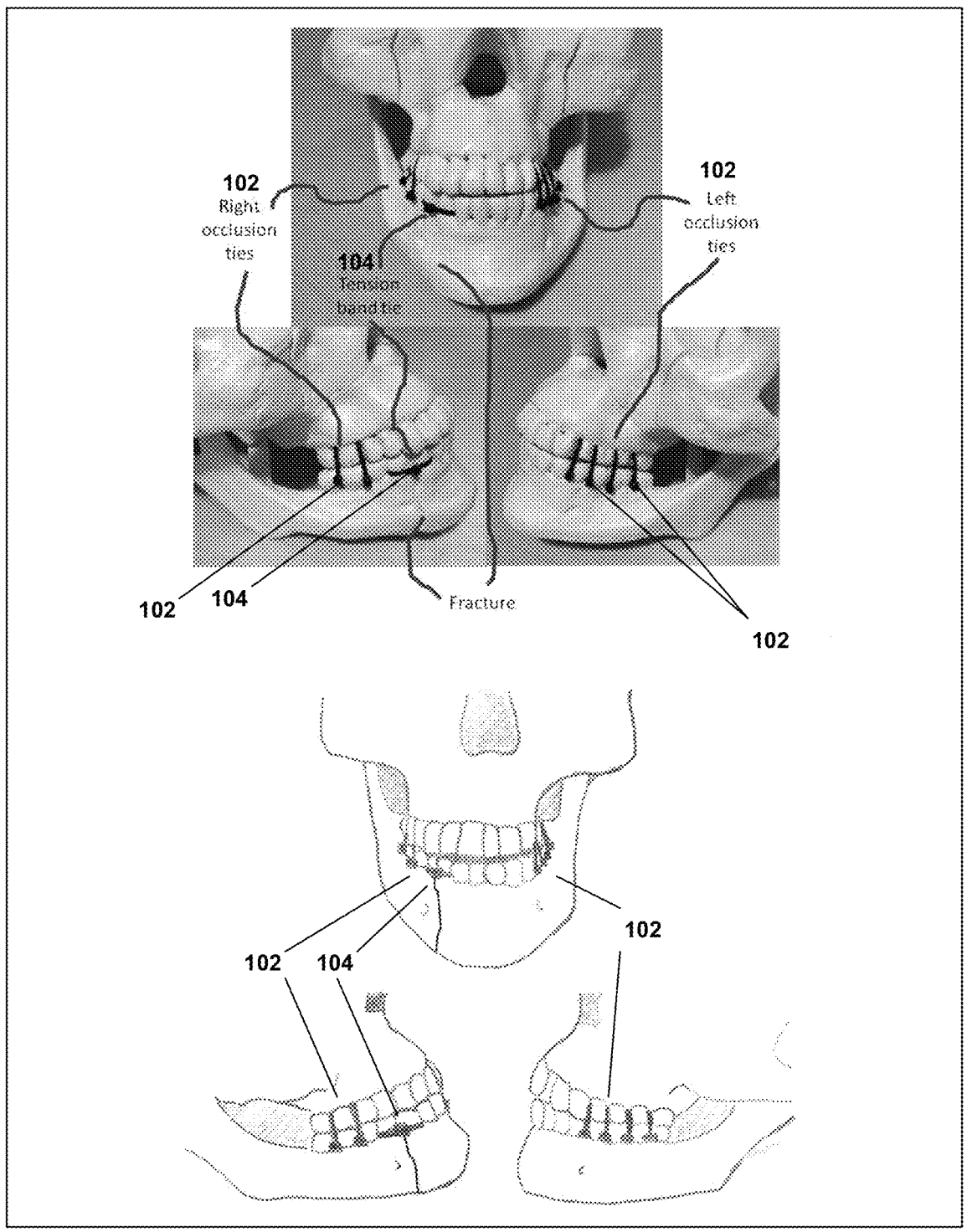
FIG. 2 depicts dental occlusion ties applied to fixate the mandible (lower jaw) to the maxilla (upper jaw) and a tension band tie applied to immobilize a fracture site, according to an embodiment.

An embodiment of dental occlusion ("DO") and tension band ("TB") ties as well as an application of a system and method of applying DO and TB ties is depicted in FIG. 2. FIG. 2 depicts DO ties 102 achieving maxillo-mandibular fixation as well as a TB tie 104 providing stability for a mandible fracture. The combination of forces applied by such a DO tie 102, TB tie 104 and/or system can establish a construct that is rigid enough to foster adequate healing in the fracture bed by minimizing movement at the site. For example, a system comprising a plurality of ties 102 and/or 104 arranged to provide an optimal or desired combination of forces for any particular patient or purpose. In an embodiment, such a system comprises a plurality of ties 102 and/or 104 applied in adjacent interdental spaces and/or arranged on the same or opposing sides of jaw such that sufficient combinations of forces are acting on the teeth and jaw to obtain MMF while maintaining the ties 102 and/or 104 in place. The particular arrangement of the ties for any particular patient can vary according to injury or reason for application, dental characteristics including number, presence and/or relative spacing of teeth, level of occlusion necessary or obtainable between the upper and lower jaws, and other factors. For example, a user can adapt the ties 102 and/or 104 to counteract the expected forces encountered in or necessary to aid in the healing of jaw fractures. The ties 102 and 104 can be applied for both fractures that occur within the tooth-bearing segment of the mandible or maxilla and for those fractures outside the tooth-bearing segments. For example, FIG. 2 depicts a fracture in the tooth-bearing segment of the right lower mandible. Thus, a physician or other clinician can customize an application of ties 102/104 and/or a system thereof in any particular use.

Figure 3:
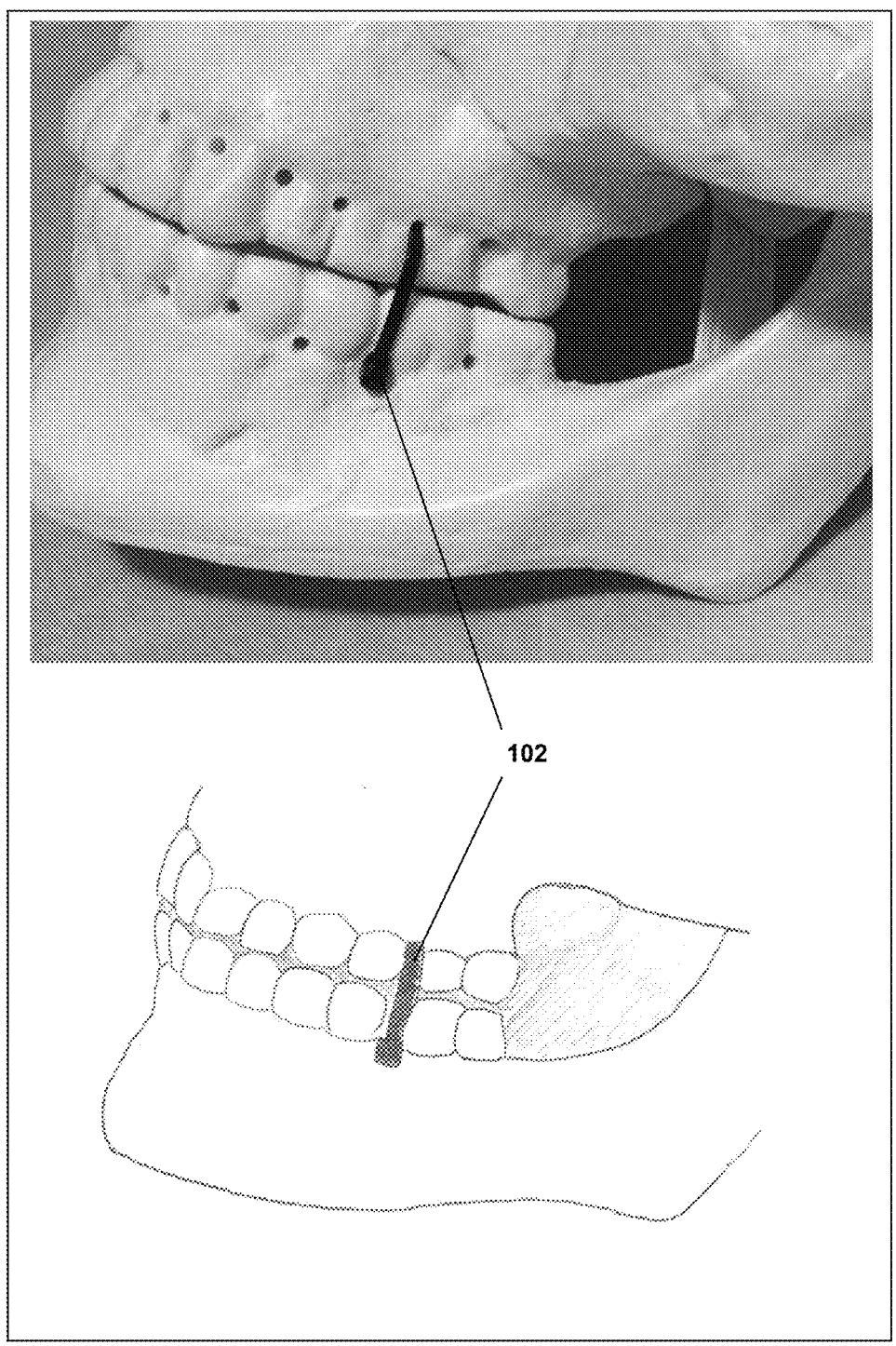
FIG. 3 depicts a dental occlusion tie applied between the upper and lower dentition, according to an embodiment.
Figure 4:
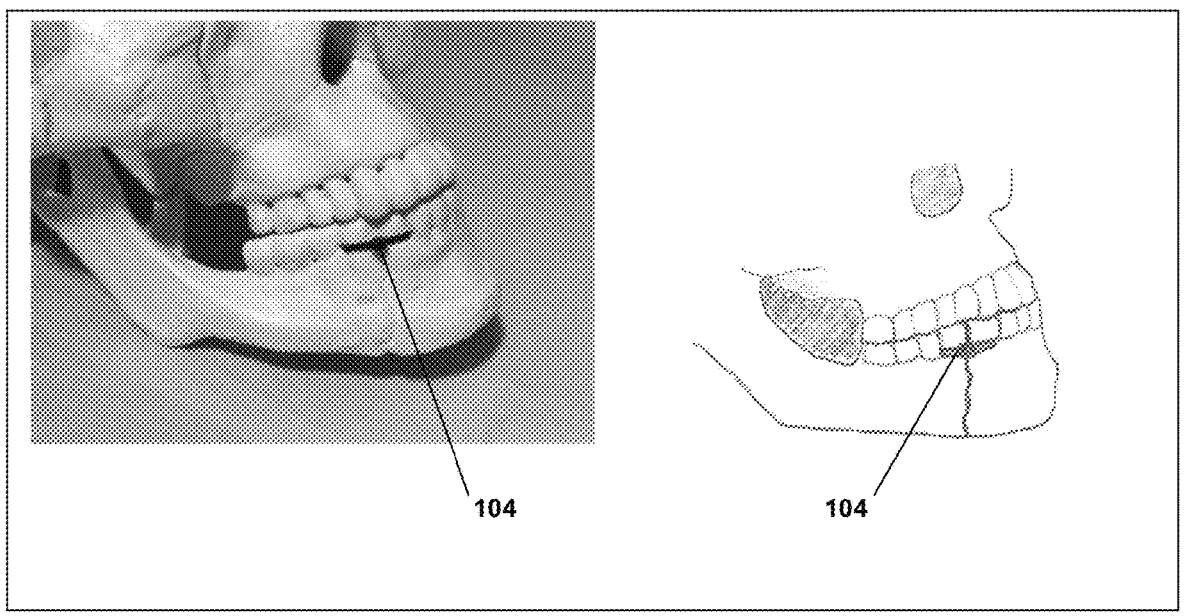
FIG. 4 depicts a tension band tie applied to the lower dentition, according to an embodiment.
Figure 6:
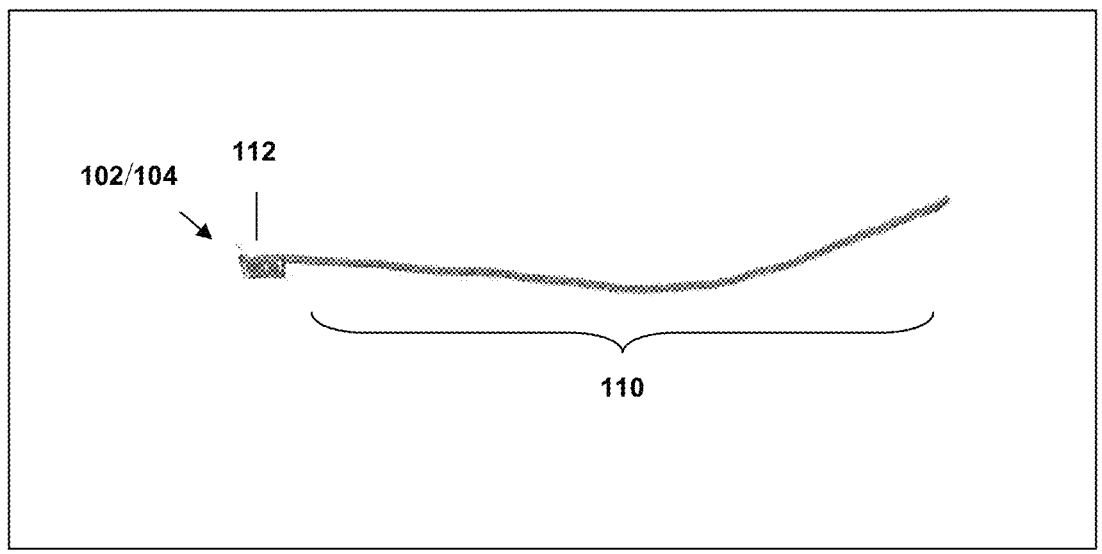
FIG. 6 depicts an example single dental occlusion tie or tension band tie component parts, according to an embodiment.
Figure 7:
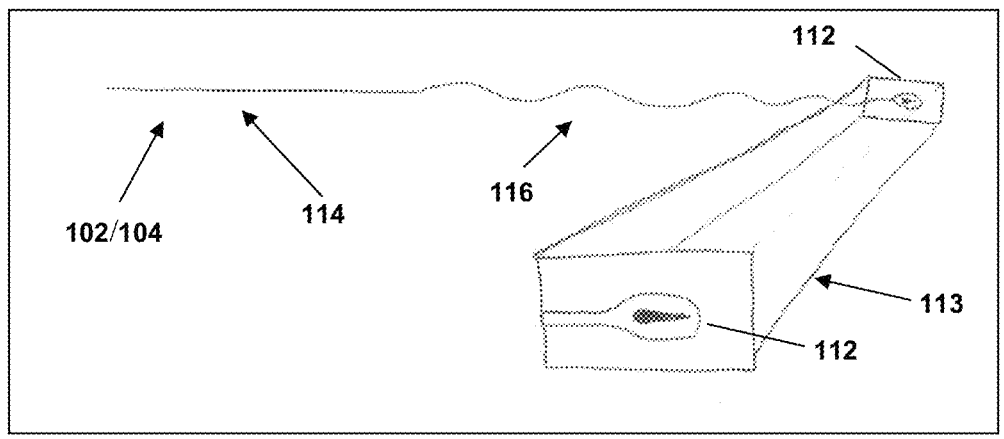
FIG. 7 depicts an example where the clasp mechanism includes a tapered slot to pinch the thread segment of the tie to create a secure loop, according to an embodiment.
Figure 8:
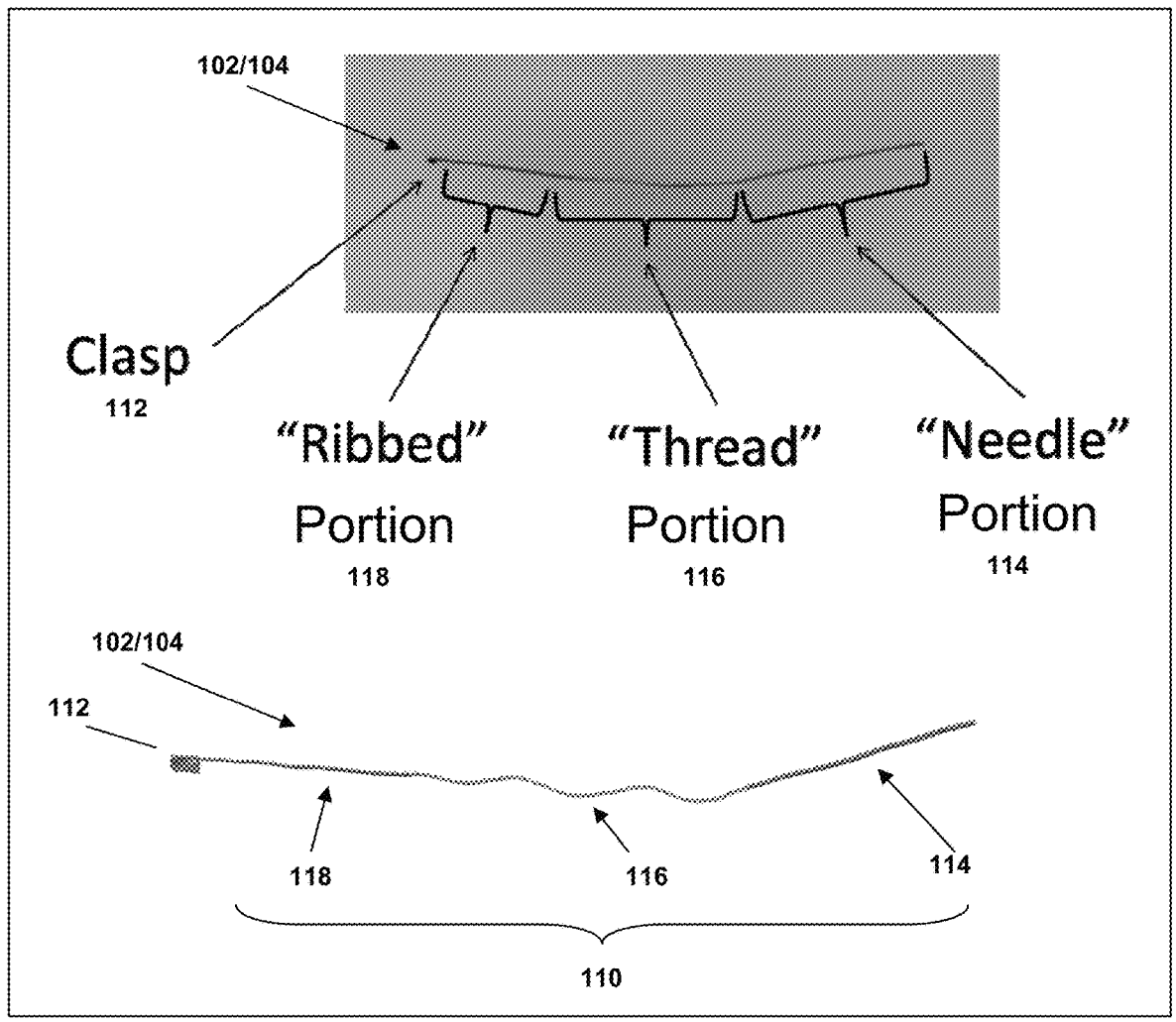
FIG. 8 depicts an example single dental occlusion tie or tension band tie with multiple component parts, according to an embodiment.
Figure 9:
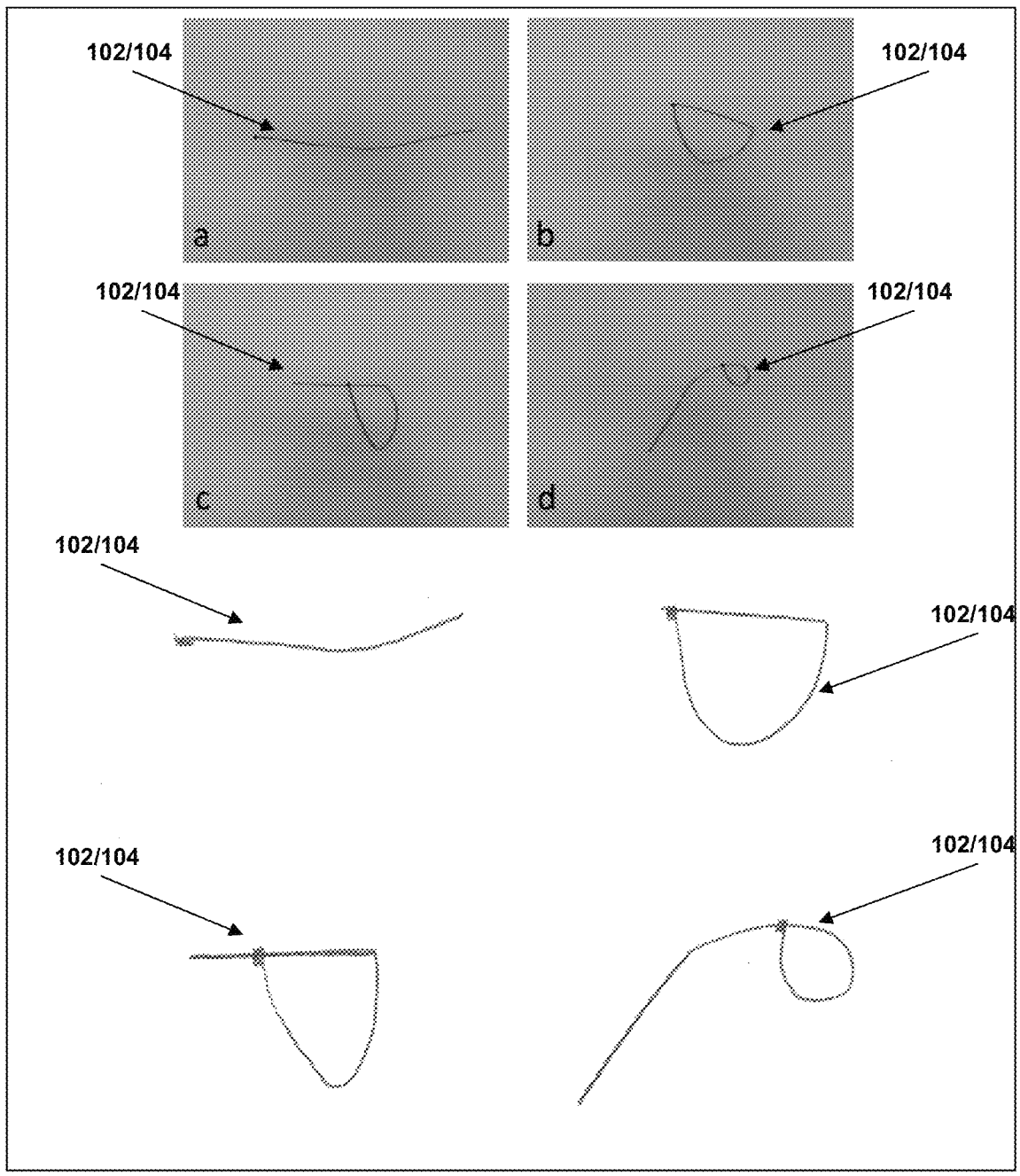
FIG. 9 depicts a dental occlusion or tension band tie function, according to an embodiment.

Embodiments of DO ties 102 and TB ties 104, in a single device form, are pictured in FIG. 3 (DO tie 102), FIG. 4 (TB tie 104) and FIG. 6, as well as FIGS. 7-12, which will be referred to generally herein throughout unless otherwise noted. In an embodiment, the two devices 102 and 104 generally comprise an elongate body 110 and a clasp 112 (refer, for example, to FIG. 6). In another embodiment, body 110 can be considered to comprise a needle portion 114 and a thread portion 116 and with a clasp portion 112 to engage the thread portion 116 (refer, for example, to FIG. 7). In another embodiment, body 110 can comprise an insertion or needle portion 114, a thread portion 116 and a ribbed portion 118. Other combinations of these and other portions can be arranged to form either or both of devices 102 and 104 in other embodiments.

Body 110 can have a unitary construction in an embodiment such that needle portion 114, thread portion 116 and ribbed portion 118 are formed of a single piece of material, or one or more of the portions 114, 116 and/or 118 can be separately formed of the same or a different material and coupled with the other portions. Similarly, in embodiments, clasp 112 can be of unitary construction with one, some or all of portions 114, 116 and/or 118, or clasp 112 can be separately formed and coupled therewith. Couplings between one or more of clasp 112 and portions 114, 116 and 118 can be removable or fixed, and can vary in various embodiments of DO ties 102 and/or TB ties 104.

In embodiments, needle portion 114 can be substantially linear, or can comprise a plurality of angled segments having a finite number of inflection points. Alternatively, needle portion 114 can comprise a continuous curve or any combination of curvilinear or linear segments. In general, needle portion 114 is sufficiently flexible so as to facilitate insertion and movement within the limited oral cavity, though in embodiments needle portion 114 or a segment thereof can be more or less rigid or flexible.

Needle portion 114 comprises a geometry and material enabling it to traverse the interdental space and enter and exit the oral cavity at least for ease of placement, manipulation and/or application of devices 102 and 104. For example, needle portion 114 typically comprises a cross-sectional shape and area suitable to fit between adjacent teeth. In embodiments, needle portion 114, as well as other portions of DO and TB ties 102 and 104 themselves, can be provided in different sizes or configurations to accommodate, e.g., patients of different ages; teeth and interdental spaces of different sizes, alignments and configurations; and other factors related to a patient, medical condition or characteristic, or some other characteristic. For example, in embodiments, needle portion and/or other portions of DO tie 102 and/or TB tie 104 has a cross-sectional diameter in a range of about 0.5 mm to about 3.0 mm, for example about 0.75 mm. In another example, in embodiments, needle portion and/or other portions of DO tie 102 and/or TB tie 104 has a cross-sectional diameter in a range of about 0.25 mm to about 1.0 mm, for example about 0.5 mm. Needle portion 114 also generally comprises a length long enough to facilitate manual handling on both sides of the interdental space. In embodiments, a length of needle portion 114 is generally in a range of about 25 mm to about 150 mm, for example about 100 mm in one embodiment. In another embodiment, a length of needle portion 114 is generally in a range of about 15 mm to about 30 mm, for example about 22 mm. An overall length of DO tie 102 and/or TB tie 104 can be in a range of about 150 mm to about 350 mm in embodiments, for example about 250 mm in one embodiment. In general, needle portion 114 comprises a minimally abrasive surface to minimize trauma to the patient's tissues during application. The leading tip of needle portion 114 could include a blunt, tapered, or rounded tip (FIG. 12) to minimize risk of accidental puncture ("needle stick") injury in embodiments. In embodiment, needle portion 114 comprises at least one of a metal, alloy, ceramic, plastic, polymer or other suitable compound or combination thereof with sufficient strength to sustain the forces (e.g., twisting, sheer, and longitudinal) required to traverse an interdental space. For example, an embodiment can comprise a polymer-coated metal needle portion 114. In embodiments, needle portion 114 can be malleable or rigid. The other portions 112, 116, 118 as well as DO tie 102 and TB tie 104 also can comprise one or more of these or other suitable materials in embodiments.

Thread portion 116 can be of the same or a different material as needle portion 114 in embodiments. One primary function of thread portion 116 is to link needle portion 114 to clasp 112 such that the device, DO tie 102 and/or TB tie 104, can traverse one or more interdental spaces. Thread portion 116 can have a cross-sectional area small enough to traverse an interdental space, for example having a diameter in a range of about 0.3 mm to about 3.0 mm, such as about 0.75 mm in one embodiment. In another example, thread portion 116 can have a diameter in a range of about 0.25 mm to about 1.0 mm, such as about 0.6 mm in one embodiment. Further, thread portion 116 has a sufficient length and flexibility to enable needle portion 114 to turn and traverse a second interdental space without displacing the device 102 or 104 from the first interdental space. For example, a length of thread portion 116 can be in a range of about 40 mm to about 140 mm in embodiments, such as about 80 mm in one embodiment. In another example, a length of thread portion 116 can be in a range of about 100 mm to about 250 mm in embodiments, such as about 180 mm in one embodiment. In another example, a length of thread portion 116 can be in a range of about 80 mm to 200 mm, such as about 100 mm in one embodiment. Thread portion 116 can comprise the same or different materials as needle portion 114 as discussed herein above, though in general thread portion 116 comprises a material or materials and configuration which provide sufficient strength to sustain the forces (e.g., tension, abrasion, friction, torsion, and sheer) required to traverse an interdental space and maintain a connection between the proximal and distal components of the device 102 or 104. For example, in embodiments thread portion 116 comprises a metal, alloy, ceramic, plastic, polymer such as nylon, a natural material such as silk, or other suitable compound or combination thereof.

Ribbed portion 118 comprises one or more elements along some or all of its longitudinal length to provide a secure engagement with clasp 112 when inserted therein. These elements can comprise but are not limited to one or more ribbed serrations, "saw-tooth" serrations, perforations, holes, apertures, beads, and surface irregularities, among other suitable elements appreciated by those skilled in the art. In other embodiments, ribbed portion 118 can be substantially or entirely smooth, for example in an embodiment in which clasp 112 is crimped or pinched on or around ribbed portion 118 or some other configuration. In an embodiment, ribbed portion 118 can have a cross-sectional diameter in a range of about 0.5 mm to about 3.0 mm, such as about 0.75 mm in one embodiment. In another embodiment, ribbed portion 118 can have a cross-sectional diameter in a range of about 0.25 mm to about 1.0 mm, such as about 0.70 mm in one embodiment. Ribbed portion 118 can have a length of about 30 mm to about 80 mm in embodiments, such as about 50 mm in one embodiment. In another embodiment, ribbed portion 118 can have a length of about 20 mm to about 80 mm.

Similar to the needle and thread portions 114 and 116, ribbed portion 118 can comprise one or more of a metal, alloy, ceramic, plastic, polymer such as nylon, a natural material such as silk, or other suitable compound or combination thereof with sufficient strength to sustain the forces (e.g., tension, abrasion, friction, torsion, deflection, and sheer) required to traverse an interdental space and maintain a connection between the proximal and distal components of the device 102 or 104. Further, ribbed portion 118 is configured to maintain tensile force while also maintaining a wedged, pinched, or constrained position between teeth and within clasp 112 in use.

A cross-sectional profile of a DO tie 102 can vary in embodiments from that of a TB tie 104, for example in the ribbed portion 118. For example, a cross-section of a DO tie 102 at ribbed portion 118 can comprise an approximate or general isosceles triangle to effectively wedge between two adjacent teeth in the apical embrasure 130 (refer, for example, to FIG. 5). Other cross-sectional shapes and configurations can be used in other embodiments. An additional example of a cross-sectional segment could be a substantially "V" or "U" shape to wedge between adjacent teeth while minimally disrupting the gingival papilla 132 (i.e., the gum tissue between the teeth), or some other shape suitable for maintaining sufficient force to keep device 102 or 104 in position while obtaining MMF and/or acting on a jaw or other fracture. The cross-sectional shape of the ribbed portion 118 of the TB ties 104 could be generally triangular, rectangular, round, curvilinear (i.e., crescent-shaped) or some other suitable shape or combination thereof, in various embodiments. In a kit comprising a plurality of DO ties 102 and/or TB ties 104, an assortment of devices 102 and/or 104 having various sizes, configurations, cross-sectional shapes, materials and other characteristics can be provided such that a medical professional could select the one or ones most suitable for any particular patient and his or her anatomy. For example, different cross-sectional shapes could be utilized to interact with the different interdental geometries of different teeth (e.g., molars, incisors, canines, etc).

In another example, the DO and TB ties 102 and 104 do not include a ribbed portion 118. Instead, in this embodiment the clasp 112 includes a pinching mechanism 113 depicted in one embodiment in FIG. 7, though other mechanisms and configurations can be implemented in other embodiments. This pinching mechanism 113 can comprise a material (e.g., stainless steel, nitinol, nylon, etc) that is stronger and firmer than the thread portion 116 that is placed there. The pinching mechanism 113 also could comprise a narrow slot or stellate aperture that secures the thread portion 116 as depicted.

Figure 11:
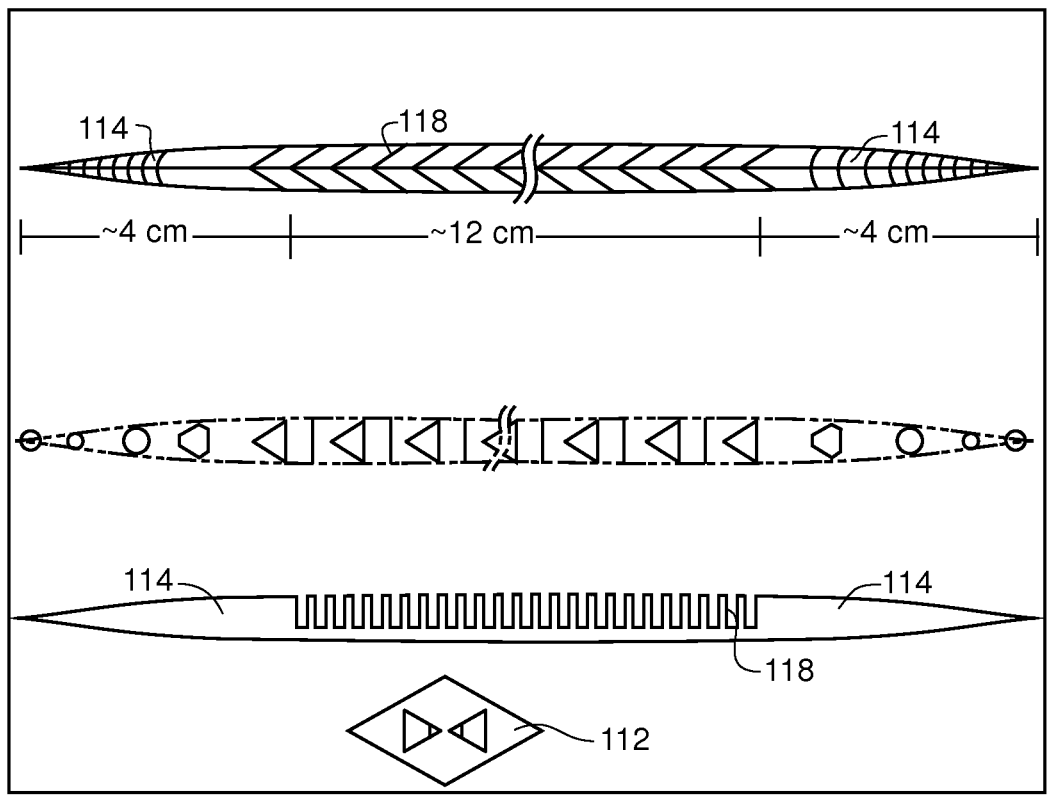
FIG. 11 depicts a dental occlusion tie with a detached clasp including a number of cross-sectional geometries, according to embodiments.
Figure 19:
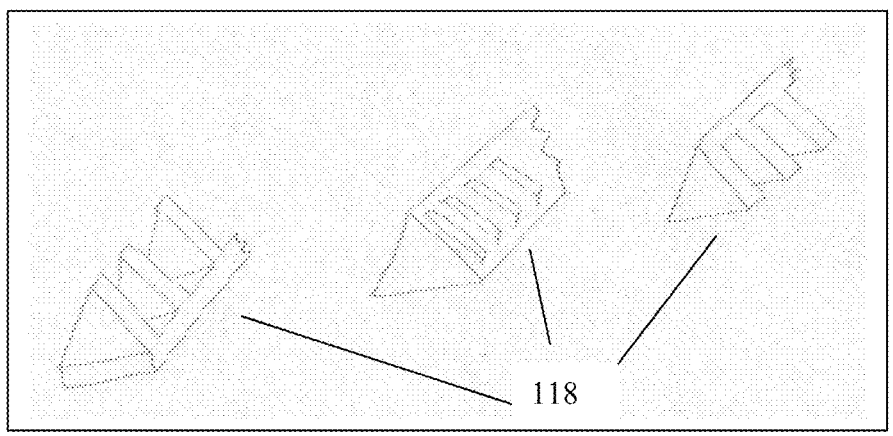
FIG. 19 depicts example ribbed portions, according to an embodiment.

Referring in particular to FIG. 11, clasp 112 can be a separate device configured for use with needle, thread and ribbed portions 114, 116 and 118, or clasp 112 can be formed continuous with one or more of these portions, as previously mentioned. In embodiments, clasp 112 is integrally formed with any of needle, thread or ribbed portions 114, 116 and 118. Clasp 112 can engage the proximal segments of ribbed portion 118 to secure the device 102 or 104 through various methods including but not limited to a cable tie clasp (for example, interfacing with a serrated, irregular, "saw-toothed," or tabulated ribbed segment—FIG. 19 depicts a few illustrative and non-limiting examples), a pleat (for example, to wrap a proximal segment around), a crimping/pinching mechanism (to squeeze the ribbed segment causing sufficient friction to hold), an adhesive interface (example: surface polymer adhesive, hooks and loops), and/or a magnetic attraction, among others. The tie can include two or more linked needle segments and two or more ribbed segments (refer, for example, to FIGS. 11 and 14). FIG. 11 also includes example cross-sections, dimensions and other configurations, which can vary in these and other embodiments but are included here by way of example.

Figure 20:
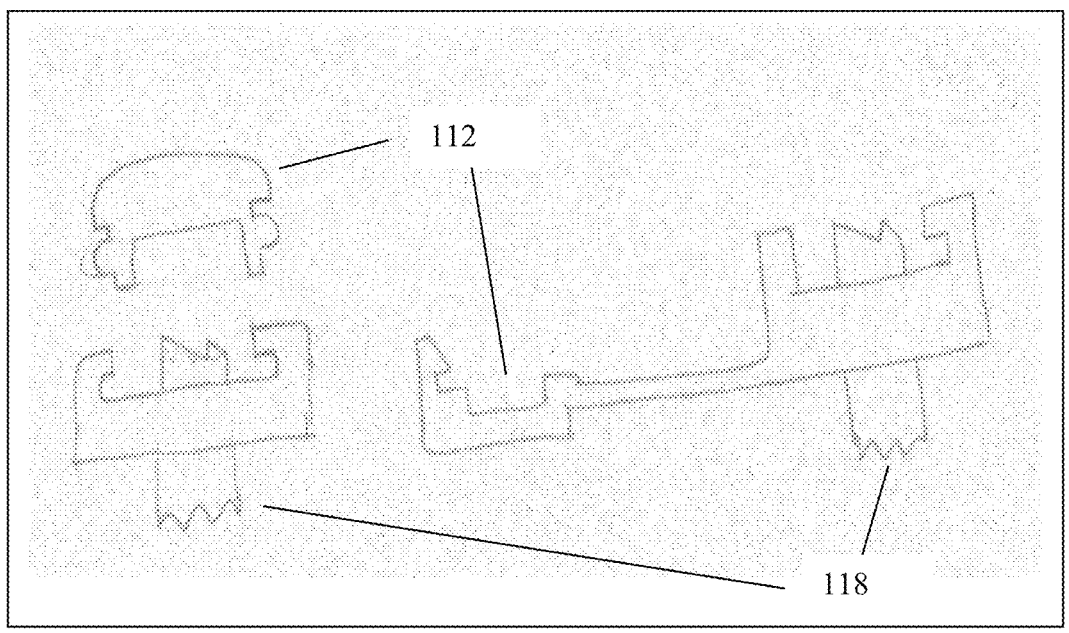
FIG. 20 depicts example cover portions, according to embodiments.

A cover portion 120 also can be provided in some embodiments, though it can be omitted or optional in other embodiments. Cover portion 120 can comprise a separate portion, or a portion formed continuous with the other portions discussed above, as is depicted in FIGS. 10 and 20. A purpose of cover portion 120 can be to minimize the irritation or trauma to the mobile tissues in the mouth that interact with the device 102 or 104. Cover 120 can comprise a smooth geometry or soft material, such as a plastic, polymer, composite or other suitable material, such that the interface of the patient's tissues would be less irritated than if in direct contact with the DO tie 102, TB tie 104 or any of their components, particularly the clasp 112 or any residual of the needle, thread, or ribbed portions 114, 116, 118. In embodiments, cover 120 can be pliable or flexible to improve patient comfort and/or placement and positioning of cover 120 relative to clasp 112. In yet another embodiment, cover 120 can comprise a wax or other material provided with tie 102 or 104, such as in a kit.

Figure 5:
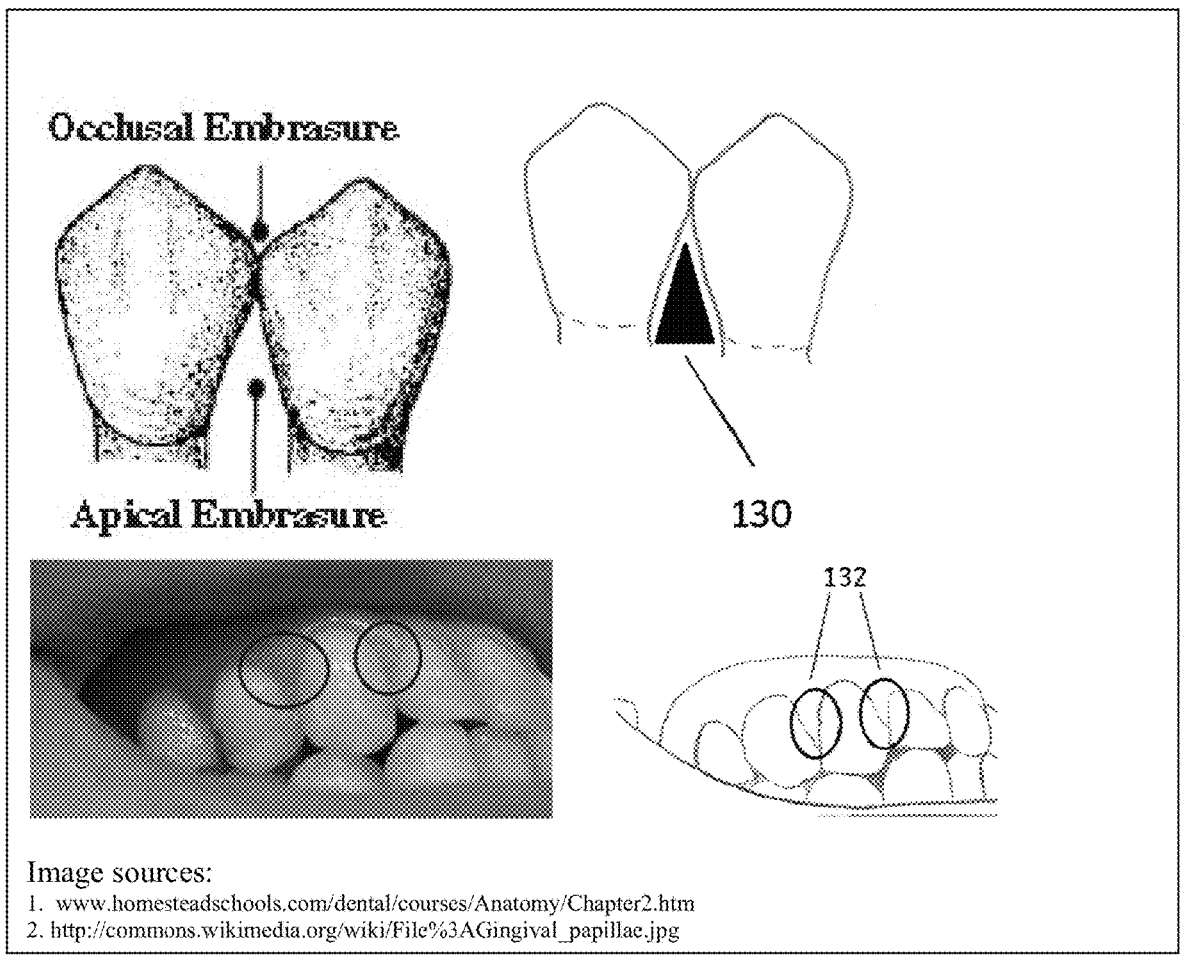
FIG. 5 depicts the apical embrasure, an intended site of dental occlusion tie and tension band tie application, according to an embodiment.
Figure 10:
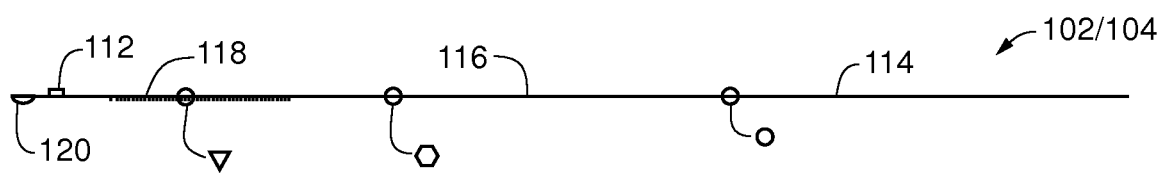
FIG. 10 depicts a single dental occlusion tie, according to an embodiment.
Figure 12A:
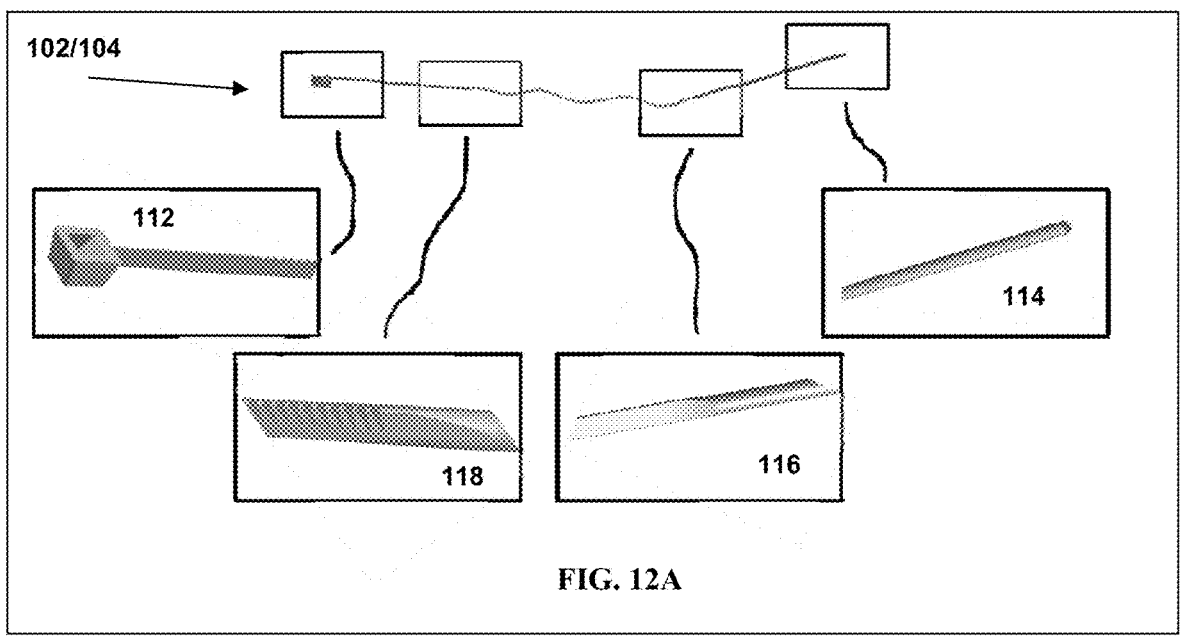
FIG. 12A depicts example cross-sectional geometries of portions of one embodiment.
Figure 14:
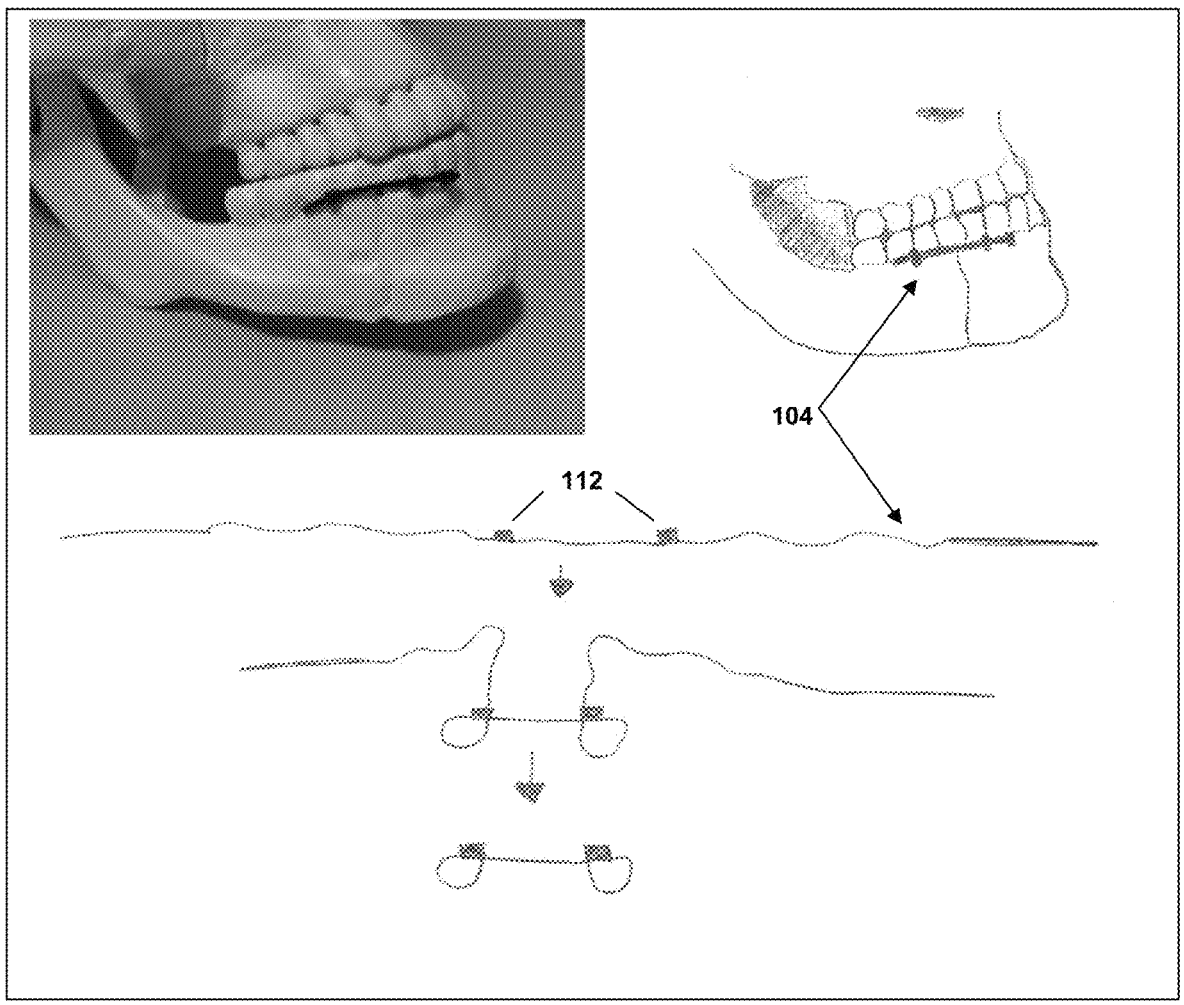
FIG. 14 depicts a specialized tension band tie designed to secure to teeth that are not immediately adjacent to a fracture site, according to an embodiment.

In one embodiment of use of the TB tie 104 and/or the DO tie 102, and referring also to FIG. 14, the device 102 or 104 can be applied to the dentition of a patient by creating a loop. The loop can be secured by passing the needle and thread portions 114 and 116 through the clasp 112 until the ribbed segment 118 engages the clasp 112. Once the clasp 112 engages with the ribbed segment 118, the loop is secure. This process is depicted, for example, in FIG. 9. The apical embrasure 130, shown in FIG. 5, is the intended site of application of the DO ties 102 and possible site of application for the TB ties 104. FIG. 3 depicts how a DO tie 102 is threaded in a vertical plane though the triangular embrasure 130 between teeth of both the mandible and maxilla to secure the dentition in occlusion. FIG. 4 depicts how a TB tie 104 is threaded in a horizontal plane between the interdental spaces adjacent to a mandibular fracture with the intent of preventing fracture site distraction. FIGS. 10, 11, and 12 depict three example configurations of dental occlusion ties 102 with geometries that are optimized for application within the apical embrasures 130 to maximize the potential for a secure wedge between adjacent teeth. Other relative arrangements and configurations can be used in other embodiments, for example as desired by a clinician for any particular patient to receive treatment.

Figure 12B:
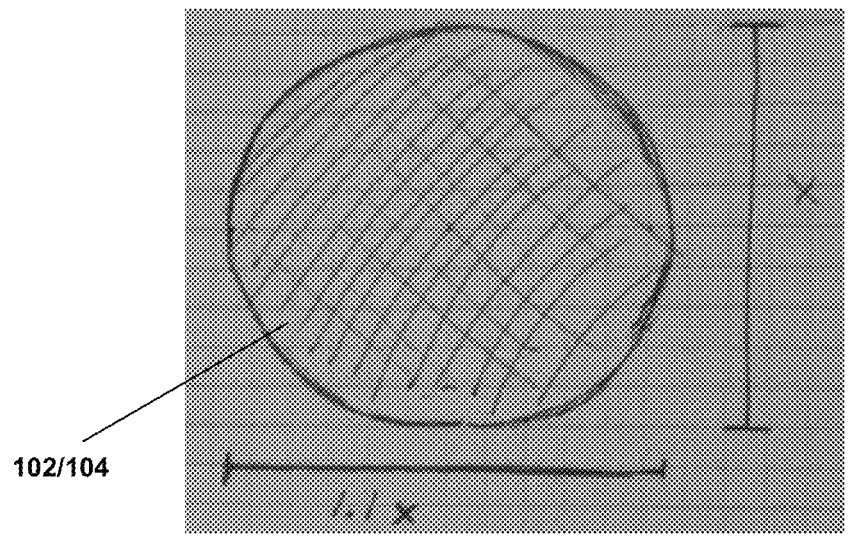
FIG. 12B depicts an example ovoid cross sectional geometry of portions of one embodiment.

As shown in FIG. 5, apical embrasures 130 can each comprise a narrow isosceles triangle, with the dental contact point as the apex. This spatial configuration can, in embodiments, be best accessed with a device having an ovoid cross-sectional shape. Referring to FIG. 12B, for example, an ovoid cross-sectional shape can be used in an embodiment. In an embodiment, as indicated by FIG. 12B, the ovoid cross section can be defined by a diameter of x on one side, and a diameter of 1.1× on the elongated side. In other embodiments, additionally elongated or less elongated configurations are also used. In embodiments, the entire device 102 or 104 comprises an ovoid cross-sectional shape. In other embodiments, portions of device 102 or 104, such as needle and thread portions 114 and 116, ribbed segment 118, and/or clasp 112 can comprise an ovoid cross-sectional shape. Additional material provided by an ovoid shape adds integrity to the tensile strength of device 102 or 104. Further, an ovoid cross-section provides the benefit of not having edges that could potentially lacerate or abrade the gingival papilla.

Figure 12C:
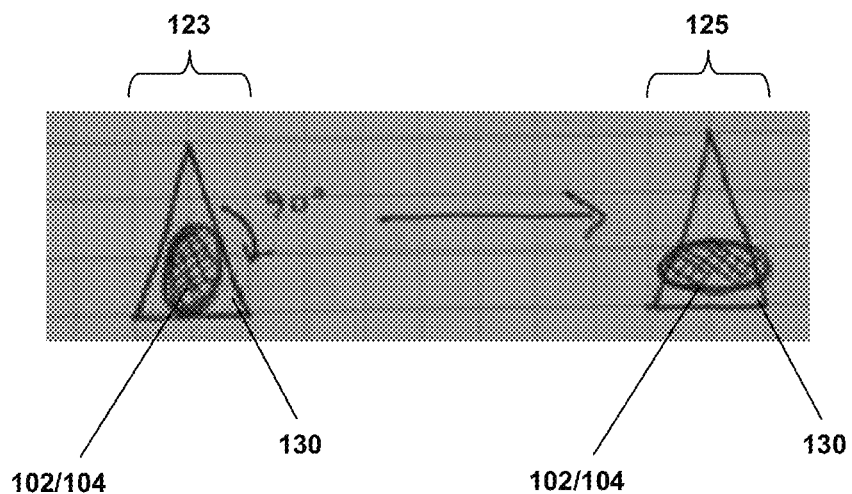
FIG. 12C depicts an example ovoid cross-sectional geometry of portions of one embodiment within an apical embrasure, according to an embodiment.

Referring to FIG. 12C, an ovoid cross-section further allows device 102 or 104 to access apical embrasures 130 more easily when ovoid shape is 90 degrees rotated away from the intended vertical plane, as shown in configuration 123. In embodiments, an ovoid cross-sectional configuration fills the apical embrasures 130 space better than a round cross-sectional shape, as illustrated by configuration 123. In embodiments, once device 102 or 104 is passed through both embrasures and secured, device 102 or 104 can be rotated 90 degrees, as shown by configuration 125. The rotation of device 102 or 104 as shown from configuration 123 to configuration 125 further strengthens the engagement between device 102 or 104 and teeth adjacent to device 102 or 104. In embodiments, such a configuration is minimally compressible in the transverse axis. As a result, the mechanical advantage can act to splay the teeth, so the long axis and short axis are not very different. In embodiments, the long axis can be, for example 5-15% greater than the short axis.

Figure 13:
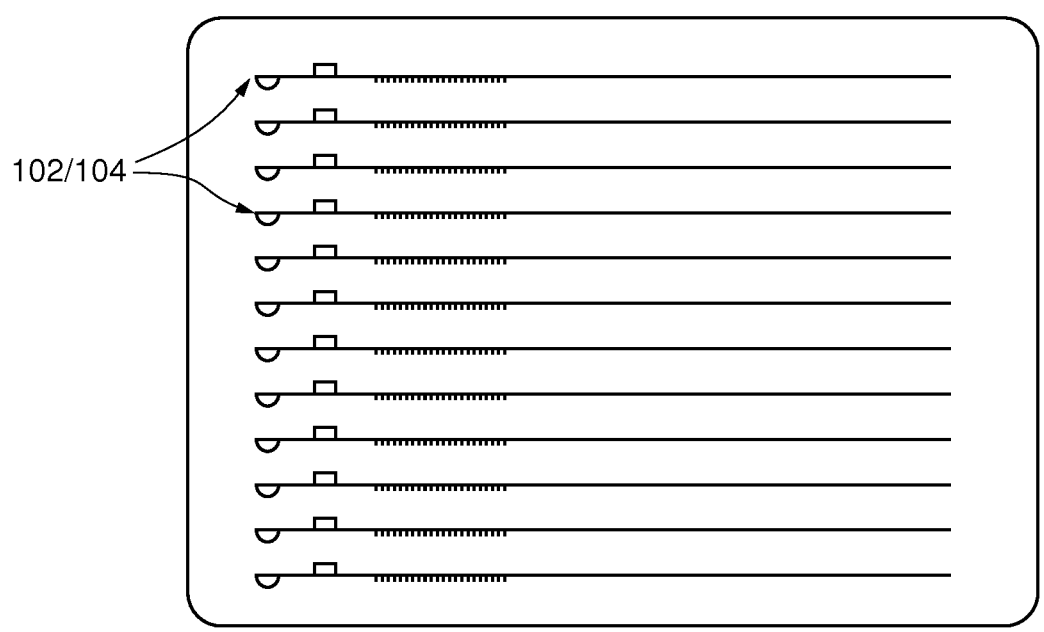
FIG. 13 depicts an example kit of dental occlusion ties and tension band ties, according to an embodiment.

A plurality of ties 102 and/or 104 with various dimensions and geometries to optimize access and interface with specific individuals' anatomical geometry can be packaged in a kit as shown in FIG. 13. In one embodiment, the ties 102 and/or 104 can be provided on a card, in a box, pouch, compartmentalized container or other container, or in or on some other receptacle form. The kit could be provided as a disposable system, wherein all unused components are discarded, or the kit could be provided in a reusable receptacle where the unused bands are kept for subsequent procedures. Though ties 102 and 104 generally will be single-use and thereafter disposable, in embodiments components can be multi-use, thereby suitable for sterilization and reuse. For example, a metal trimming or other tool can be provided in a kit, or a single tool can be provided as part of a kit comprising sub-kits of ties 102 and/or 104 and/or other components, wherein the tool can be sterilized as part of routine medical tool sterilization processes and thereafter reused.

Figure 16:
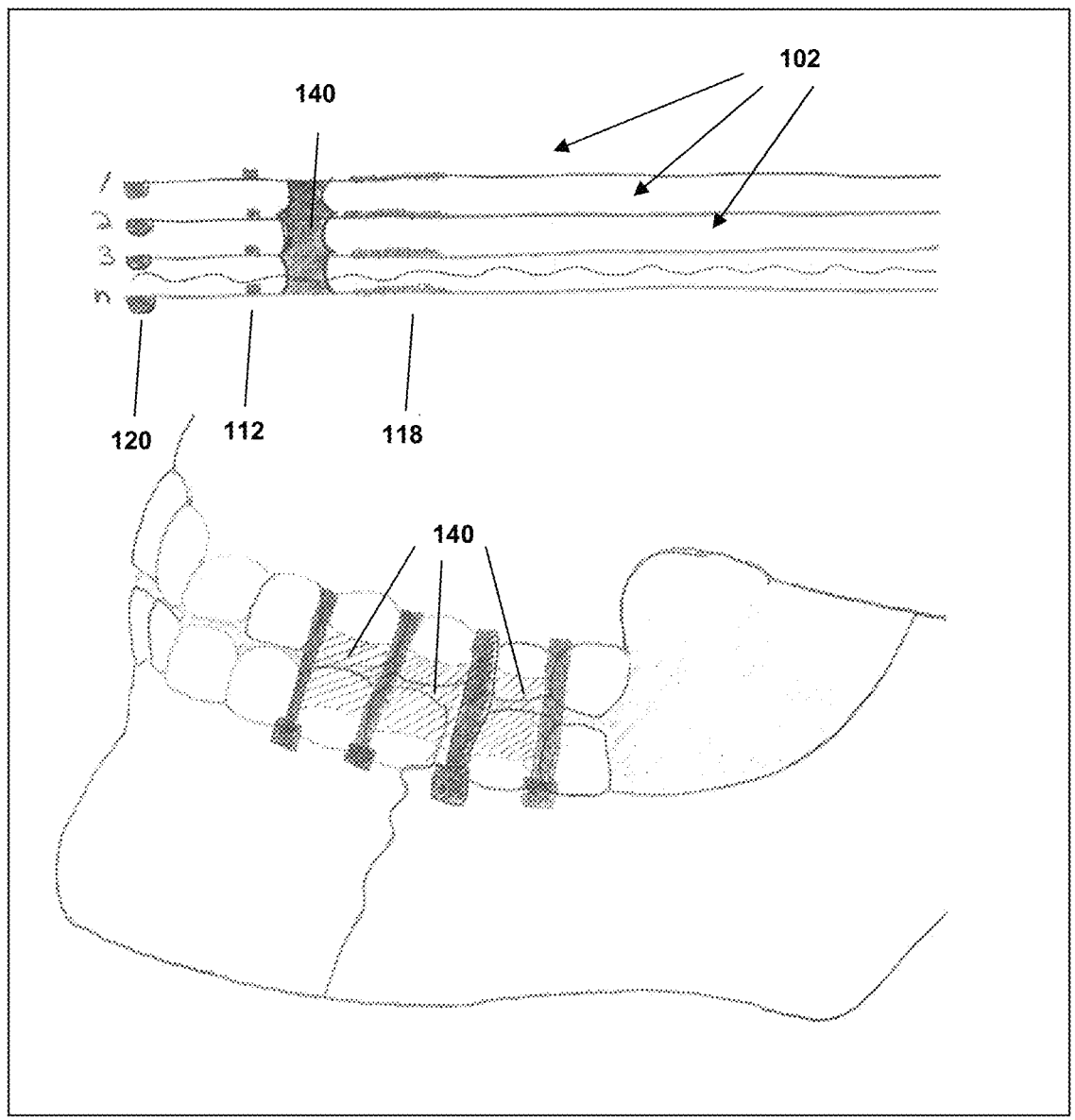
FIG. 16 depicts a composite dental occlusion tie comprising two or more dental occlusion ties linked together, according to an embodiment.
Figure 17:
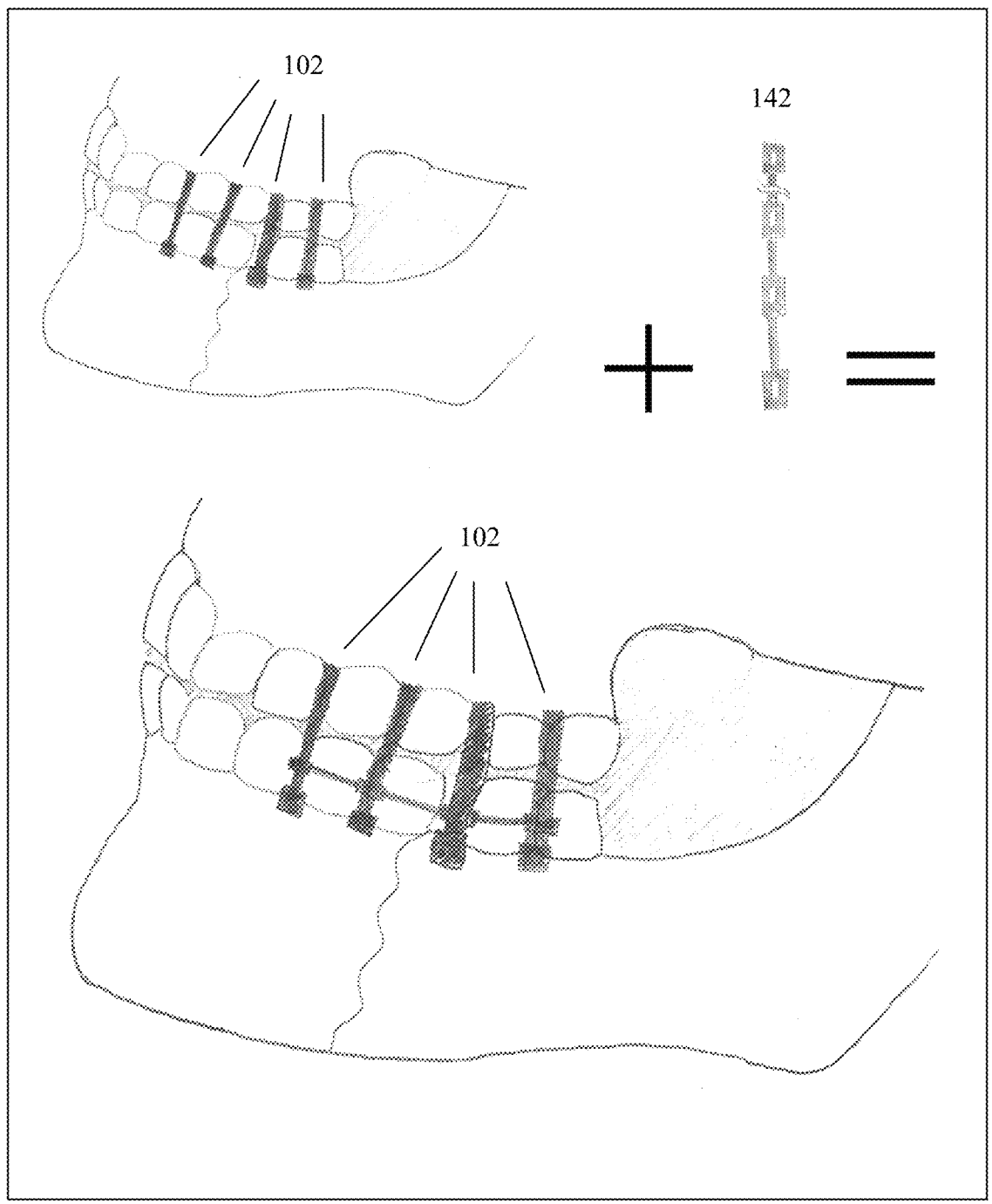
FIG. 17 depicts an example application with cross-linking DO and TB ties, according to an embodiment.
Figure 18:
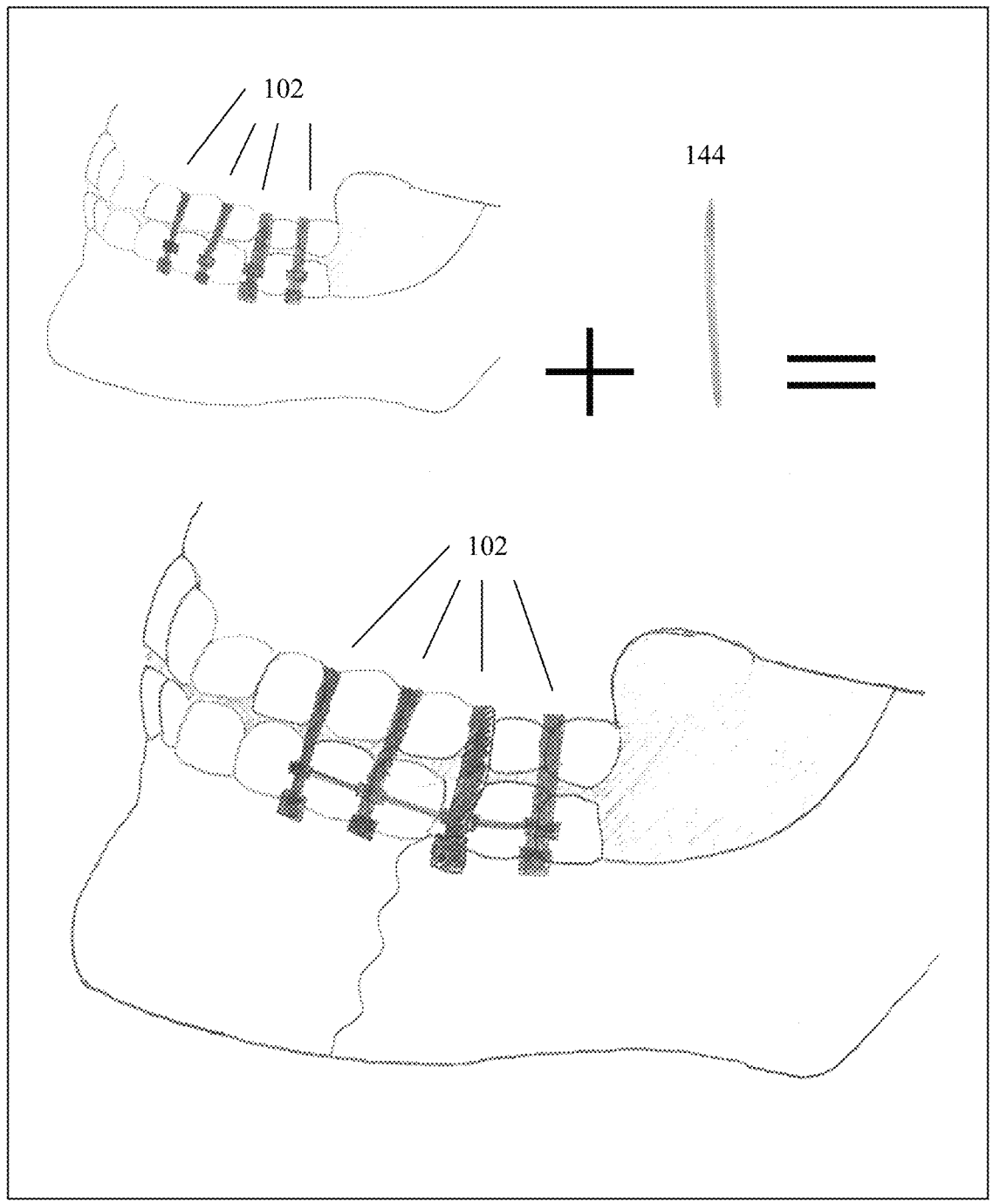
FIG. 18 depicts an example application with cross-linking DO and TB ties, according to an embodiment.

The strength of maxillo-mandibular fixation can increase with the use of multiple ties, though the number and placement of ties for any particular patient can vary according to a variety of factors including anatomy, facture or other injury position, dental health and others. Further, applying ties to sequential apical embrasures 130 can increase the strength of the overall hold by limiting the potential of the ties to splay two adjacent teeth apart, risking the tie to "floss out" of the dental embrasure 130. In one example, system of devices 102 or 104 comprises two or more DO ties 102 in parallel that are physically linked with a composite portion 140 between their ribbed portions 118 and clasp portions 112. This dental occlusion device 102 could span the segment of the mandible containing the fracture which could provide stability to limit distraction at the fracture line. In this embodiment, a TB tie 104 could be unnecessary. This is depicted in one example in FIG. 16. Further, dental occlusion ties 102 can be cross-linked by a separate coupling mechanism 142 as depicted in FIG. 17. Alternatively, the cross-linking clasps could be components of the dental occlusion ties 102 and the cross-linking member 144 could be an elongate body as depicted in FIG. 18. Other configurations and particular characteristics of coupling mechanism 142 and/or cross-linking member 144 can be used in other embodiments, with FIGS. 17 and 18 depicting example embodiments only.

In some situations, however, non-adjacent TB ties 104 can be used, as depicted in FIG. 14. For example, the TB tie 104 includes multiple clasp mechanisms to secure multiple teeth in FIG. 14. The clasps 112 in this example secure teeth that are not immediately adjacent to the fracture. Specifically, no clasp 112 is applied to the teeth adjacent to the fracture as this could further loosen teeth already unstable from the fracture near the tooth roots. The teeth immediately adjacent to the loose teeth provide the sites of attachment for the clasps 112.

Figure 21:
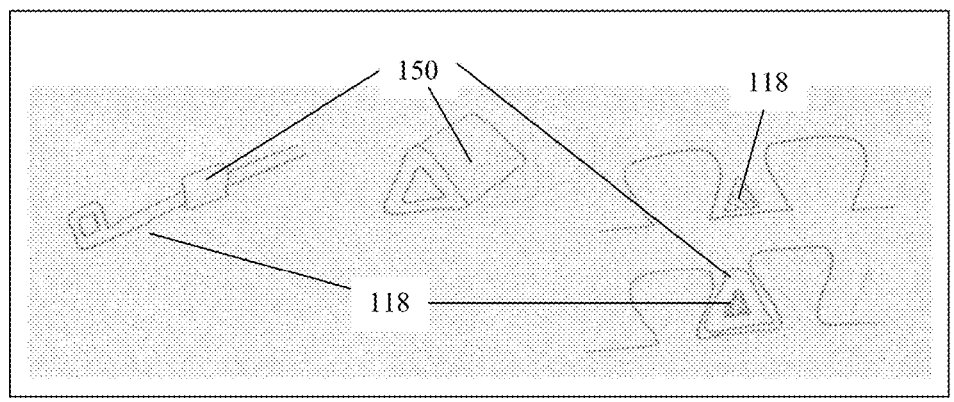
FIG. 21 depicts an example bumper portion, according to an embodiment.

In still other embodiments, spacers, bumpers and/or bands 150 or other components configured to aid in placement or retention of DO ties 102 and/or TB ties 104, and being separate from or integrated with DO ties 102 and/or TB ties 104, can be used. For example, bumpers or bands 150 can be used with ties 102 and/or 104 in situations in which a patient is missing a tooth, a tooth is loose, or an interdental space is large or otherwise configured such that tie 102 and/or 104 could more easily slip out. In one embodiment, a bumper 150 could be placed around tie 102 and/or 104 to increase a diameter, alter a cross-section or change a way in which the tie 102 or 104 interacts with a tooth or interdental space (FIG. 21). In other embodiments, varied diameter ties 102 and/or 104 can be used to address sizing situations such as in situations in which a patient is missing a tooth, a tooth is loose, or an interdental space is large or otherwise configured such that tie 102 and/or 104 could more easily slip out. Still other components, accessories and combinations thereof are contemplated in further embodiments.

Figure 15:
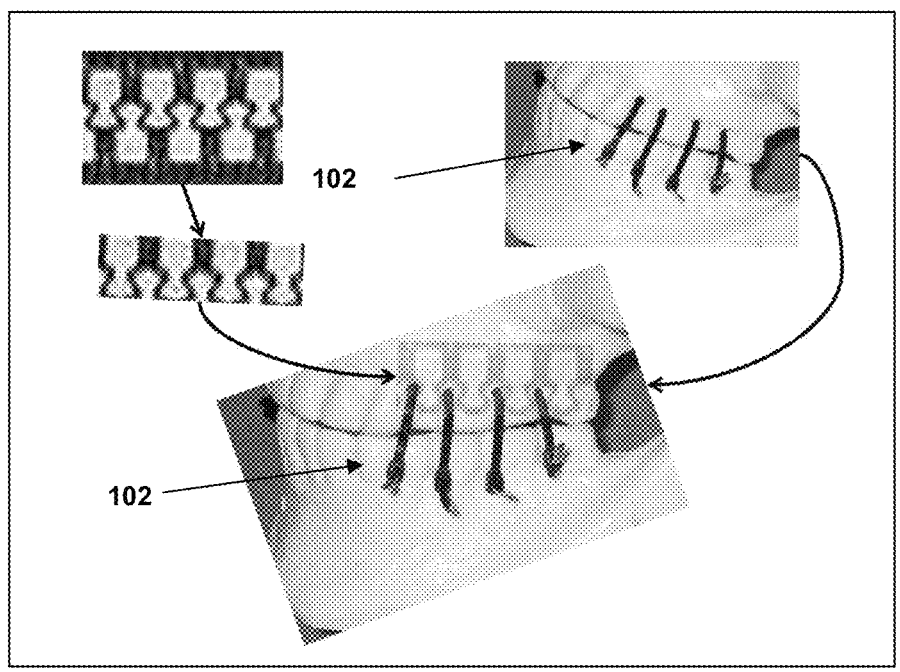
FIG. 15 depicts an example of sequential dental embrasures secured with dental occlusion ties, according to an embodiment.

Embodiments of the proposed devices, systems, kits and methods differ from and improve upon conventional approaches in multiple ways. For example, embodiments leverage the opportunity to secure the upper and lower dentition by harnessing the triangular-shaped apical embrasure 130 between individual teeth in a unique way. This contrasts with arch bar wires, Ivy loops, and Ernst ligatures which wrap around the teeth circumferentially to provide a physical hold of individual teeth. The triangular pocket of the apical embrasure 130 is defined by the geometry of the adjacent teeth and the gingival papilla 132 (as in FIG. 5). The combination of inter-digitated devices and adjacent teeth allows the interface of the devices 102 and 104 with the teeth to hold tightly similar to inter-digitating teeth of a standard "zipper." See, e.g., FIG. 15. Additionally, unlike most other approaches to maxillo-mandibular fixation, no wire manipulation (twisting, bending, cutting, tightening) is needed. This can make use of embodiments more convenient and less expensive to apply as well as less painful for patients. The design of the device also provides advantages in embodiments. For example, the device needle portions 114 can have blunt tips in embodiments, lessening risk to the surgical team (as opposed to the risk incurred with sharp, thin wires used in arch bars). Further, the devices 102 and 104 are designed to be applied in ways to minimize trauma to the gingiva (gums) of the patient, thus minimizing discomfort/pain. The devices 102 and 104 can be secured with a low profile hub (as opposed to a cut/"twisty-tied" wire) causing minimal trauma to the surrounding buccal mucosa (cheek lining). The materials used in such a device 102 and 104 (e.g., polymers, ceramics, metals, and others and combinations thereof) can be designed to have minimal "mechanical relaxation" which can minimize the potential of premature loosening over the course of therapy (commonly 2-6 weeks). This contrasts with current application of MMF in which twisted wires secure the apparatus, but the apparatus can loosen as the twisted wires "relax" with time. The devices 102 and 104 also can be released in a simple fashion, likely in a clinic setting as opposed to current maxillomandibular fixation approaches (i.e., arch bars) which commonly utilize a general anesthetic.

Figure 22:
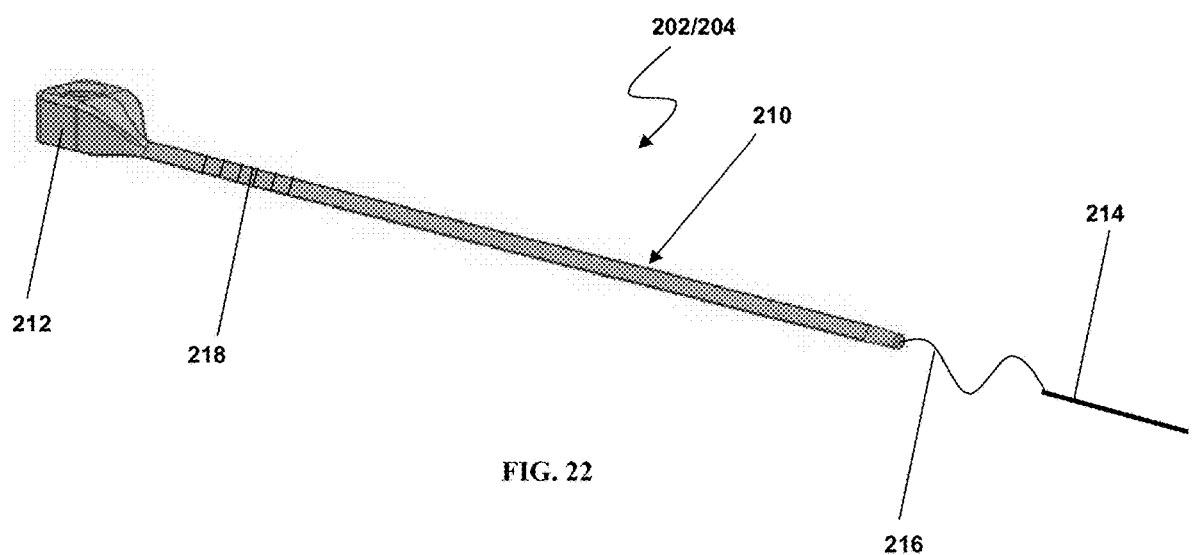
FIG. 22 is a perspective view of an example single dental occlusion tie or tension band tie component parts, according to an embodiment.

In another embodiment, referring to FIG. 22, a DO tie 202 or TB tie 204 is depicted. DO tie 202 and TB tie 204 are substantially similar to DO tie 102 and TB tie 104, respectively, with differences described herein. In an embodiment, the devices 202 and 204 generally comprise an elongate body 210 and a clasp 212. Likewise, elongate body 210 and a clasp 212 are similar to body 110 and clasp 112, with differences described herein.

For example, in an embodiment, body 210 can be considered to comprise a needle portion 214 and a thread portion 216, wherein clasp portion 212 is configured to engage the thread portion 216. In another embodiment, body 210 can comprise an insertion or needle portion 214, a thread portion 216 and a ribbed portion 217. Other combinations of these and other portions can be arranged to form either or both of devices 202 and 204 in other embodiments.

Body 210 can have a unitary construction in an embodiment such that needle portion 214, thread portion 216 and ribbed portion 217 are formed of a single piece of material, or one or more of the portions 214, 216 and/or 218 can be separately formed of the same or a different material and coupled with the other portions. Similarly, in embodiments, clasp 212 can be of unitary construction with one, some or all of portions 214, 216 and/or 218, or clasp 212 can be separately formed and coupled therewith, as will be described. Couplings between one or more of clasp 212 and portions 214, 216 and 218 can be removable or fixed, and can vary in various embodiments of DO ties 202 and/or TB ties 204.

Figure 23:
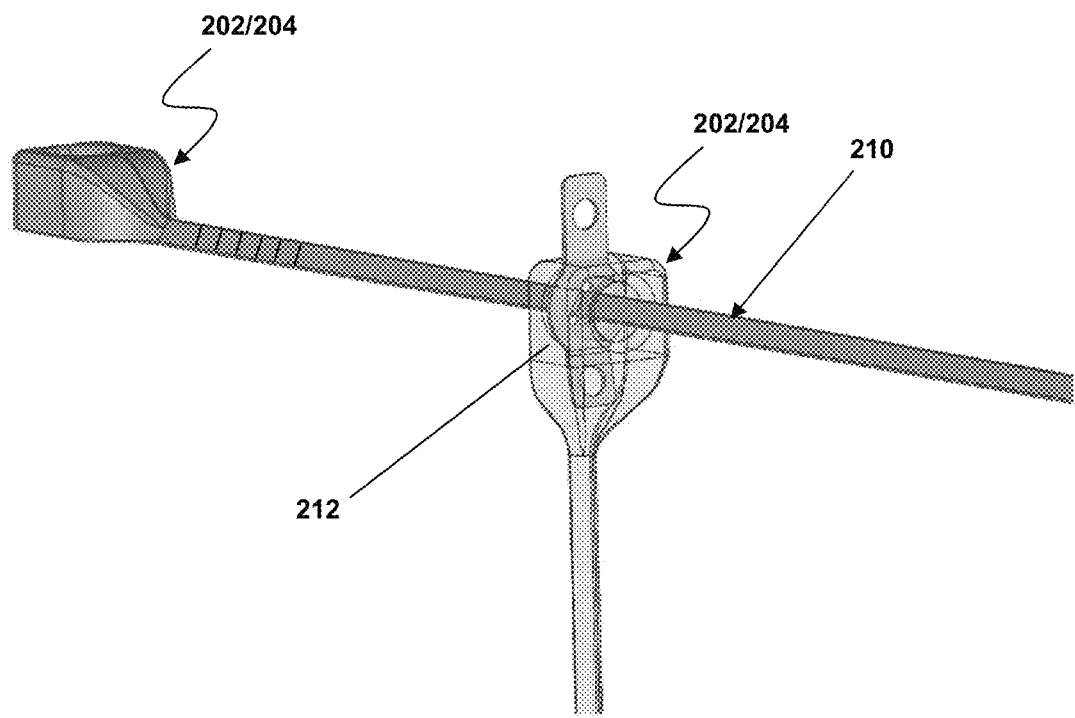
FIG. 23 is a perspective, partially transparent, view of a dental occlusion or tension band tie operably coupled to a second dental occlusion or tension band tie, according to an embodiment.
Figure 24:
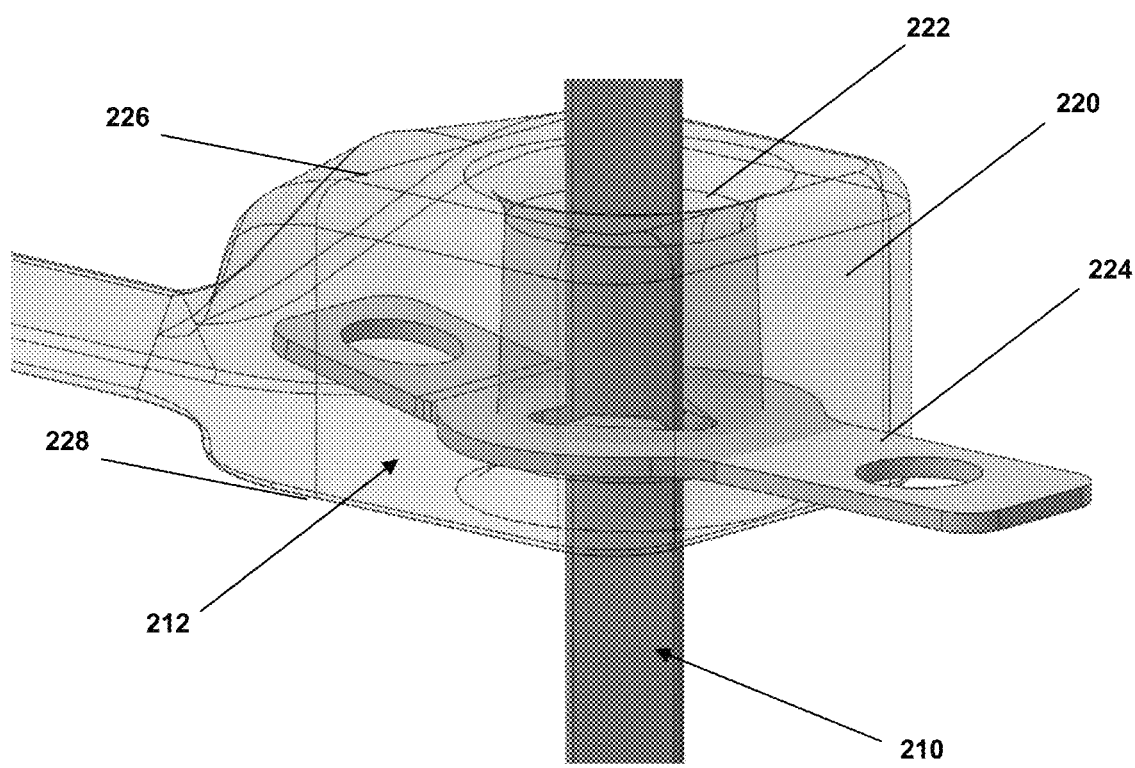
FIG. 24 is a perspective, partially transparent, view of a clasp of a dental occlusion or tension band tie operably coupled to a portion of a body of a dental occlusion or tension band tie, according to an embodiment.

Referring to FIG. 23, a dental occlusion tie 202 or tension band tie 204 is depicted as operably coupled to a second dental occlusion tie 202 or tension band tie 204. For ease of illustration, FIG. 23 depicts two separate devices as operably coupled. In embodiments, devices 202 or 204 can be coupled together within systems of embodiments such that clasp 212 couples two separate devices, as depicted. However, it is readily understood that a single dental occlusion tie 202 or tension band tie 204 can be operably coupled to itself via clasp 212. Referring also to FIG. 24, in an embodiment, clasp 212 comprises housing 220, housing aperture 222, and locking tab 224. Housing 220 is configured to house or contain the components of clasp 212; for example, locking tab 224. In an embodiment, as depicted, housing 220 can be flat on one or more ends. For example, as depicted in FIG. 24, housing 220 comprises a first end 226 and a second end 228. First end 226 and second end 228 are both generally flat. In embodiments, a flat first end 226 and/or second end 228 assists in manufacturing. In other embodiments, housing 220, and particularly, first end 226 and/or second end 228 can be rounded or otherwise shaped, as will be described. In embodiments, housing 220 can be snapped, secured, clipped, or otherwise coupled together from two or more portions. In other embodiments, housing 220 can be formed of a single piece of material. As a result, housing 220 can be hollow, partially hollow, or solid, according to embodiments.

According to an embodiment, housing aperture 222 comprises a void within housing 220. At least a portion of housing aperture 222 extends between first end 226 and second end 228 to create a pass-through void within housing 220. Housing aperture 222 and housing 220 are therefore configured to receive one or more portions of body 210. As depicted, housing aperture is generally cylindrical in shape, with the edges of the cylinder relatively larger than the center of the cylinder. In embodiments, such a configuration aids in the insertion of body 210 through housing aperture 222. In other embodiments, housing aperture can be rounded or edged or otherwise shaped, in other embodiments.

Figure 25:
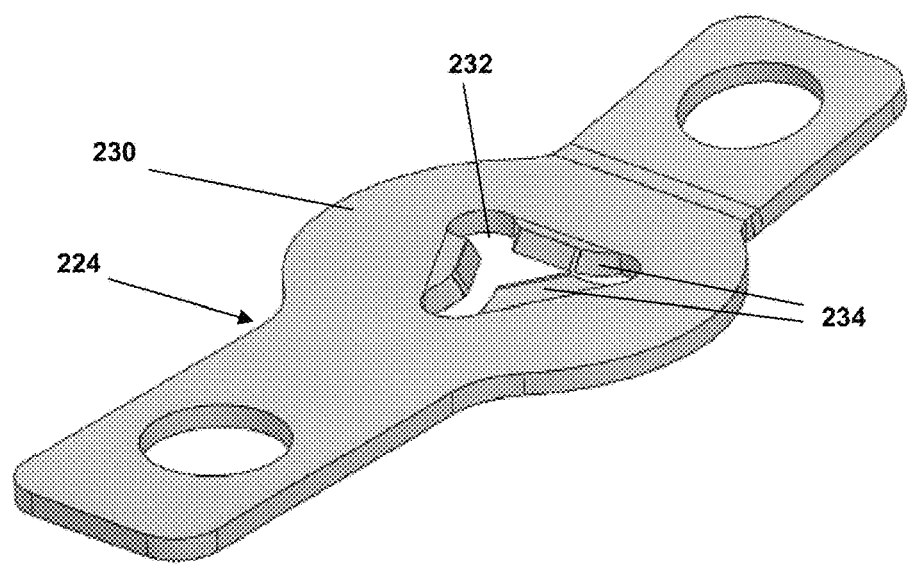
FIG. 25 is a perspective view of a locking tab of a clasp for a dental occlusion or tension band tie, according to an embodiment.
Figure 26:
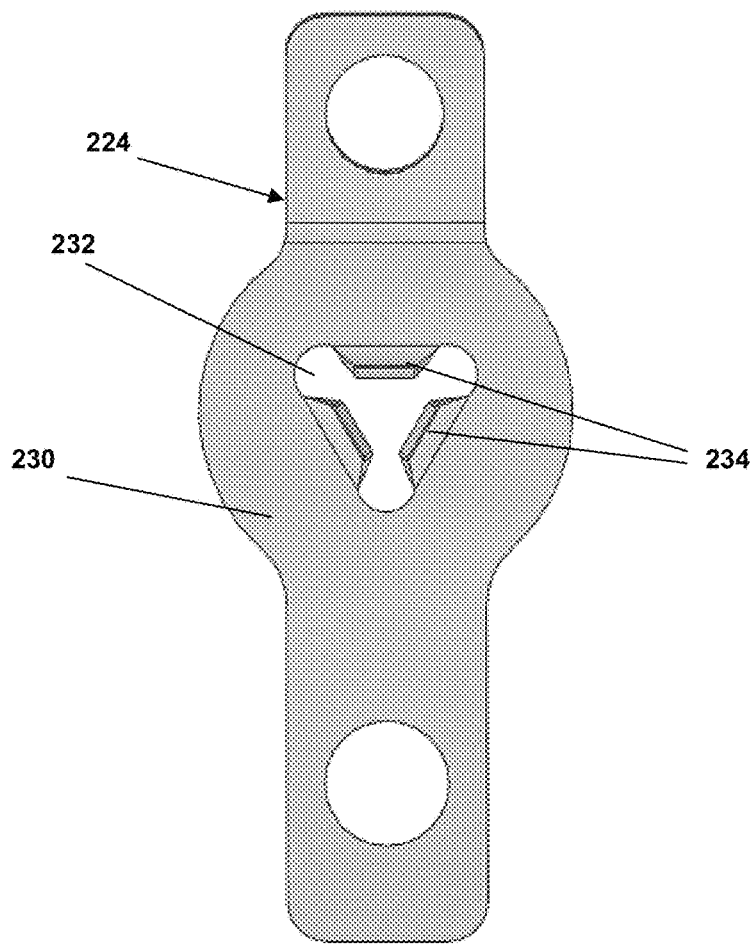
FIG. 26 is a front view of the locking tab of FIG. 25, according to an embodiment.

Referring to FIGS. 25-26, locking tab 224 comprises a tab body 230, a receiving aperture 232, and one or more locking projections 234.

Tab body 230 comprises a length of material configured to envelope or surround receiving aperture 232. In an embodiment, as depicted in FIGS. 25-26, tab body 230 is elongated. Such an elongate body assists in manufacturing, as will be described. In other embodiments, tab body 230 can be shorter or less elongated. In embodiments, tab body 230 or portions of tab body 230 can mirror housing 220, as appropriate. In embodiments, additional material surrounds receiving aperture 232 such that rounded projections protrude from sides of tab body 230. Additional material surrounding receiving aperture 232 provides added support for the locking mechanisms of DO ties 202 and/or TB ties 204, as will be described. Tab body 230 can further comprise one or more apertures other than receiving aperture 232, as depicted. Such apertures can aid in manufacturing. The materials used to make tab body 224 can comprise polymers, ceramics, metals, and others and combinations thereof.

Receiving aperture 232 comprises a void within tab body 224. At least a portion of receiving aperture 232 extends between the respective sides of tab body 234 to create a pass-through void within tab body 234. Receiving aperture 232 is therefore configured to be utilized with housing aperture 222 and housing 220 to receive one or more portions of body 210. According to an embodiment, as depicted, housing aperture is generally triangular in shape. In other embodiments, housing aperture can be rounded or edged or otherwise shaped, in other embodiments. For example, for a DO tie 202 and/or TB tie 204 having a triangularly-shaped body 210, a corresponding triangularly-shaped receiving aperture 232 can be utilized. In other embodiments, for example, with a rounded or circular shaped body 210, a corresponding rounded receiving aperture 232 can be utilized. Other shapes and configurations are also considered.

Within, adjacent, or otherwise coupled to receiving aperture 232, one or more locking projections 234 are configured to interface to body 210. Particularly, in embodiments, locking projections 234 are configured to interface with ribbed portion 218, and more particularly, still, one or more of the ribs of ribbed portion 218. As depicted, a single locking projection 234 is positioned on each edge of the triangularly-shaped receiving aperture 232. In other embodiments, a single locking projection 234 is positioned on only one edge of receiving aperture 232. In other embodiments, two locking projections are positioned respectively on two of the edges of receiving aperture 232. In other embodiments, two or more locking projections 234 are positioned on a respective edge of receiving aperture 232. As will be readily understood by those skilled in the art, other shapes and positional configurations of locking projections can also be utilized.

In embodiments, locking tab 224 can further comprise elements to prevent over-tightening. For example, if DO tie 202 and/or TB tie 204 is slightly over-tightened, one or more components of locking tab 224 can intentionally fail. According to an embodiment, a first locking projection 234 can intentionally snap off, bend, or otherwise release tension on the coupled body 210. In such an embodiment, body 210 can release to a second (likely adjacent) locking projection 234. In other embodiments, other portions of locking tab 224 and/or housing 220 can intentionally fail in a similar manner to prevent over-tightening.

Figure 27:
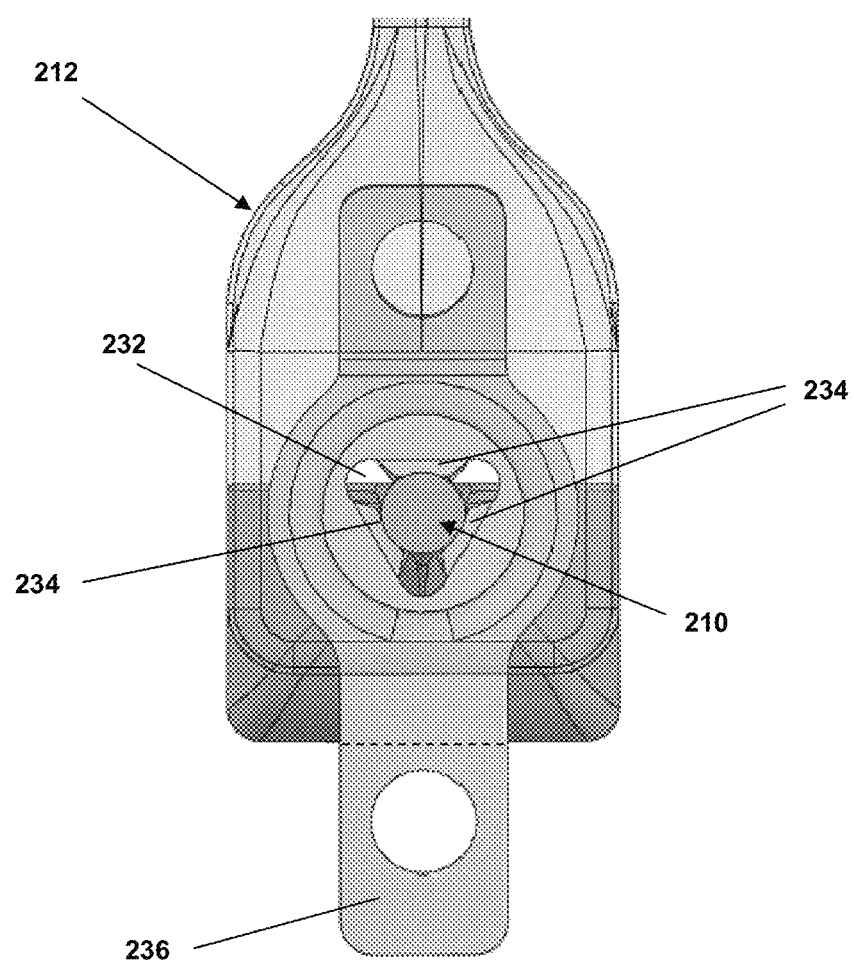
FIG. 27 is a top, partially transparent, view of the clasp of a dental occlusion or tension band tie of FIG. 24 operably coupled to a dental occlusion or tension band tie body, according to an embodiment.

Additionally, in embodiments, locking tab 224 can further comprise a removable portion 236. Referring to FIG. 27, once clasp 212 is assembled (as will be described), removable portion 236, as shown in dashed line, can be removed from the clasp 212 assembly. In embodiments, removable portion 236 can remain intact with the rest of tab body 230. In other embodiments, removable portion 236 comprises additional or less material of tab body 230 than shown in FIG. 27. In embodiments, removable portion 236 is removed from tab body 230 so that the remainder of tab body 230 is flush with the portion of housing 220 that removable portion 236 once extended. In other embodiments, once removable portion 236 is removed, the remainder of tab body 230 is below the surface of the portion of housing 220 that removable portion 236 once extended.

Referring again to FIG. 27, a body 210 is shown as operably coupled to clasp 212. As depicted, one or more portions of body 210 is threaded through housing aperture 222 and receiving aperture 232 to interface to one or more locking projections 234. As such, receiving aperture 232 is at least partially aligned with housing aperture 222. In the embodiment depicted, receiving aperture 232 is fully aligned with housing aperture 222 such that no portion of receiving aperture 232 is blocked by a portion of housing 220. In other embodiments (not shown), only a portion of receiving aperture 232 is aligned with housing aperture 222 such that at least a portion of the void of receiving aperture 232 is blocked by a portion of housing 220. In the embodiment depicted in FIG. 27, each of the three locking projections 234 is in contact with body 210. In other embodiments (not shown), fewer of the locking projections 234 can be in contact with body 210. In an embodiment, locking projections 234 interface with ribbed portion 218, and more particularly, still, one or more of the ribs of ribbed portion 218.

Figure 28:
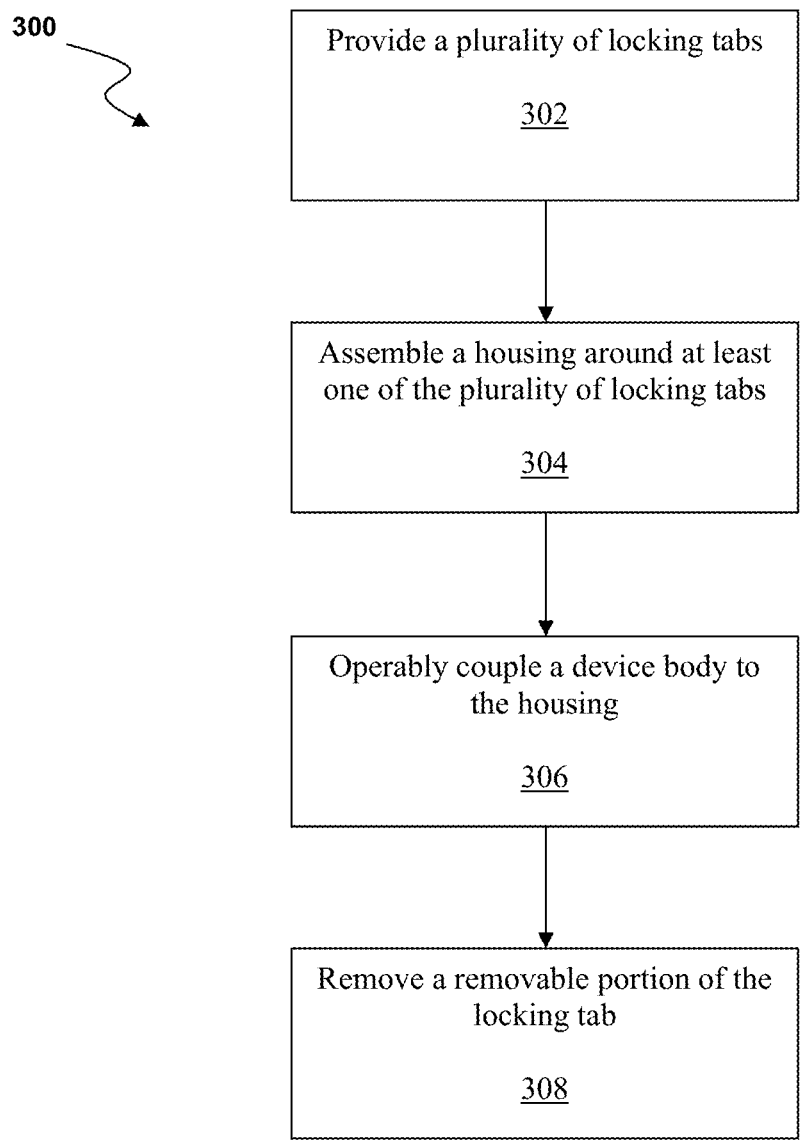
FIG. 28 is a flowchart of a method of making a dental occlusion or tension band tie, according to an embodiment.

Referring to FIG. 28, a method 300 of manufacturing a DO tie and/or TB tie is depicted. In embodiments, components or steps of method 300 are utilized to manufacture DO tie 202 and/or TB tie 204 as shown in FIGS. 22-27. In other embodiments, components or steps of method 300 are utilized to manufacture other variations or embodiments of a DO tie and/or TB tie, such as devices 102 and 104.

At 302, a plurality of locking tabs is provided. In an embodiment, the plurality of locking tabs are substantially similar to locking tabs 224. In other embodiments, other locking tabs are provided. A support structure can be operably coupled to the plurality of locking tabs 224 to aid in manufacturing. For example, in an embodiment, the plurality of locking tabs 224 can be aligned substantially parallel to each other in a row, with a removable support structure coupling all of the locking tabs 224 in a row.

At 304, a housing is assembled around at least one of the plurality of locking tabs 224. In embodiments, the housing is substantially similar to housing 220. In other embodiments, other housings are provided. In an example embodiment, each of the housings 220 are assembled around each of the plurality of locking tabs 224 at the same time. In other embodiments, each of the housings 220 are assembled sequentially around each of the plurality of locking tabs 224.

For example, housing 220 can be formed by extrusion onto each of the locking tabs 224 by melting a material, such as plastic, and forming the material into a continuous profile. In embodiments, any of a number of suitable coating techniques can be utilized including, but not limited to, extruding, casting, printing such as inkjet printing, flexographic printing, rotogravure, curtain coating, spraying, gravure, mire rod coating, and the like. In other embodiments, housing 220 can be snapped, secured, clipped, or otherwise coupled together from two or more portions onto a respective locking tab 224.

At 306, a device body is operably coupled to the housing. In embodiments, the device body is substantially similar to body 210. In other embodiments, other bodies are provided. In one embodiment, each body 210 is formed at the same time as housing 220. For example, body 210 or portions thereof can be formed by the same extrusion technique as housing 220. In other examples, each body 210 can be formed after housing 220 is provided such that each of the bodies 210 are operably coupled sequentially to the respective housings.

At 308, a removable portion of a locking tab is removed. In embodiments, the removable portion is substantially similar to removable portion 236. In other embodiments, other removable portions are provided. For example, the removable portion can further comprise a removable support structure coupling all of the locking tabs 224, as described above. By removing the removable portion or removable support structure, a streamlined device 202 and/or 204 is created. Moreover, due to the small size of devices 202/204, the removable portion and adjacent coupling of devices provided by the removable portion provides greater flexibility in manufacturing.

A DO tie and/or TB tie according to embodiments described herein can utilize any number of suitable clasps. For example, referring to FIG. 29, according to an embodiment, DO tie 400 is depicted. DO tie 400 is substantially similar to any of the DO ties and/or TB ties described above, but includes clasp 402 and body 412.

Figure 29:
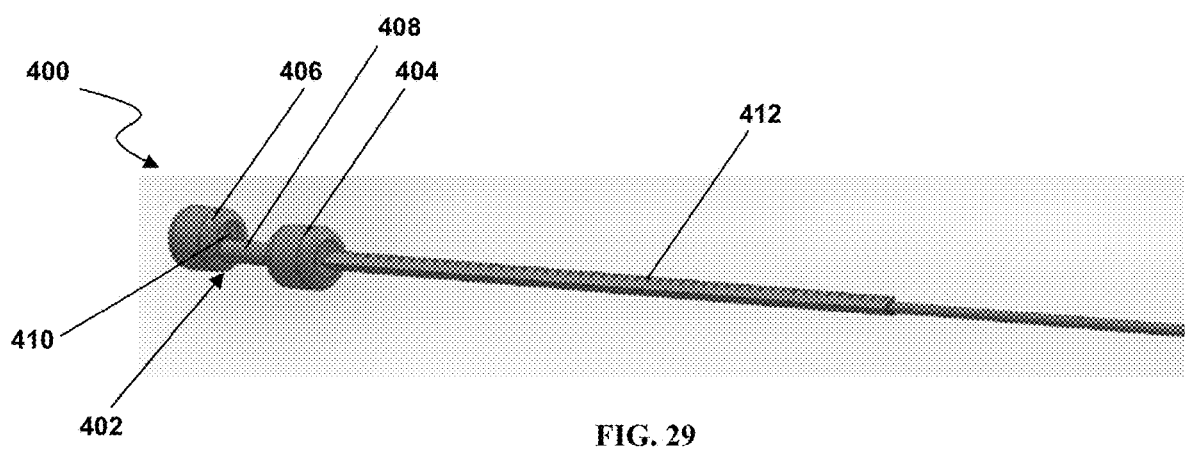
FIG. 29 is a perspective view of a dental occlusion or tension band tie having a triangular body cross-section, according to an embodiment.

Clasp 402 comprises a first portion 404, a second portion 406, and a connecting portion 408. First portion 404 is configured much like housing 220 such that a body 412 extends therefrom. As depicted, DO tie 400 comprises body 412 having a triangular cross section (a "triangular body 412"). Connecting portion 408 extends opposite triangular body 412 from first portion 404, thereby operably coupling second portion 406 and first portion 404. Second portion 406 can be substantially similar to first portion 404. In other embodiments, second portion 406 is differently shaped from first portion 404. As depicted in FIG. 29, second portion 406 can be offset from the center of first portion 404. In other embodiments, second portion 406 can be directly in line with the center of first portion 404. Due to triangular cross-sectional shape of body 412, second portion 406 comprises a triangular receiving aperture 410. Triangular receiving aperture 410 is configured to receive one or more portions of triangular body 412. When DO tie 400 is in a locked position such that triangular body 412 is threaded and locked into triangular receiving aperture 410, connecting portion 408 acts as a "bridge" that can easily be severed or cut so DO tie 400 can be easily removed. In embodiments, a suture scissors or other cutting implement can be placed proximate connecting portion 408. In embodiments, connecting portion 408 is raised from the housing or other portions of clasp 402 due to the projections of first portion 404 and second portion 406 relative to connecting portion 408. In embodiments, the spacing of these projections allows the user to position a cutting tool along the connecting portion 408. In an embodiment, the length of a distal edge of first portion 404 to a distal edge of second portion 406 is 13 mm. In other embodiments, other lengths between a distal edge of first portion 404 to a distal edge of second portion 406 are considered. Further, in embodiments, a relative height of first portion 404 or second portion 406 is 3 mm. In other embodiments, other heights of first portion 404 and second portion 406 are considered. In still other embodiments, as mentioned, the dimensions and sizes of first portion 404 and second portion 406 are relatively different.

Figure 30:
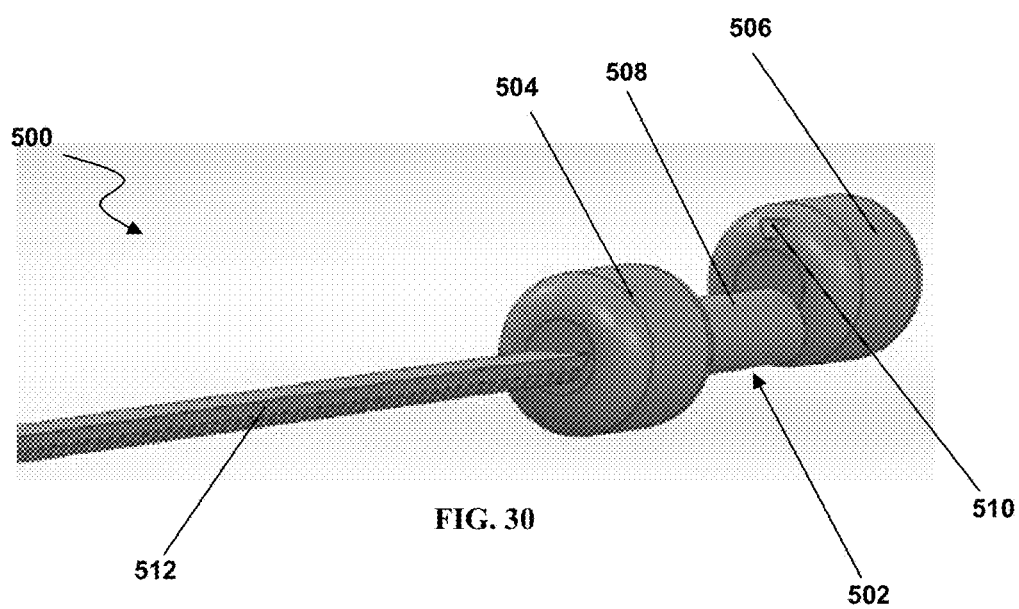
FIG. 30 is a perspective view of a dental occlusion or tension band tie having a trapezoidal body cross-section, according to an embodiment.

In another embodiment, referring to FIG. 30, a DO tie 500 is depicted. DO tie 500 can be substantially similar to DO tie 400, according to embodiments. DO tie 500 comprises a clasp 502. Clasp 502 comprises a first portion 504, a second portion 506, and a connecting portion 508. The components of clasp 502 are respectively similar to the corresponding components of clasp 402. However, in an embodiment, DO tie 500 comprises a body 512 having a trapezoidal cross-section (a "trapezoidal body 512"). As a result, in embodiments, second portion 506 comprises a trapezoidal receiving aperture 510. Trapezoidal receiving aperture 510 is configured to receive one or more portions of trapezoidal body 512.

Figure 31:
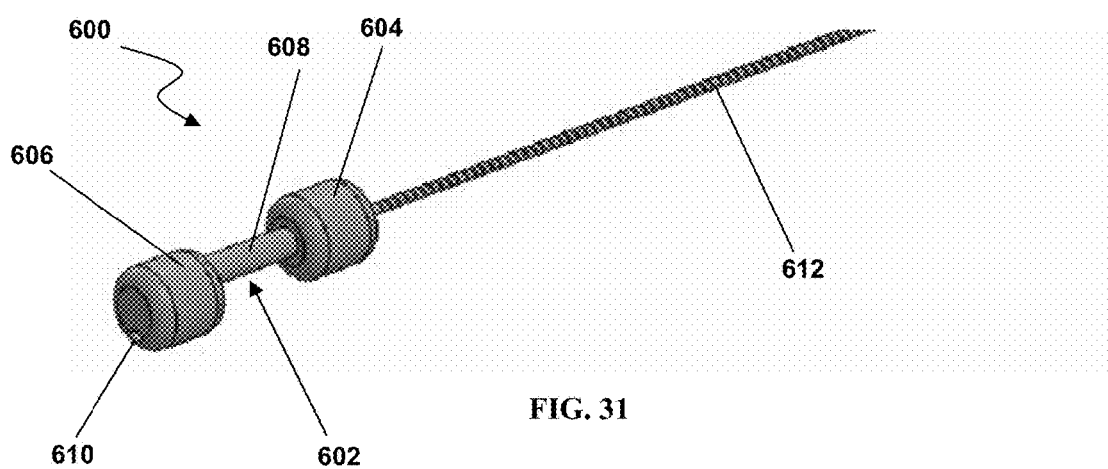
FIG. 31 is a perspective view of a dental occlusion or tension band tie having an elliptical body cross-section, according to an embodiment.

In another embodiment, referring to FIG. 31, a DO tie 600 is depicted. DO tie 600 can be substantially similar to DO tie 400 and/or DO tie 500, according to embodiments. DO tie 600 comprises a clasp 602. Clasp 602 comprises a first portion 604, a second portion 606, and a connecting portion 608. The components of clasp 602 are respectively similar to the corresponding components of clasp 602. However, in an embodiment, DO tie 600 comprises a body 612 having an elliptical cross-section (an "elliptical body 612"). As a result, in embodiments, second portion 606 comprises an elliptical receiving aperture 610. Elliptical receiving aperture 610 is configured to receive one or more portions of elliptical body 612.

Figure 32A:
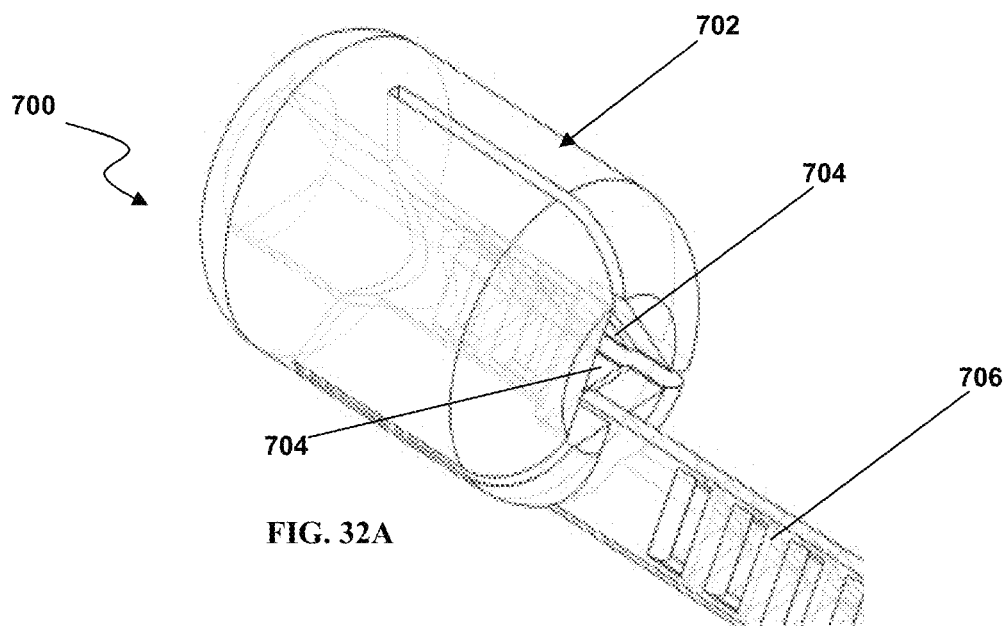
FIG. 32A is a perspective transparent view of a dental occlusion or tension band tie having a clasp with internal ribs in a co-linear orientation, according to an embodiment.
Figure 32B:
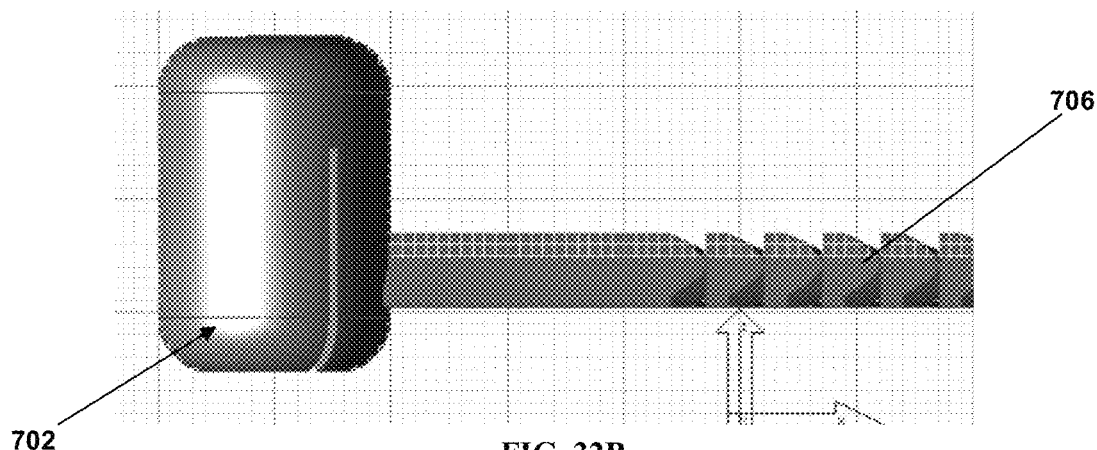
FIG. 32B is a side view of the dental occlusion or tension band tie of FIG. 32A in a perpendicular orientation, according to an embodiment.
Figure 32C:
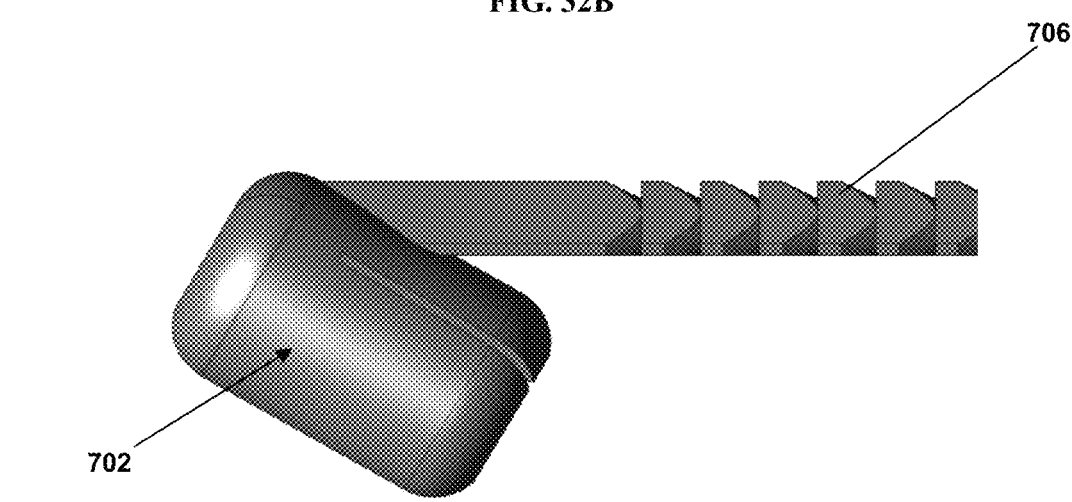
FIG. 32C is a side view of the dental occlusion or tension band tie of FIG. 32A in an angled offset orientation, according to an embodiment.

In another embodiment, referring to FIGS. 32A-32E, a DO tie 700 is depicted. DO tie 700 can be substantially similar to any of the aforementioned DO ties, according to embodiments. In an embodiment, DO tie 700 comprises clasp 702. Clasp 702 can comprise a plurality of internal ribs 704, as shown in the transparent perspective view of DO tie 700. In embodiments, the plurality of internal ribs 704 are each or as a set configured to interface to the ribs of body 706 of DO tie 700. For example, two sets of ribs 704 within clasp 702 can interface to body 706. In another embodiment, three sets of ribs 704 within clasp 702 can interface to body 706. In embodiments, clasp 702 is configured to pivot about body 706. For example, referring to FIG. 32B, clasp 702 can be positioned in a perpendicular orientation. In other embodiments, referring to FIG. 32C, clasp 702 can be positioned in an angled offset orientation. Such pivoting allows for easier insertion of body 706 into clasp 702, as depicted in FIGS. 32D-32E.

In another embodiment, referring to FIGS. 33A-33B, a DO tie 800 is depicted. DO tie 800 can be substantially similar to any of the aforementioned DO ties, according to embodiments. In an embodiment, DO tie 800 comprises clasp 802. According to an embodiment, as depicted, clasp 802 comprises a floating bridge 804 adapted to interface to body 806.

In another embodiment, referring to FIGS. 34A-33D, a DO tie 900 is depicted. DO tie 900 can be substantially similar to any of the aforementioned DO ties, according to embodiments. In an embodiment, DO tie 900 comprises clasp 902. According to an embodiment, as depicted, clasp 902 comprises a bridge portion 904 that includes a spacing of a body 906 from an edge of clasp 902 creating a raised entry point for body 906 into clasp 902. In embodiments, the spacing of body 906 from the edge of clasp 902, and particularly, bridge portion 904, allows the user to position a cutting tool at body 906 proximate clasp 902 so that the cutting tool has room to operate.

Figure 35:
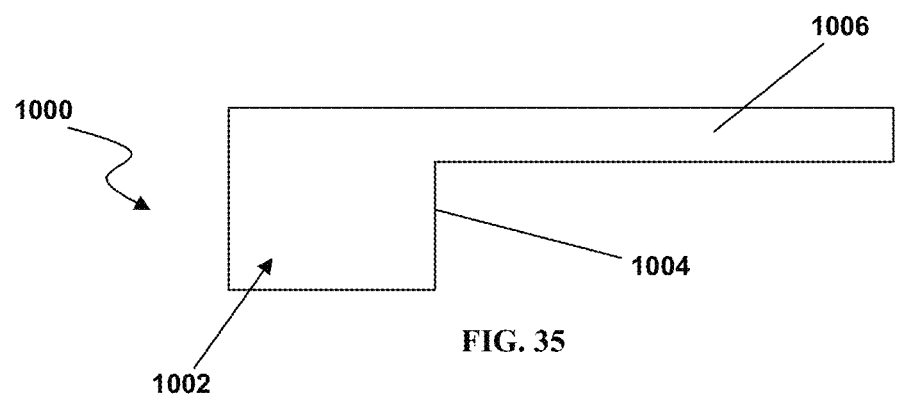
FIG. 35 is a side view of a dental occlusion or tension band tie having a clasp with a raised entry point, according to an embodiment.

In another embodiment, referring to FIG. 35, a DO tie 1000 is depicted. DO tie 1000 can be substantially similar to any of the aforementioned DO ties; particularly, DO tie 900. FIG. 35 is a side view of DO tie 1000 having a clasp with a raised entry point, according to an embodiment. In embodiments, DO tie 1000 comprises a clasp 1002. As depicted, clasp 1002 comprises a bridge portion 1004 that includes a spacing of a body 1006 from the base of clasp 1002 creating a raised entry point for body 1006 into clasp 1002. In embodiments, the spacing of body 1006 from an edge of clasp 1002, and particularly, bridge portion 1004, allows the user to position a cutting tool at body 1006 proximate clasp 1002 so that the cutting tool has room to operate.

Figure 36:
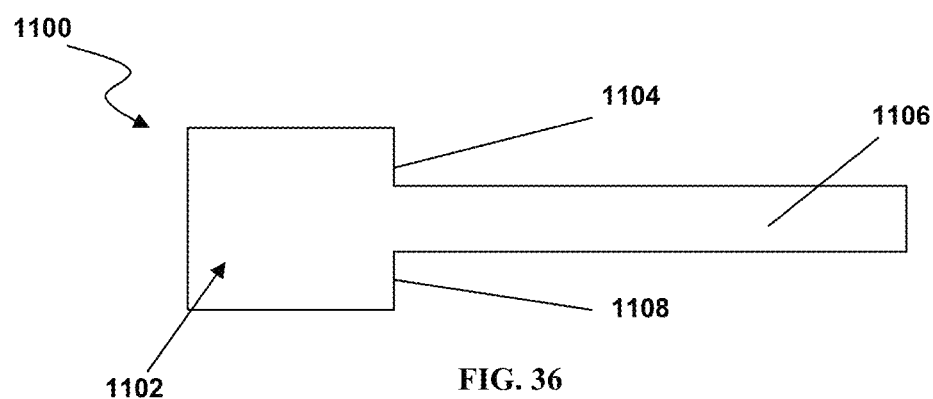
FIG. 36 is a side view of a dental occlusion or tension band tie having a clasp with two raised entry points, according to an embodiment.

In another embodiment, referring to FIG. 36, a DO tie 1100 is depicted. DO tie 1100 can be substantially similar to any of the aforementioned DO ties; particularly, DO ties 900 and 1000. FIG. 36 is a side view of DO tie 1100 having a clasp with two raised entry points, according to an embodiment. In embodiments, DO tie 1100 comprises a clasp 1102. As depicted, clasp 1102 comprises a bridge portion 1104 that includes a spacing of a body 1106 from an edge of clasp 1102 creating a raised entry point for body 1106 into clasp 1102. Further, clasp 1102 comprises a second bridge portion 1108 that includes a spacing of body 1106 from a second edge of clasp 1102 creating a second raised entry point for body 1106 into clasp 1102. In embodiments, the spacings of body 1006 from the edges of clasp 1002, and particularly, bridge portions 1104 and 1108, allow the user to position a cutting tool at the body proximate clasp 1002 so that the cutting tool has room to operate.

Figure 37A:
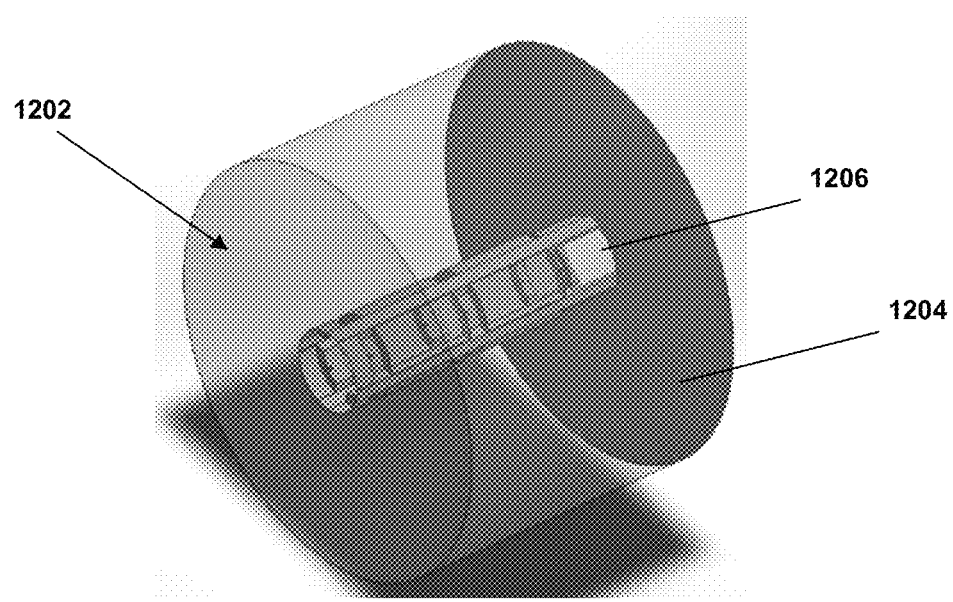
FIG. 37A is a perspective transparent view of a clasp for a dental occlusion or tension band tie, according to an embodiment.
Figure 37B:
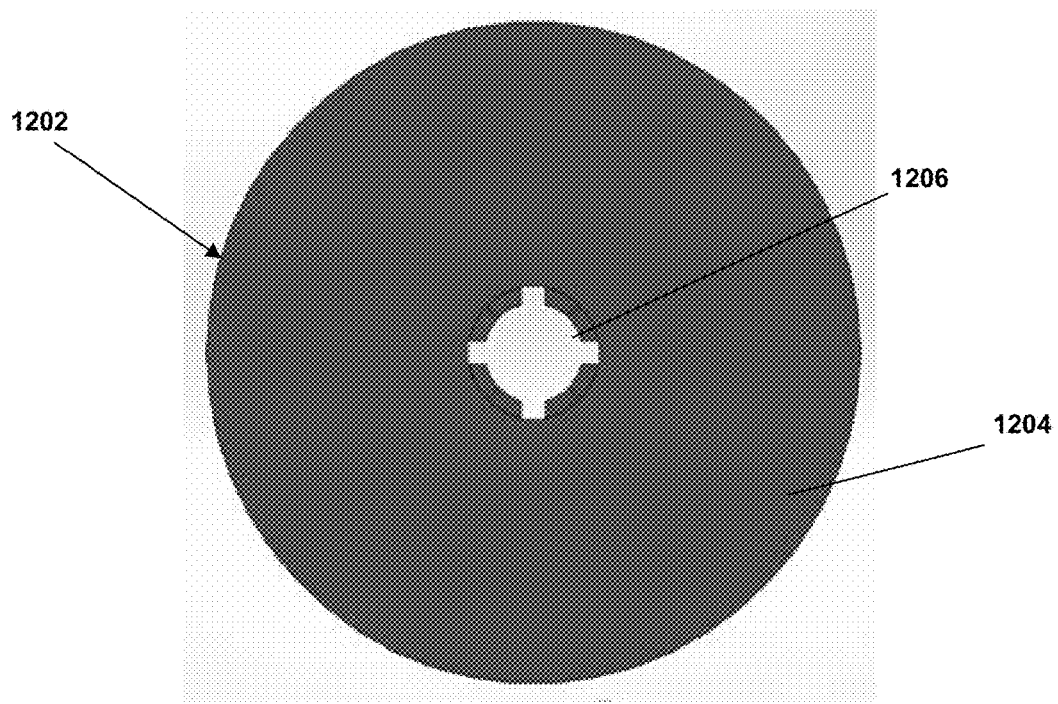
FIG. 37B is a top view of the clasp of FIG. 37A, according to an embodiment.
Figure 37C:
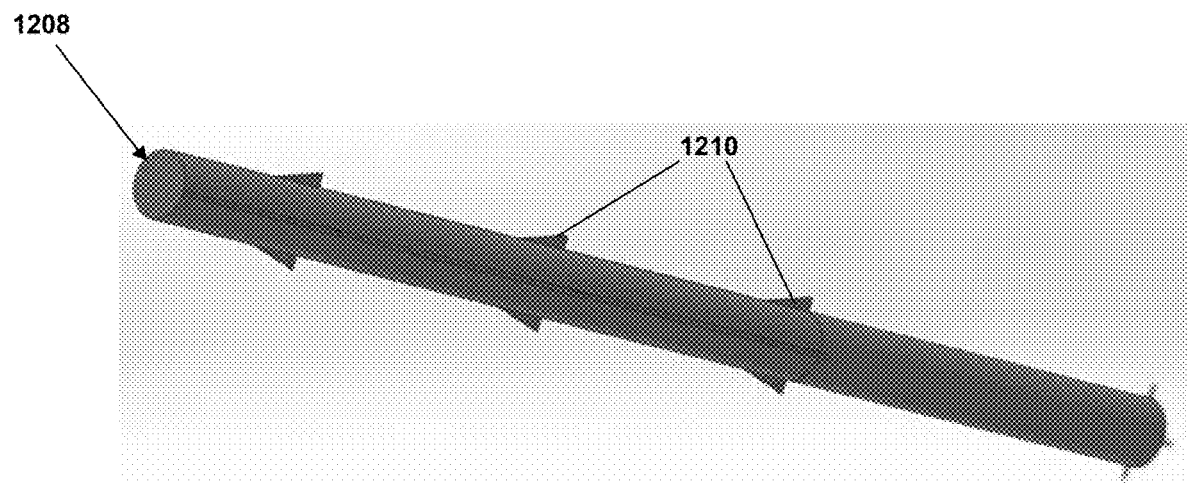
FIG. 37C is a dental occlusion or tension band tie body for the clasp of FIG. 37A, according to an embodiment.
Figure 38:
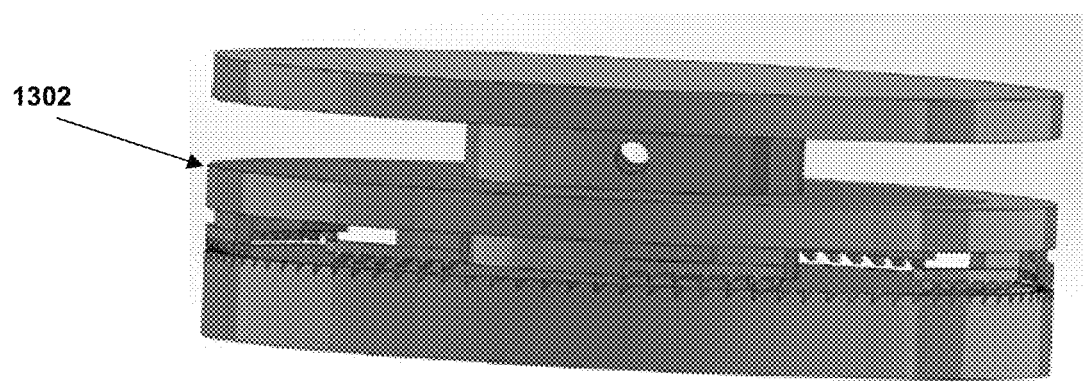
FIG. 38 is a perspective view of a clasp for a dental occlusion or tension band tie, according to an embodiment.

In another embodiment, referring to FIGS. 37A-37B, a clasp 1202 for a DO tie is depicted. In an embodiment, clasp 1204 comprises a housing 1204 and a receiving aperture 1206. In embodiments, clasp 1204, and particularly, internal elements of housing 1204 and receiving aperture 1206 are configured to interface with a body 1208, as depicted in FIG. 37C. Body 1208 comprises one or more locking projections 1210. As depicted, a set of locking projections 1210 can be spaced around the circumference of body 1208. Another set of locking projections 1210 can be positioned along the length of body 1208, and so on. The distance between locking projections 1210 determines the precision with which a surgeon or other user can "fine tune" the tightness of the DO tie. In embodiments, the sets of locking projections 1210 are closer along the length of body 1208 than depicted in FIG. 37C. In operation, when body 1208 is inserted to clasp 1202, one or more locking projections 1210 interfaces to receiving aperture 1206. For example, as depicted in FIG. 37B, a set of four locking projection apertures are positioned within receiving aperture 1206 to receive a corresponding set of four locking projections 1210. In other embodiments, fewer or additional locking projection apertures and corresponding locking projections 1210 can be utilized. According to an embodiment, the diameter of clasp 1202 can be 8 mm, with the internal diameter of receiving aperture 1206 being 1.6 mm. In embodiments, body 1208 has a diameter of 1 mm, with each of the locking projections extending 0.2 mm from the surface of body 1208. In other embodiments, other diameters for clasp 1202, body 1208, and locking projections 1210 are considered.

In another embodiment, referring to FIG. 28, a clasp 1302 for a DO tie is depicted. Clasp 1302 can be tightened to a body in a segmental or incremental fashion. In embodiments, a plurality of locking tabs or a high friction surface prevent loosening rotation to a body.

Figure 39A:
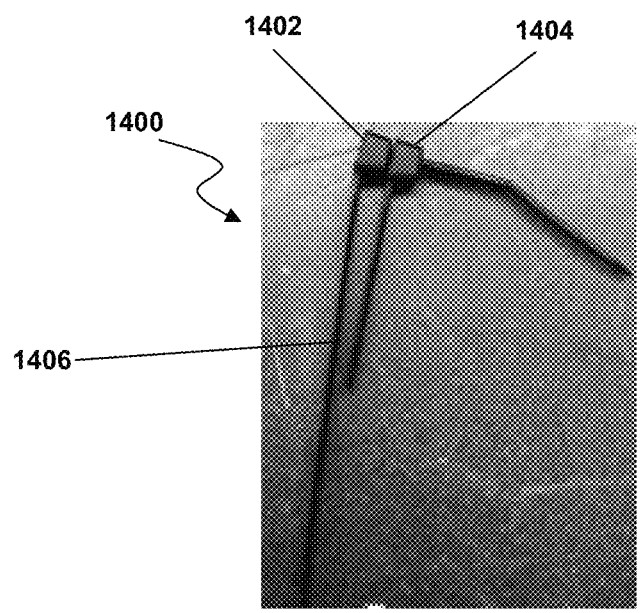
FIG. 39A is a perspective view of clasp for a dental occlusion or tension band tie having multiple receiving apertures, according to an embodiment.
Figure 39B:
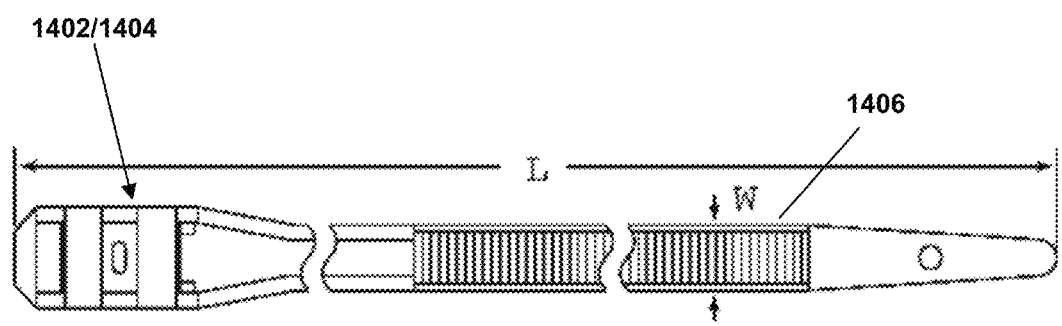
FIG. 39B is a side view diagram of the clasp of FIG. 39A, according to an embodiment.

In another embodiment, referring to FIGS. 39A-39B, DO tie 1400 is depicted. DO tie 1400 can be substantially similar to any of the aforementioned DO ties. In an embodiment, DO tie 1400 comprises a first clasp 1402, a second clasp 1404, and a body 1406. First clasp 1402 comprises a housing and receiving aperture similar to any of those described above. Second clasp 1404 likewise comprises a housing and receiving aperture similar to any of those described above. In embodiments, as depicted, first clasp 1402 is aligned with second clasp 1404 such that the respective receiving apertures of first clasp 1402 and second clasp 1404 allow for insertion or threading of body 1406 into both first clasp 1402 and second clasp 1404. Such alignment and locking by both first clasp 1402 and second clasp 1404 provides a secure engagement with the ribs of body 1406.

According to embodiments, when positioned on a patient or user, a clasp or portion of a body can be raised off the surface of the teeth intentionally so that a cutting device (e.g. a suture scissors) can be applied for easy removal of the DO tie or TB tie. For example, referring to FIG. 40A, a DO tie or TB tie 1500 is depicted. DO tie 1500 generally comprises clasp 1502 and body 1504. As depicted, clasp 1502 generally comprises bridge segment 1506 that is indented, crimped, or otherwise notched to create a space or gap for a cutting device. As depicted, bridge segment 1506 is curved, but can also comprise a wave or other non-linear shape. In other embodiments, body 1504 comprises bridge segment 1506. In still other embodiments, portions of bridge segment 1506 span both clasp 1502 and body 1504.

Figure 40A:
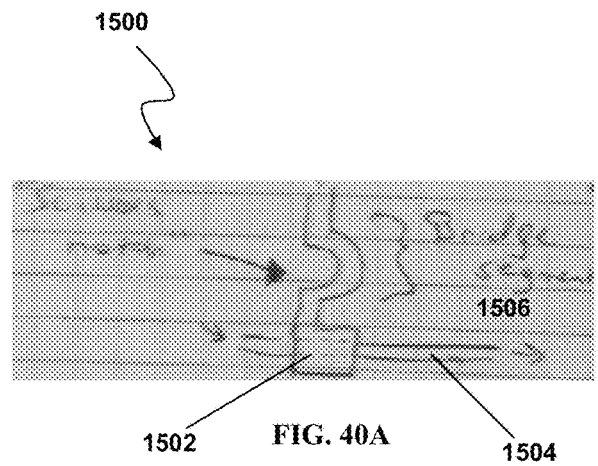
FIG. 40A is a side view of a dental occlusion or tension band tie including a bridge segment, according to an embodiment.
Figure 40B:
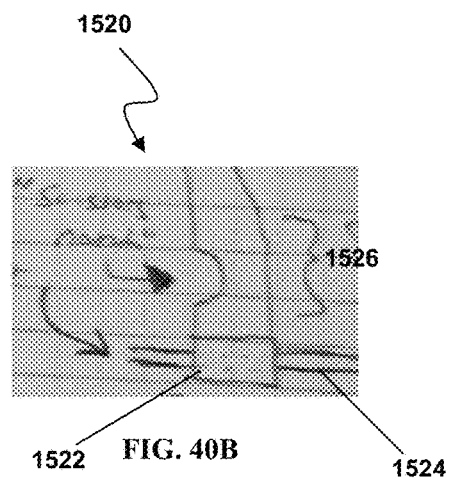
FIG. 40B is a side view of a dental occlusion or tension band tie including a bridge segment, according to an embodiment.

In another embodiment, referring to FIG. 40B, a DO tie or TB tie 1520 is depicted. DO tie 1520 generally comprises clasp 1522 and body 1524. As depicted, clasp 1522 generally comprises bridge segment 1526 that comprises a notch in the housing of clasp 1522. In other embodiments, body 1524 comprises bridge segment 1526. In still other embodiments, portions of bridge segment 1526 span both clasp 1522 and body 1524.

Figure 40C:
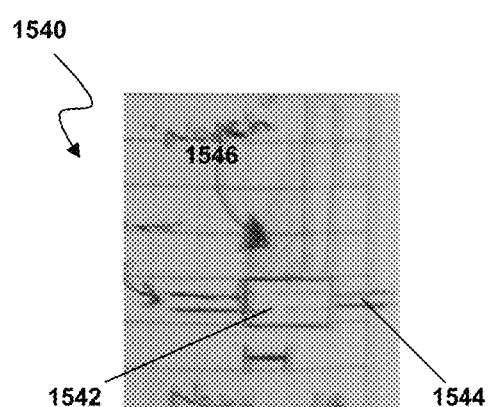
FIG. 40C is a side view a dental occlusion or tension band tie including a notch segment, according to an embodiment.

In another embodiment, referring to FIG. 40C, a DO tie or TB tie 1540 is depicted. For example, DO tie or TB tie 1540 can comprise an embodiment substantially similar to the dental occlusion or tension band of FIG. 34B. DO tie 1540 generally comprises clasp 1542 and body 1544. As depicted, clasp 1542 generally comprises bridge segment 1546 that comprises a notch in the housing of clasp 1542. In other embodiments, body 1544 comprises bridge segment 1546. In still other embodiments, portions of bridge segment 1546 span both clasp 1542 and body 1544. Bridge segment 1546, and particularly, the notch of bridge segment 1546 is created by securing a ribbed segment of body 1544 at a specified "notch width" from the tooth interface.

Figure 40D:
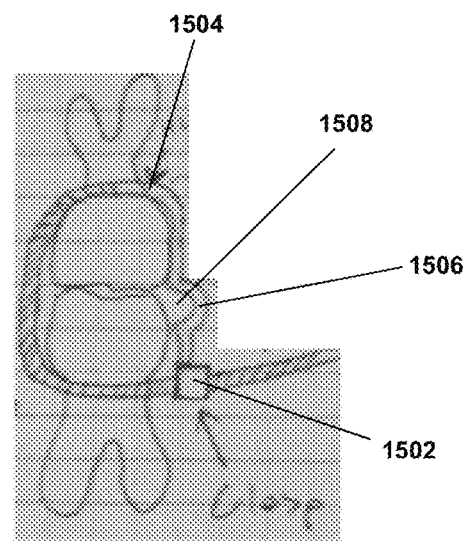
FIG. 40D is a side view of the dental occlusion or tension band tie of FIG. 40A operably coupled to teeth, according to an embodiment.

In operation, referring again to DO tie or TB tie 1500 and FIG. 40A and also FIG. 40D, when DO tie or TB tie 1500 is operably coupled to the teeth of a patient, a gap 1508 is created between the surface of the teeth and clasp 1502 and/or body 1504. A cutting device can be positioned proximate gap 1508 in order to sever DO tie or TB tie 1500 and remove DO tie or TB tie 1500 from the teeth. Similar gaps are created when embodiments of DO tie or TB tie 1520 and DO tie or TB tie 1540 are operably coupled to teeth.

In embodiments, clasps can be configured as "incompetent" or "partially competent" such that they are non-binding or non-locking or partially binding or partially locking. For example, an incompetent clasp embodiment can allow a surgeon or other user to fully apply the devices, yet loosen and adjust the devices (and particularly, the length of body in the clasp, if needed. In an embodiment, clasps can be configured with at least two levels of competence. For example, in a first example level, a moderate competence allows the device to hold gentle occlusion, particularly if at least one device is applied to each side of the jaw (left and right). In a second example level, a permanent competence rigidly secures the device for an extended period of time. For example, a permanent competence rigidly secures the device for 6 weeks. In other embodiments, a permanent competence rigidly secures the device for additional or fewer weeks. According to one embodiment, DO ties or TB ties are reinforced with a hemostat on the tail extending from the clasp, thereby providing a permanent competence.

According to an embodiment, a DO tie or TB tie can comprise multiple rib segments. For example, a first rib segment can be configured for moderate competence. A second rib segment can be configured for permanent competence. In embodiments, the DO tie or TB tie can comprise multiple clasps to interface to the multiple rib segments. For example, a first clasp can be configured for moderate competence and interface to the first rib segment configured for moderate competence. A second clasp can be configured for permanent competence and interface to the second rib segment configured for permanent competence. In other embodiments, a single clasp can interface to all of the rib segments. In still other embodiments, separate portions of a single clasp are configured to interface to the various rib segments.

Figure 41:
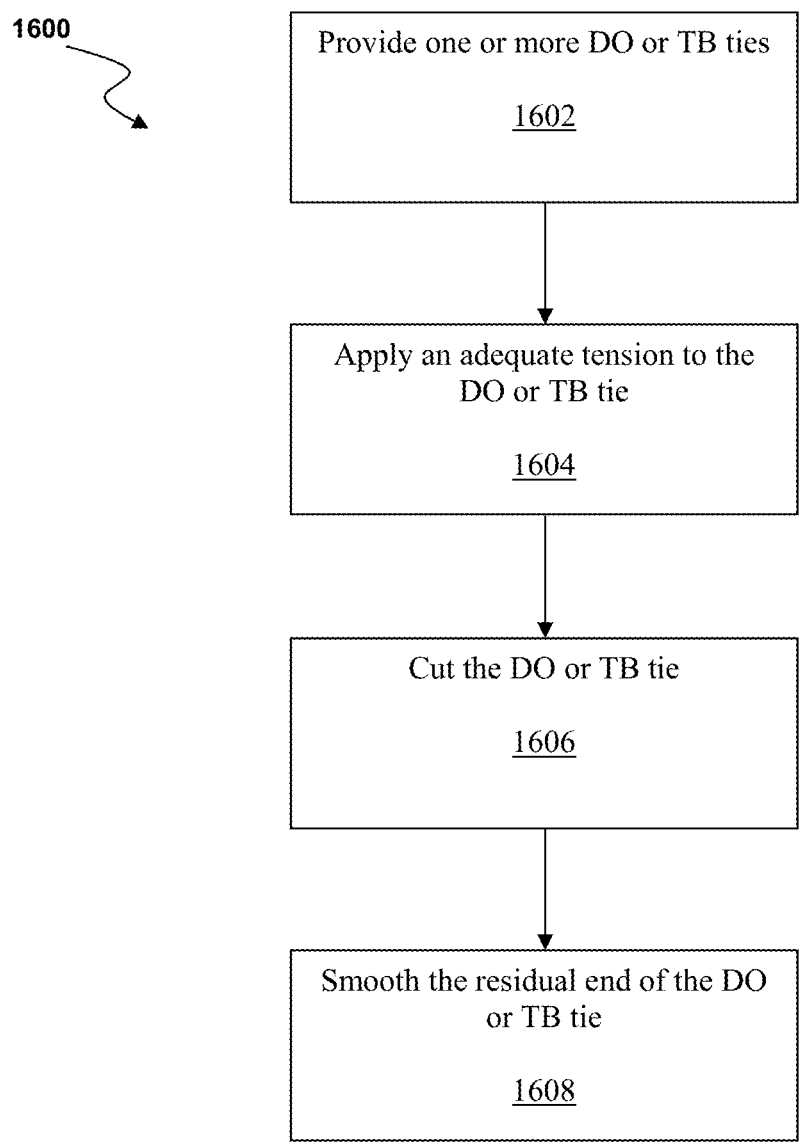
FIG. 41 is a flowchart of a method of providing a permanent competence dental occlusion or tension band tie, according to an embodiment.

Referring to FIG. 41, a method 1600 of providing a permanent competence DO or TB tie is depicted. At 1602, one or more DO or TB ties are provided. According to embodiments, a DO or TB tie can be threaded, flossed, or otherwise coupled to the jaw or teeth of the patient. At 1604, an adequate amount of tension is applied to the DO or TB tie. For example, the DO or TB tie or set of DO or TB ties can be tightened so that minimal space exists between the coupled teeth. In embodiments, minimal space likewise exists between the DO or TB and the tooth or teeth to which the DO or TB is coupled. At 1606, the DO or TB tie is cut. In embodiments, at 1606, the residual DO or TB tie that extends beyond the clasp is cut. For example, once the body of the DO or TB tie is threaded through the clasp, an excess residual portion of the tie will extend beyond an exiting side of the clasp. In other embodiments, other portions of the DO or TB tie are cut. At 1608, the residual end of the DO or TB tie is smoothed or blunted. Smoothing or blunting the residual end further provides comfort to the user, as any sharp or pointed edges of the residual or excess tie are removed. Moreover, removing any ability to retighten or otherwise adjust the excess tie provides a permanent competence. In embodiments, clasps can be reinforced at the time of cutting the residual tie. Such reinforcement can create clasps having a form of a vessel clip. A vessel clip can be applied and crimped as a "backstop" to an incompetent or competent clasp.

Any of the aforementioned embodiments of clasp designs are not mutually exclusive combinations of features; rather, embodiments of clasps can comprise a combination of different individual features selected from different individual embodiments, as understood by persons of ordinary skill in the art.

Figure 42:
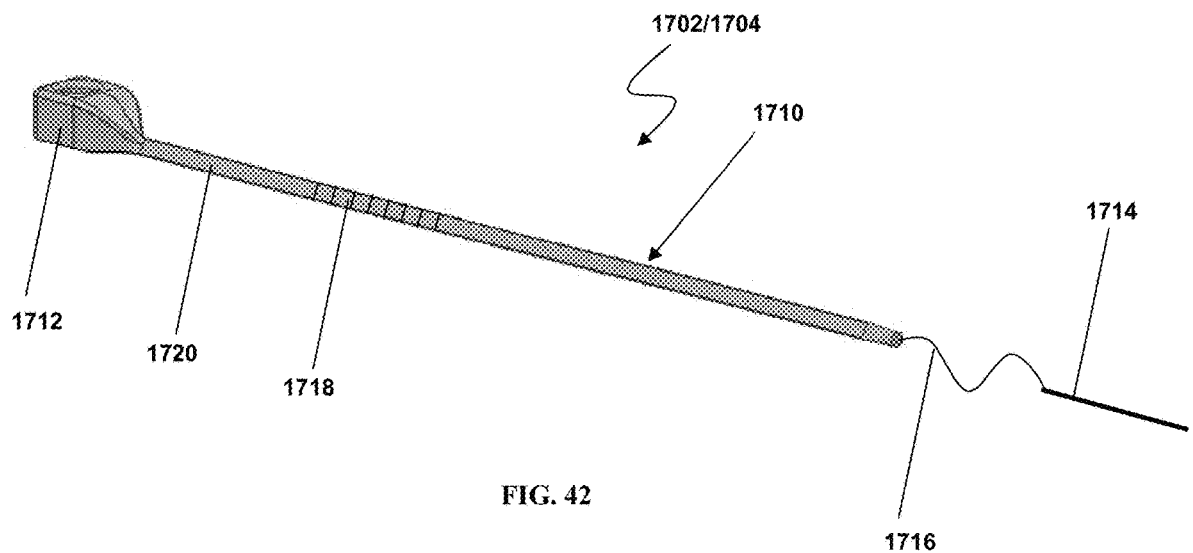
FIG. 42 is a perspective view of a dental occlusion or tension band tie, according to an embodiment.

In another embodiment, referring to FIG. 42, a DO tie 1702 or TB tie 1704 is depicted. DO tie 1702 and TB tie 1702 are substantially similar to any of the aforementioned DO ties or TB ties, respectively, with differences described herein. Embodiments include a maximal cross-section to traverse apical embrasures. Further, embodiments include an optimal cross-section to traverse apical embrasures. Embodiments include a maximal length for easy packaging, such as by linear orientation or coiled, in embodiments. In embodiments, devices include an optimal length for easy handling and manipulation by a user. In an embodiment, the devices 1702 and 1704 generally comprise an elongate body 1710 and a clasp 1712.

In an embodiment, body 1710 generally comprises a needle portion 1714, a thread portion 1716, a ribbed portion 1718, and a post-ribbed portion 1720. In embodiments, needle portion 1714 is substantially similar to any of the aforementioned needle portions, with differences described herein. In embodiments, needle portion 1714 comprises an optimal length for manual insertion such that no instrument is required. In other embodiments, needle portion 1714 comprises an optimal length for instrument application, such as hemostat or a needle driver. According to embodiments, needle portion 1714 can comprise a linear profile. In other embodiments, needle portion 1714 can comprise a curved or wavy profile.

In embodiments, thread portion 1716 is substantially similar to any of the aforementioned thread portions, with differences described herein. In embodiments, thread portion 1716 comprises an optimal length for handling such that thread portion 1716 does not tangle, or one end drops off the sterile field. In embodiments, thread portion 1716 further comprises an optimal length to have enough slack for placement in the mouth and clasp 1712 without limiting oral access for succeeding devices 1702 or 1704. According to embodiments, thread portion 1716 comprises an optimal radius to pass through embrasures without flossing out.

In embodiments, ribbed portion 1718 is substantially similar to any of the aforementioned ribbed portions, with differences described herein. In an embodiment, ribbed portion 1718 comprises a length to allow engagement of clasp 1712 yet allow an adequate gap between upper and lower dentition for fine tuning fracture reduction. According to embodiments, ribbed portion 1718 comprises an optimal cross-sectional geometry to engage an embrasure. In embodiments, ribbed portion 1718 comprises an optimal width to pass through, for example 95% of targeted embrasures. In embodiments, for example, incisor embrasures may not be utilized in embodiments of devices 1702 or 1704. In other embodiments, ribbed portion 1718 comprises a minimal width to have a secure purchase in an apical embrasure without flossing out. In embodiments, ribbed portion 1718 comprises ribs spaced apart at an optimal distance to allow for fine-tuning on a particular loop (refer, for example, to FIG. 9). For example, on a first section of ribbed portion 1718, ribs can be spaced apart at a larger distance. On a second section of ribbed portion 1718, ribs can be spaced apart at a smaller distance. In embodiments, distances between ribs are optimal for manufacturing, such as by machining, injection molding, etc.).

Post-ribbed portion 1720 comprises a length of body 1710 between ribbed portion 1718 and clasp 1712. According to an embodiment, post-ribbed portion 1720 comprises a maximal bend radius. In embodiments, post-ribbed portion 1720 is more flexible than other portions of body 1710. When applied, post-ribbed portion 1720 emerges from an apical embrasure and turns onto the face of the buccal surface of the teeth. According to embodiments, post-ribbed portion 1720 comprises a maximal length to allow for a tight bend radius of a fully-tightened clasp 1712. Other combinations of these and other portions can be arranged to form either or both of devices 1702 and 1704 in other embodiments.

Figure 43:
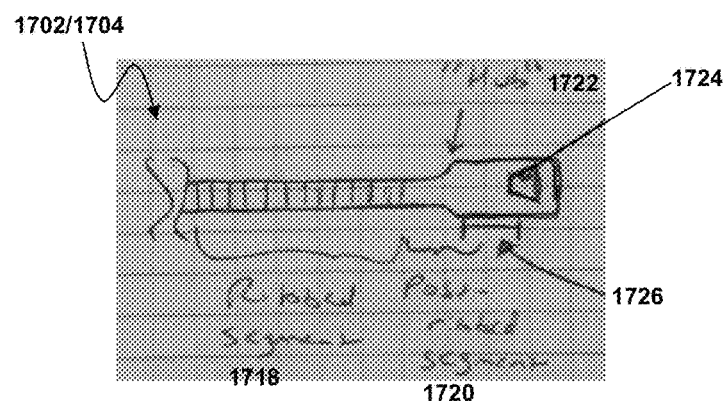
FIG. 43 is a top view of the dental occlusion or tension band tie of FIG. 42, according to an embodiment.

In an embodiment, referring to FIG. 43, post-ribbed portion 1720 can further comprise a hub 1722. Hub 1722 comprise the location of widening that touches the gingiva once DO tie 1702 and/or TB tie 1704 is fully inserted. According to an embodiment, hub 1722 widens a short distance in front of clasp 1712 to place clasp 1712 at a predetermined position. In an embodiment, hub 1722 widens body 1710 in front of clasp 1712 a few millimeters in front of clasp 1712. In other embodiments, the distance of widening is greater or less than a few millimeters. Accordingly, a preset length 1726 standardizes the distance from hub 1722 to receiving aperture 1724 once DO tie 1702 and/or TB tie 1704 is fully inserted.

Body 1710 can have a unitary construction in an embodiment such that needle portion 1714, thread portion 1716, ribbed portion 1718, and post-ribbed portion 1720 are formed of a single piece of material, or one or more of the portions 1714, 1716, 1718, and/or 1720 can be separately formed of the same or a different material and coupled with the other portions. Similarly, in embodiments, clasp 1712 can be of unitary construction with one, some or all of portions 1714, 1716, 1718, and/or 1720 or clasp 1712 can be separately formed and coupled therewith, as will be described. Couplings between one or more of clasp 1712 and portions 1714, 1716, 1718, and 1720 can be removable or fixed, and can vary in various embodiments of DO ties 1702 and/or TB ties 1704.

Clasp 1712 is substantially similar to any of the aforementioned clasps, with differences described herein. Clasp 1712 comprises a receiving aperture 1724 having a width to accept body 1710 or portions of body 1710 as described. In an embodiment, receiving aperture 1724 of clasp 1712 is 0.30 mm wider than ribbed portion 1718.

In embodiments, body 1710 and/or clasp 1712 can be made of any suitable biocompatible polymer. For example, any suitable biocompatible polymer comprising an appropriate tensile strength can be utilized. In other embodiments, any suitable biocompatible polymer comprising an appropriate elasticity can be utilized. In embodiments, portions of body 1710 and/or clasp 1712 have variable material properties depending on the section. For example, a thread-like polymer can undergo a thermal or cross-linking treatment in needle portion 1714 to create an adequate rigidity.

In another embodiments, body 1710 and/or clasp 1712 can be made of any suitable metal or alloy. For example, any suitable biocompatible metal or allow comprising an appropriate tensile strength can be utilized. In other embodiments, any suitable biocompatible metal or allow comprising an appropriate elasticity can be utilized. In embodiments, portions of body 1710 and/or clasp 1712 have variable material properties depending on the section. For example, a flexible ribbon-like segment of alloy can bend easily, but needle portion 1714 made of the same alloy can be configured to be rigid.

Figure 44:
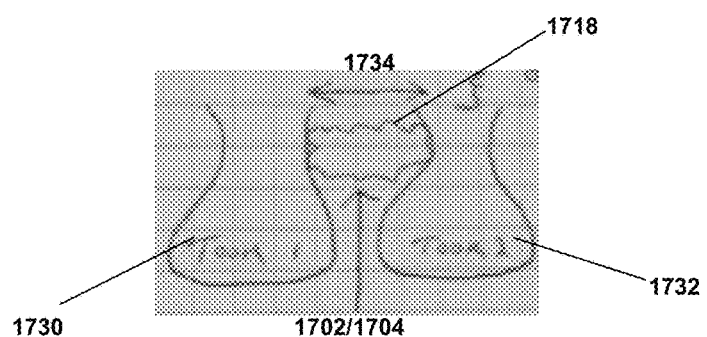
FIG. 44 is a diagram of a dental occlusion or tension band tie in contact with two teeth, according to an embodiment.

According to embodiments, ribbed portion 1718 further comprises a dental engagement portion adapted to interface to the teeth. Ribbed portion 1718 is configured to be minimally compressible across device 1702/1704. For example, referring to FIG. 44, device 1702/1704 is positioned in between a first tooth 1730 and a second tooth 1732. Along axis 1734, ribbed portion 1718 is configured to be minimally compressible. In this axis, as device 1702/1704, and particularly, ribbed portion 1718, decreases in compressibility, device 1702/1704 becomes less likely to floss out of teeth 1730 and 1732.

Figure 45:
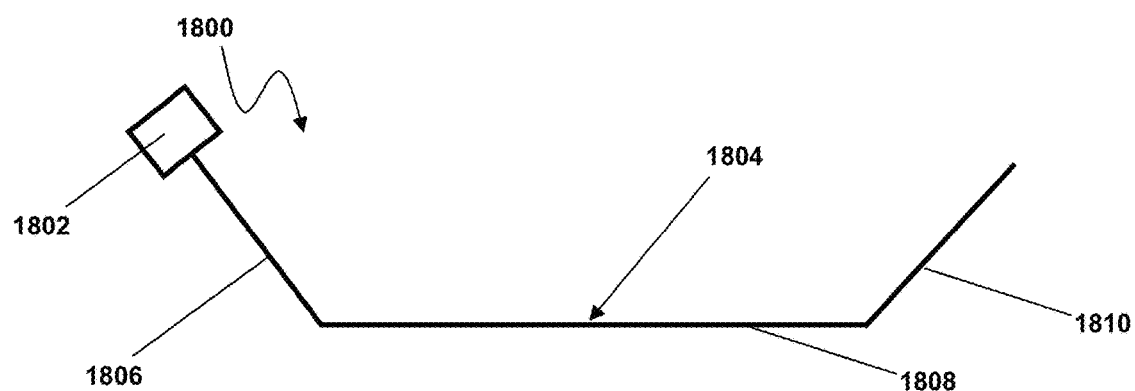
FIG. 45 is a cross-sectional view of a dental occlusion or tension band tie, according to an embodiment.

In another embodiment, referring to FIG. 45, a dental occlusion or tension band tie 1800 is depicted. DO tie or TB tie 1800 generally comprises clasp 1802 and body 1804, each of which are substantially similar to corresponding clasps and bodies described above. Body 1804 further comprises a first angled portion 1806, main portion 1808, and a second angled portion 1810. As depicted, main portion 1808 operably couples first angled portion 1806 and second angled portion 1810. Each angled portion 1806 and 1810 projects from main portion 1808 at an angle. In other embodiments, the length and angle of the respective portions can vary, as will be readily appreciated by one skilled in the art.

During installation or coupling to the teeth of a patient, DO tie or TB tie 1800 will tend to flatten when rotated through a dental embrasure due to the angles of first angled portion 1806 and second angled portion 1810 relative to main portion 1808. Such a configuration assists the user in multiple ways. For example, DO tie or TB tie 1800 readily traverses the V-shaped space between the gingival papilla and the teeth. Further, dental occlusion or tension band tie 1800 compresses the papilla gently as the cross-section changes at the insertion point from, for example, second angled portion 1810 to main portion 1808, or from main portion 1808 to first angled portion 1806. Moreover, DO tie or TB tie 1800 is strengthened in the transverse axis.

Figure 46:
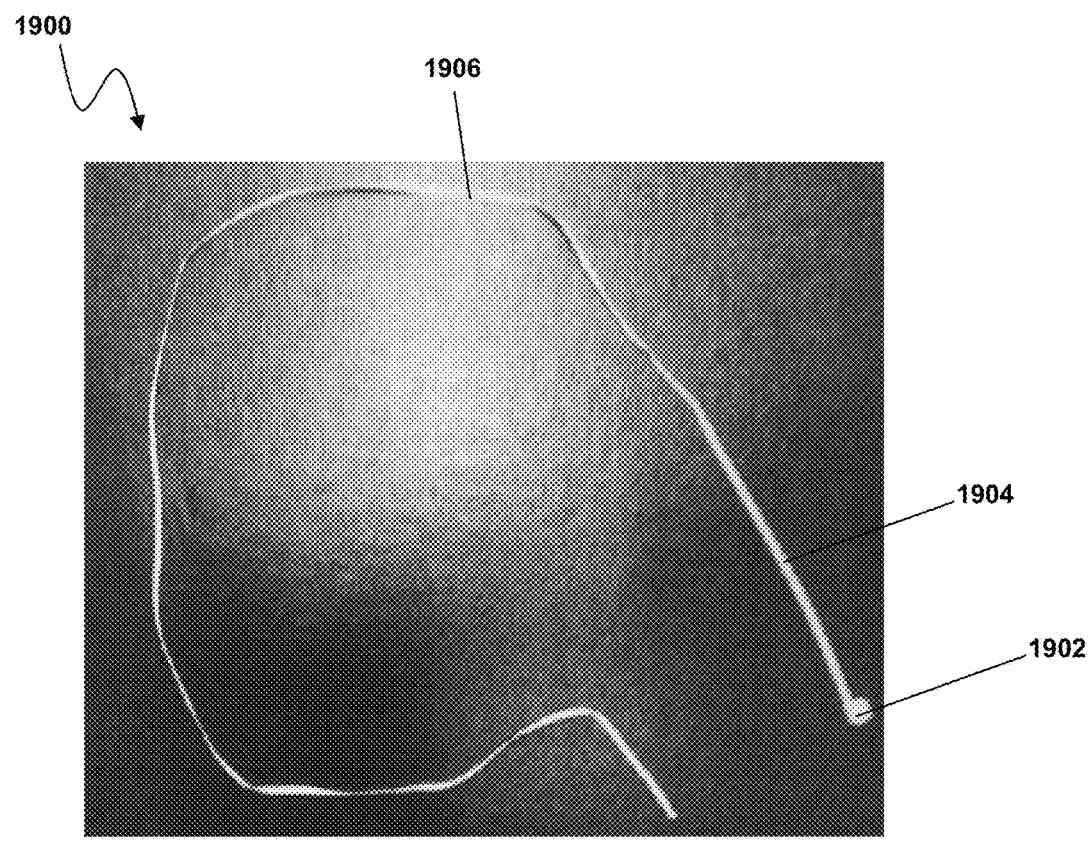
FIG. 46 is a picture of a "floss-in" dental occlusion or tension band tie, according to an embodiment.

According to another embodiment, a "floss-in" dental occlusion or tension band tie 1900 is depicted in FIG. 46. In embodiments, DO tie or TB tie 1900 is "instrument free" in that DO tie or TB tie 1900 can be applied to a patient without any instruments. DO tie or TB tie 1900 generally comprises clasp 1902, body 1904, and floss portion 1906.

Clasp 1902 is substantially similar to any of the aforementioned clasps and comprises a housing and a receiving aperture configured to receive floss portion 1906 and body 1904 and operably couple to body 1904.

Body 1904 extends from clasp 1902 and is substantially similar to any of the aforementioned bodies. As such, body 1904 comprises a ribbed portion configured to interface or otherwise couple to clasp 1902.

Floss portion 1906 extends from body 1904 and comprises an elongated, thin thread-like segment without a needle or rigid portion extending therefrom. In embodiments, floss portion 1906 is therefore substantially similar to any of the aforementioned thread portions. In operation, floss portion 1906 can be manually applied to slide between the teeth, similar to standard dental floss. When floss portion 1906 is in an apical embrasure, DO tie or TB tie 1900 can be advanced so the ribbed portion of body 1904 is positioned in the apical embrasure. The ribbed portion of body 1904 can be operably coupled to clasp 1902 to secure DO tie or TB tie 1900.

Figure 47:
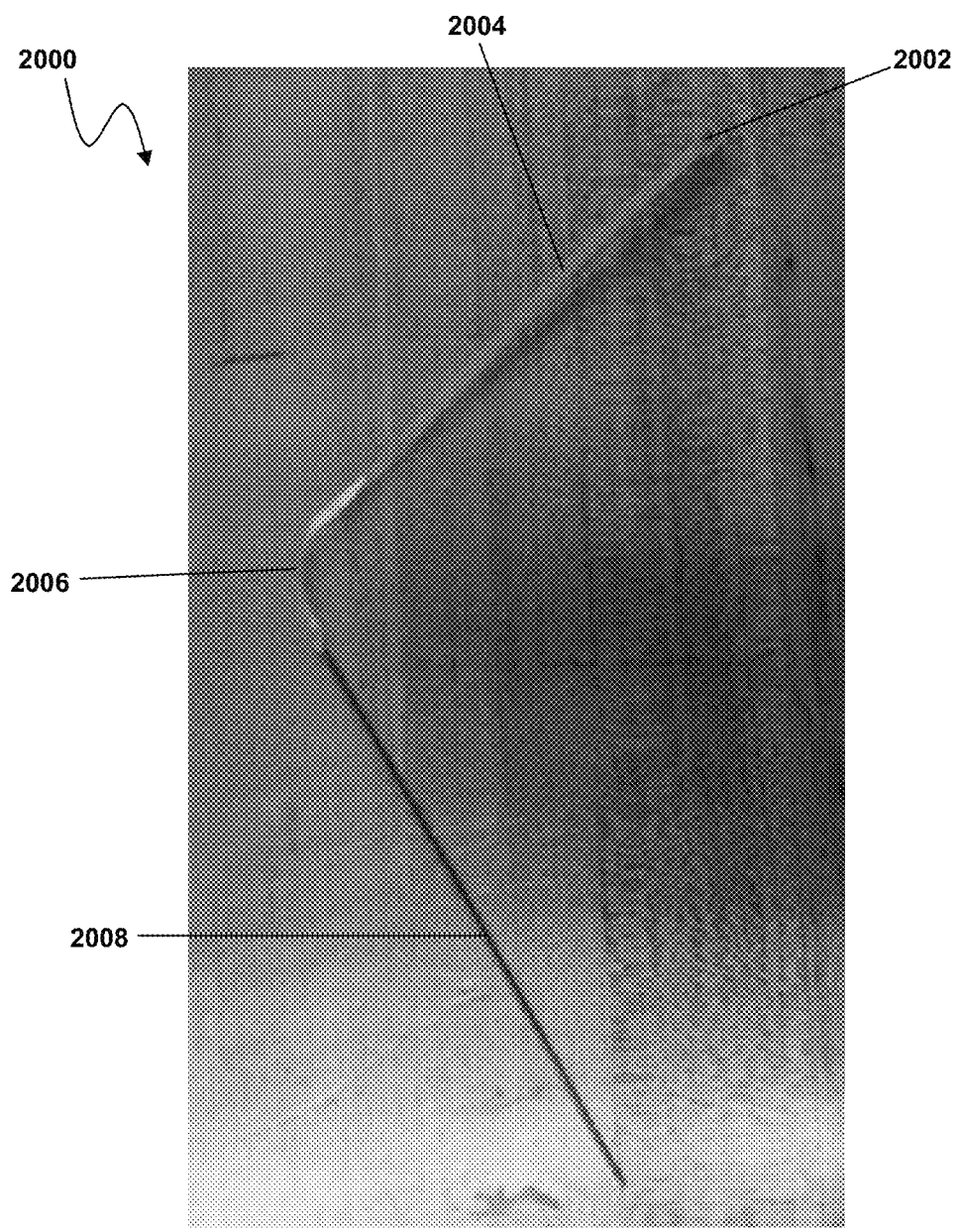
FIG. 47 is a picture of a "floss-in" dental occlusion or tension band tie, according to an embodiment.

Referring to FIG. 47, in another embodiment of a "floss-in" dental occlusion or tension band tie 2000, DO tie or TB tie 2000 generally comprises clasp 2002, body 2004, floss portion 2006, and handle 2008. Clasp 2002, body 2004, and floss portion 2006 are substantially similar to the corresponding components of DO tie or TB tie 1900 as depicted in FIG. 47. In embodiments, handle 2008 comprises a rigid or semi-rigid frame or housing for ease of gripping by the user. In embodiments, handle 2008 is substantially similar to body 2004 and further comprises a ribbed portion configured to interface or otherwise couple to clasp 2002. In another embodiment, handle 2008 comprises a rigid needle allowing for both floss-in application or "needle-in" application.

According to embodiments, utilities, tools, or add-on features can be utilized with any of the aforementioned DO ties or TB ties. Embodiments related to devices, systems, kits and methods for achieving maxillo-mandibular fixation (MMF) can further include any of the following utilities, tools, or add-on features or components of the following utilities, tools, or add-on features.

Combined Cheek Refractor and Tie Organizer

Embodiments relate to cheek retractors comprising at least one tie organizer to maintain an expansive opening of the lips and cheeks while facilitating placement of e.g., dental occlusion or tension band ties during oral surgery or other treatment.

In an embodiment, a cheek retractor comprises a flexible frame comprising at least one supporting member; first and second tabs coupled to the at least one supporting member, wherein each tab comprises a channel; and first and second tie organizers formed in the first and second tabs, respectively, and comprising a plurality of apertures configured to selectively receive at least one dental tie device.

In an embodiment, a method comprises providing a cheek retractor comprising first and second tabs, wherein each of the first and second tabs comprises a tie organizer; forming a tie organizer in each of the first and second tabs by forming a plurality of apertures in each of the first and second tabs, the plurality of apertures being configured to selectively receive at least one dental tie device.

Embodiments relate to a cheek retractor configured to maintain an expansive opening of the lips and cheeks while facilitating oral surgery or another procedure, such as cheek retractors comprising at least one tie organizer portion configured to temporarily secure and organize one or more ties or other devices during a procedure, the tie organizer comprising at least one of a detachable segment, a pre-attached tie, a removable feature and/or an external ledge or tray to aid in tie application and fixation.

In an embodiment, a cheek retractor comprises a flexible frame comprising at least one supporting member; first and second tabs coupled to the at least one supporting member, wherein each tab comprises a channel; and first and second tie organizers removably coupled to the first and second tabs, respectively, and comprising a plurality of apertures configured to selectively receive at least one dental tie device.

In an embodiment, a cheek retractor comprises a flexible frame comprising at least one supporting member; first and second tabs coupled to the at least one supporting member, wherein each tab comprises a channel; and a plurality of apertures removably coupled to a top surface of the first and second tabs to form a first and second tie organizer, respectively, the plurality of apertures configured to selectively receive at least one dental tie device.

In an embodiment, a method comprises providing a cheek retractor comprising first and second tabs, wherein each of the first and second tabs comprises a tie organizer; forming a tie organizer for removable detachment from each of the first and second tabs; and forming a plurality of apertures in the tie organizer, the plurality of aperture each configured for removable detachment from each of the first and second tabs.

Embodiments relate to devices and methods for facilitating oral surgery. One embodiment comprises a cheek retractor configured to maintain an expansive opening of the lips and cheeks while facilitating oral surgery or another procedure, the cheek retractor comprising at least one tie organizer portion configured to temporarily secure and organize one or more ties or other devices during a procedure, the tie organizer comprising at least one of a detachable segment, a pre-attached tie, a removable feature and/or an external ledge or tray to aid in tie application and fixation. Such a cheek retractor and tie organizer can make application of occlusion and/or tension band ties, or other devices, more convenient and efficient. Though referred to herein generally as a cheek retractor, cheek retractor 2100 can comprise other retractor devices that can be used to maintain an expansive opening of an anatomical feature of the body such as an eye, ear, vagina, anus or other feature in various embodiments, and use of the term cheek refractor is not to be considered limiting to any particular embodiment or with respect to the claims.

Figure 48:
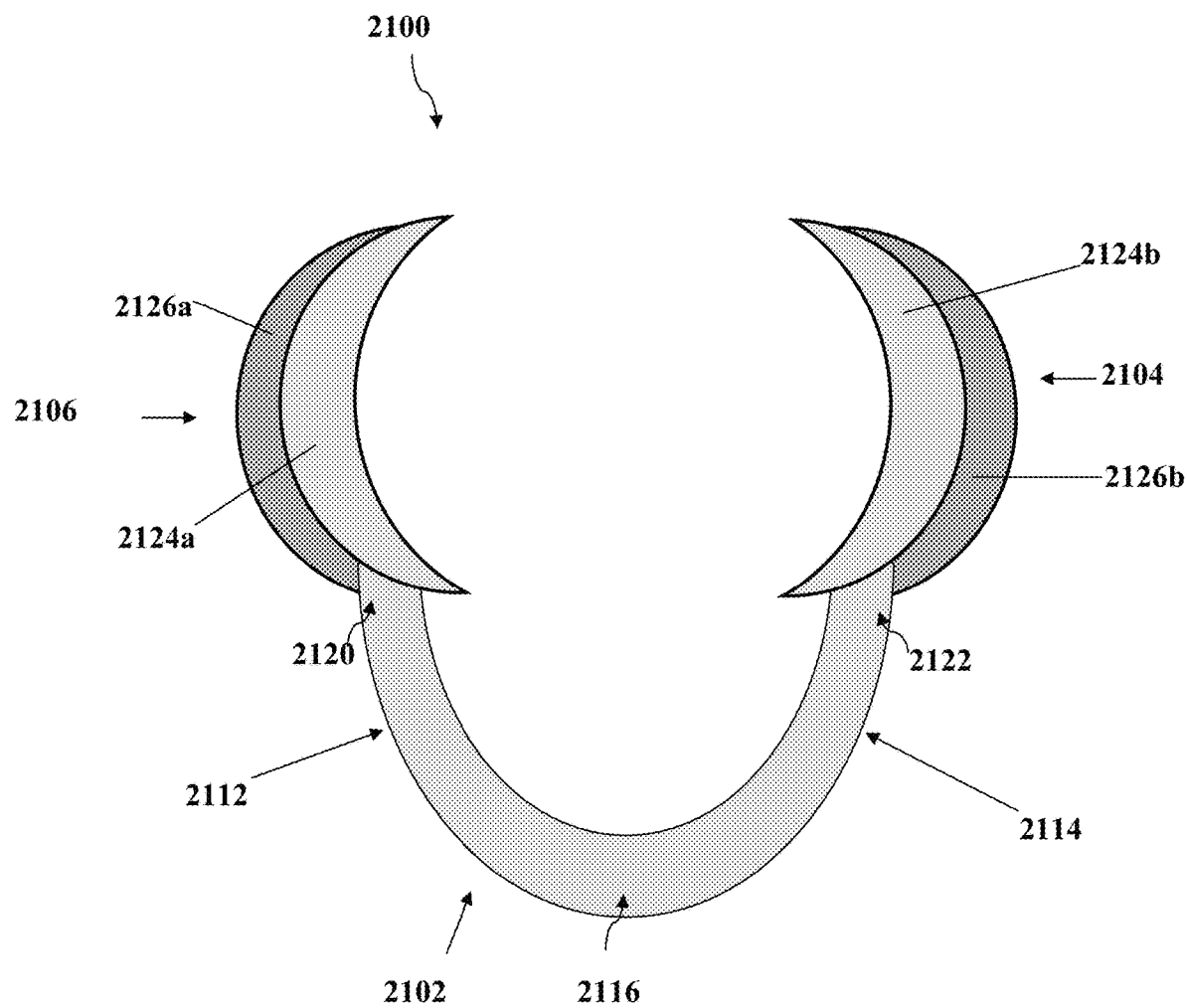
FIG. 48 depicts a front view of a cheek refractor.

Referring to FIG. 48, a cheek retractor 2100 comprises a flexible frame 2102, and a first and second tab 2104, 2106 for partial insertion into the oral cavity. In embodiments, frame 2102 can be generally u-shaped and comprise two supporting members 2112, 2114 that are joined at juncture 2116 to adjust the dimensions of a cross-sectional area of u-shaped frame 2102. Frame 102 can comprise an elastic material (e.g., polypropylene, polyethylene, steel, aluminum, etc.) to allow supporting members 2112, 2114 to return to their original shape when no pressure (e.g., compression or expansion) is applied. The elasticity of frame 2102 also allows for independent movement of supporting members 2112, 2114 and first and second tab 2104, 2106. For example, each tab 104 and 106 can be individually adjusted or inserted relative to the surgical requirement.

In embodiments, first and second tabs 2104, 2106 can be coupled to supporting members 2112, 2114, respectively, via junctures 2120, 2122, whereby supporting members 2112, 2114 can be configured to independently control the movement of tabs 2104, 2106. The first and second tabs 2104, 2106 can be generally of semicircular shape (e.g., crescent-shaped) but may vary in size and shape. Each tab 2104 and 2106 can comprise a top surface 2124a, 2124b and a bottom surface 2126a, 2126b such that a channel can be formed between top surfaces 2124a, 2124b and bottom surfaces 2126a, 2126b of each tab 2104, 2106. First and second tabs 2104, 2106 can be formed, such as curved, to more easily and/or comfortably accommodate a patient's cheeks, lips, or other tissue when in use. The channel of each tab 2104, 2106 can be configured to fit a patient's lips and cheeks, whereby the dimensions of each channel can be sized in proportion to a patient's anatomical geometries. The top surfaces 2124a-b of each tab 2104, 2106 can be configured to engage extraoral tissue of a patient's cheeks and lips, whereby the bottom surfaces 2126a-b can be configured to engage the intraoral tissue of a patient's lips and cheeks. The anatomical engagement of first and second tabs 2104, 2106 following insertion allows for an expansive opening of a patient's oral cavity to aid in oral surgery or other treatments.

Figure 49:
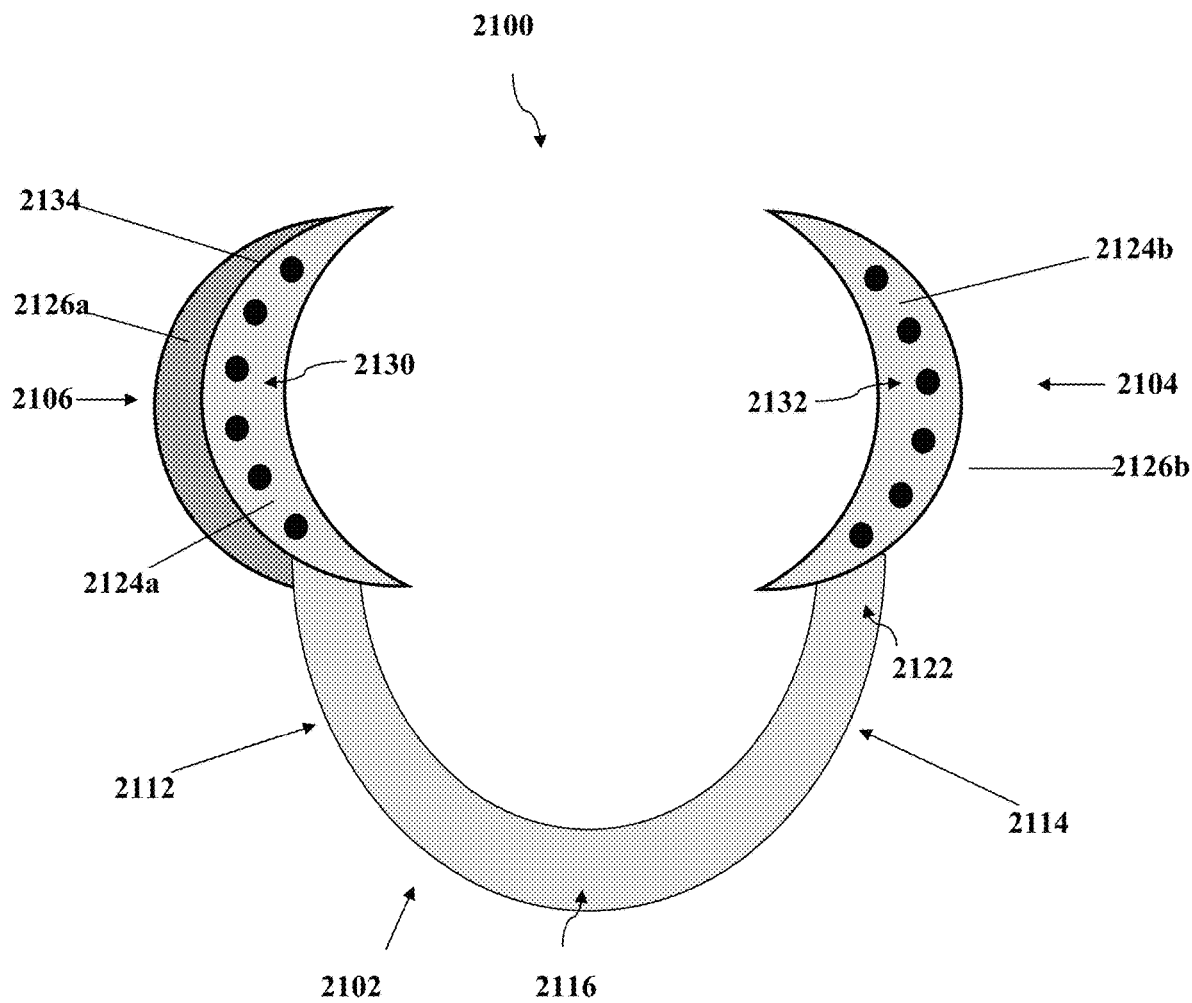
FIG. 49 depicts a front view of a cheek retractor and tie organizer, according to an embodiment.

Referring to FIG. 49, a front view of a cheek retractor 2100 comprising first and second tie organizers 2130, 2132 is shown according to an embodiment. In embodiments, the first and second tie organizers 2130, 2132 can be fixedly coupled to or formed in or on the first and second tabs 2104, 2106 to secure and organize materials associated with oral surgery or other treatments, where those materials can include dental ties and/or other suitable occlusion or surgical devices, such as wires, sutures, threads and the like. For example, the first and second tie organizers 2130, 2132, for example, can be used to facilitate the arrangement of dental occlusion ties, tension band ties, or other materials used during maxillo-manidibular fixation.

Figure 50:
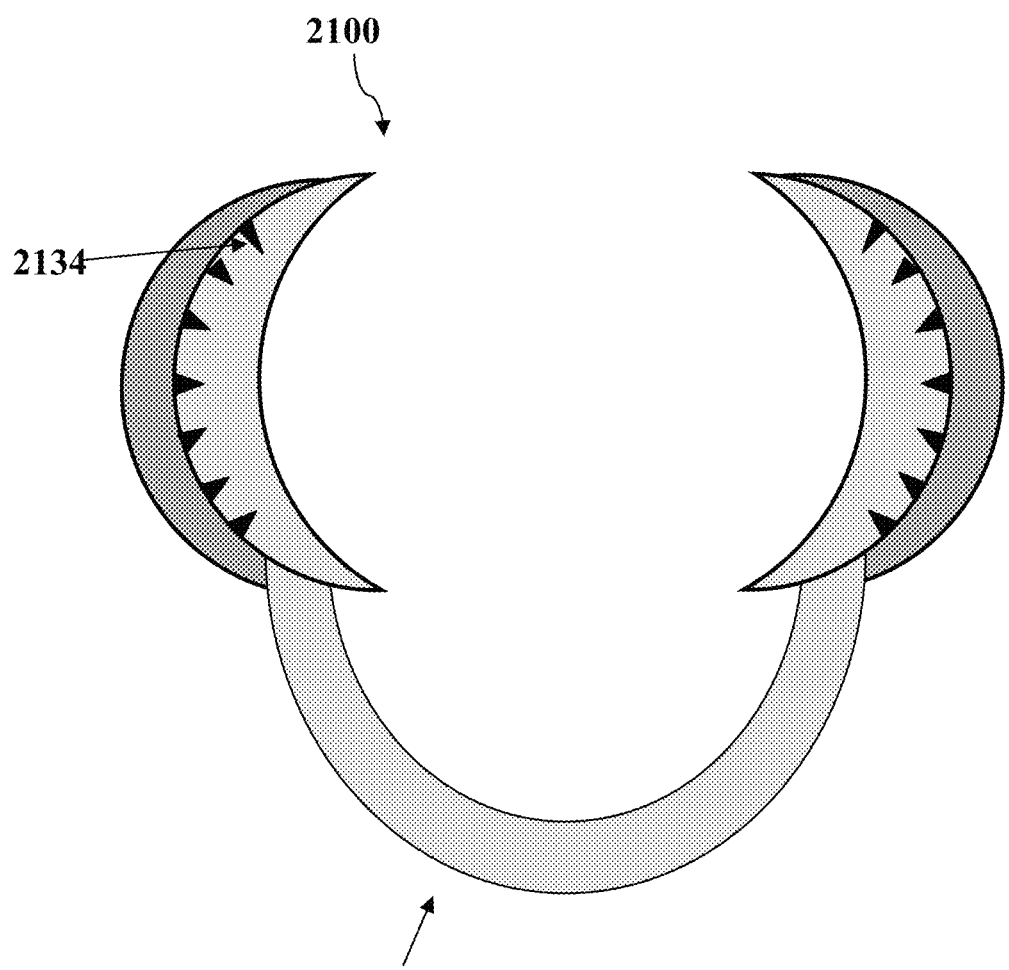
FIG. 50 depicts a front view of a cheek retractor and tie organizer, according to an embodiment.

In embodiments, each tie organizer 2130, 2132 comprises a plurality of notch elements or apertures 2134 arranged on top surfaces 2124a, 2124b of tabs 2104, 2106. In example embodiments, each tie organizer 2130, 2132 can comprise at least five notch elements or apertures (generally, "apertures") 2134, however, in other embodiments each tie organizer 2130, 2132 can comprise as few as two or as many as eight apertures 2134. In other embodiments, the plurality of apertures 2134 can be arranged along an inner (not shown in FIG. 49) or outer edge of the top surfaces 2124a, 2124b, or in other suitable configurations. The apertures 2134 can be configured to receive tie threads or other thread-like materials such as sutures that can be individually placed within each aperture 2134. In embodiments, the cross-sectional shape of the apertures 2134 can be generally circular or oval. In other embodiments, apertures 2134 can comprise notches having a generally triangular cross-sectional shape (FIG. 50), or key-hole shape, to, e.g., accommodate the use of wider thread-like materials. In still other embodiments, a single cheek retractor 2100 can comprise apertures 2134 having different configurations, e.g., at least one circular aperture and at least one notch-like aperture. The dimensions, arrangement, placement and shapes of apertures 2134 may vary according to material sizes to prevent loosening or premature release of the materials from apertures 2134. For example, dental ties are generally larger in size than materials such as sutures and thus require increased dimensional geometries of aperture 2134 cross-sections or configurations. As such, cheek retractor 2100 and tie organizers 2130, 2132 can be customized specific to a particular use or application.

Referring to FIGS. 51A-52B, a front view of a cheek retractor 2100 comprising first and second tie organizers 2210a, 2210b is shown according to an embodiment. In embodiments, the first and second tie organizers 2210a, 2210b can be removably coupled to top surfaces 2124a, 2124b of first and second tabs 2104, 2106 to allow for independent detachment of tie organizers 2210a, 2210b. In embodiments, first and second tie organizers 2210a, 2210b can comprise a plurality of apertures 2134 configured to selectively receive a dental tie device or other surgical device. In other embodiments, first and second tie organizers 2210a, 2210b can be configured as one unitary body for removal or insertion into a coupling mechanism 2213 formed in or on top surfaces 2124a, 2124b (FIG. 51B).

The detachable feature of first and second tie organizers 2210a, 2210b can provide a user with the ability to facilitate placement of multiple dental tie devices or other suitable surgical devices simultaneously. The mechanical coupling of first and second tie organizers 2210a, 2210b to first and second tabs 2104, 2106 can vary according to embodiments. For example, coupling mechanism 2213 can be configured as a grooved channel (not shown in FIGS. 51A-51C) for slidable engagement of tie organizers 2210a, 2210b into the grooved channels of top surfaces 2124a, 2124b. In other example embodiments, coupling mechanism 2213 can be configured as a slotted channel (not shown in FIGS. 51A-51C) formed in top surfaces 2124a, 2124b for snap engagement of first and second tie organizers 2210a, 2210b into the slotted channels. The provided example embodiments, however, are for illustration purposes only and are not intended to limit the scope of the invention.

As depicted in FIG. 51C, tie organizers 2210a, 2210b of first and second tabs 2104, 2106 can further comprise at least one pre-wound coil 2218 that can be removably coupled to at least one of the plurality of apertures 2134 or to cheek retractor 2100. The pre-wound coil 2218 can be pre-coupled or removably attached to tie organizers 2210a, 2210b and comprise a tie, wire or other suitable material configured in a generally circular or other compressed arrangement to provide a user with the ability to release a desired quantity of material as needed during application. Pre-wound coil 2218 can comprise a pull-tab or other release mechanism to facilitate unwinding of the material to a desired length. In other embodiments, pre-wound coil 2218 can be provided as a separate component or can be removably coupled to top or bottom surfaces 2124a-b, 2126a-b within the channel of first and second tabs 2104, 2106.

In still other embodiments, tie organizers 2210a, 2210b can comprise a plurality of pre-wired apertures 2134, whereby the pre-wired material can be configured to form a knotted loop or other configuration around each of the apertures 2134 to secure attachment of the material to apertures 2134. The residual end of each of the pre-wired material can extend horizontally or longitudinally from each of the plurality of apertures 2134 once the knotted loop has been formed.

In use, for example, pre-wound coil 2218 or the pre-wired aperture can be used as an anchor for a dental tie or other surgical device while the device is being secured within a dental embrasure. The use of pre-wound coil 2218 or pre-wired aperture can also assist with organization and placement of materials such as dental ties, particularly when multiple ones are to be applied Referring to FIGS. 52A and 52B, first and second tie organizers 2210a, 2210b each can comprise upper and lower segmented portions 2214a-b, 2216a-b that are configured to define a body member of tie organizers 2210a, 2210b. In embodiments, each of the segmented portions 2214a-b, 2216a-b can comprise at least one aperture 2134. Upper and lower segmented portions 2214a-b, 2216a-b each can comprise a corresponding coupling feature that is configured to facilitate secure attachment of the segmented portions 2214a-b, 2216a-b to one another and to coupling mechanism 2213 of top surfaces 2124a, 2124b.

In embodiments, each of the segmented portions 2214a-b, 2216a-b, or a portion thereof, such as a portion comprising a single aperture 2134, can be individually detached for insertion into the oral cavity, where that portion can secure engagement of a clasp to a dental occlusion or tension band tie or other suitable material (FIG. 52B). For example, during maxillo-mandibular fixation, each upper and lower segmented portion 2214a-b, 2216a-b can be removed for placement on a lower or upper dentition. Once a tie thread or material is looped through an embrasure, a loose end of the thread or material is inserted into at least one of the plurality of apertures 2134 and pulled to secure engagement of the clasp to the tie thread. The upper and lower segmented portions 2214a-b, 2216a-b can be detached for varied placement, e.g., internal or external of the oral cavity, to assist in organizing materials and for improved usability during facilitation of oral surgery or other treatments. Segmented portions 2214a-b, 2216a-b can also be used to provide a controlled tension on sequentially placed ties threads or materials.

Figure 53A:
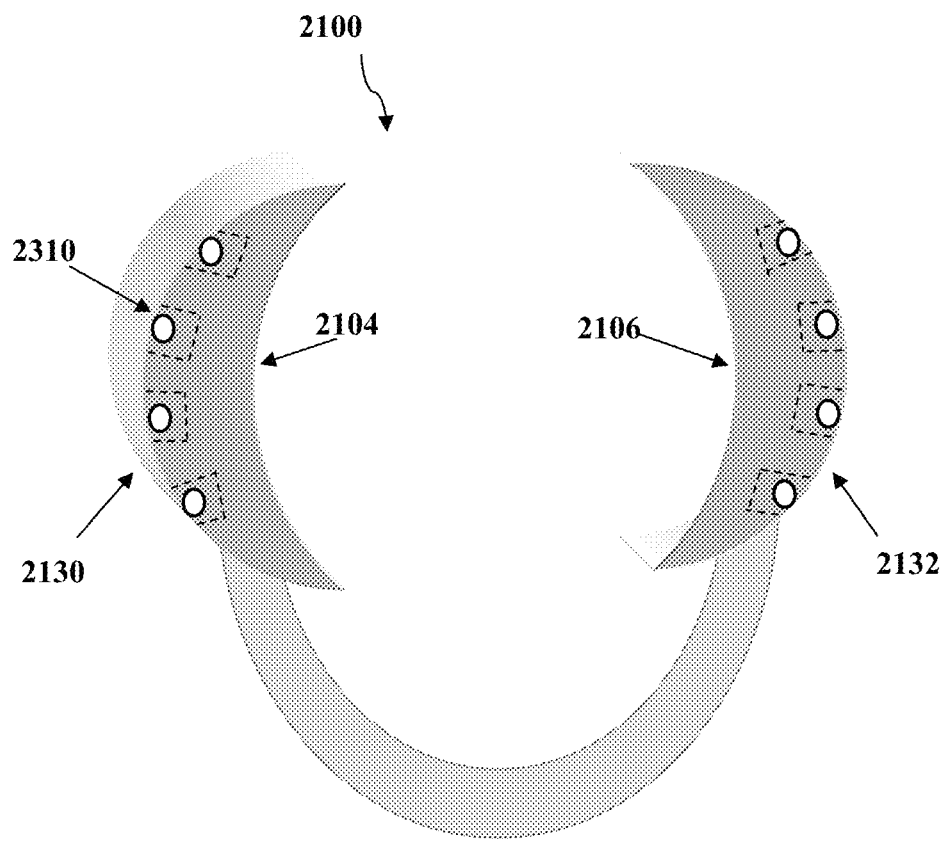
FIG. 53A depicts a front view of a cheek refractor and tie organizer, according to an embodiment.
Figure 53B:
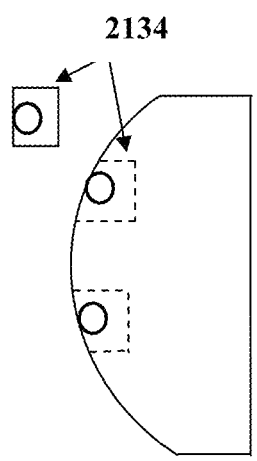
FIG. 53B depicts a front view of a tie organizer, according to an embodiment.

Referring to FIGS. 53A and 53B, top surfaces 2124a, 124b of first and second tabs 2104, 2106 can further comprise at least three apertures 2310 that can be removably coupled to top surfaces 2124a, 2124b. Each of the at least three apertures 2310 can be configured for individual detachment upon insertion of a tie thread or other suitable material into apertures 2310. For example, once a tie thread has been inserted into at least one of apertures 2310, aperture 2310 can be detached to secure a fixed position along a tie or other material, or can be detached for slidable engagement along a tie thread or other material. In other embodiments, each of the at least three apertures 2310 can be configured to form a clasp that engages with a ribbed segment of a tie thread or other suitable material or to secure engagement of a clasp to a tie thread or other suitable material. In embodiments, the geometrical design of the clasp can vary, whereby the clasp can comprise a generally rectangular, oval, or hook configuration. For example, the hook configuration of the clasp can increase robustness of the clasp by allowing the clasp to engage additional surface area of a tie thread while securing a dental tie device to prevent premature loosening. The removable apertures 2310 can also assist with sizing a tie thread segment length during development activities, or for surgical usability evaluation or data collection purposes.

Figure 54A:
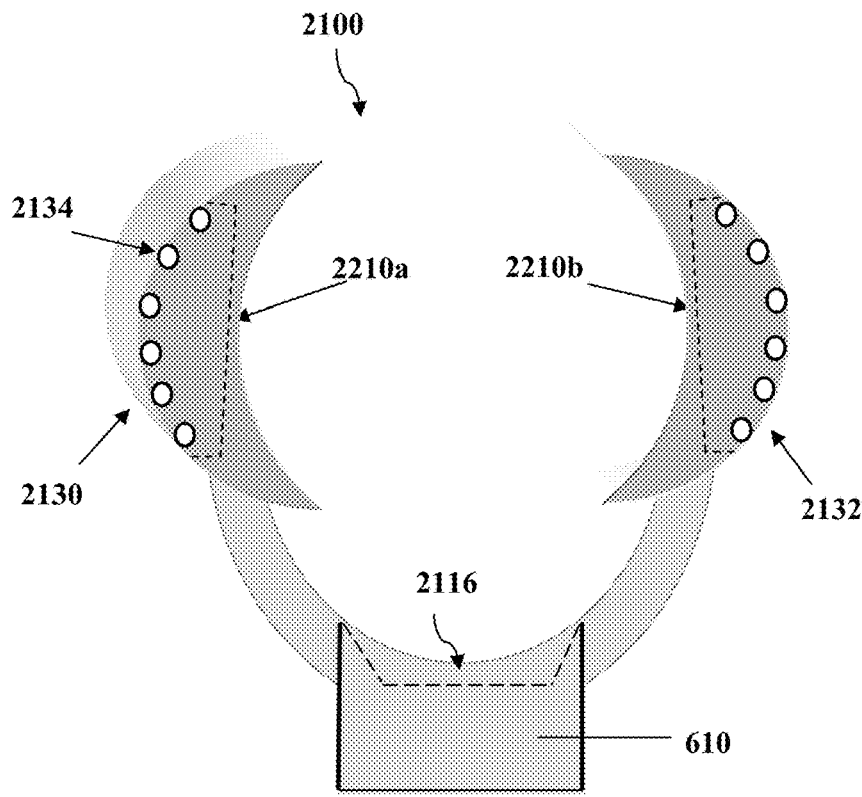
FIG. 54A depicts a front view of a cheek refractor and tie organizer, according to an embodiment.
Figure 54B:
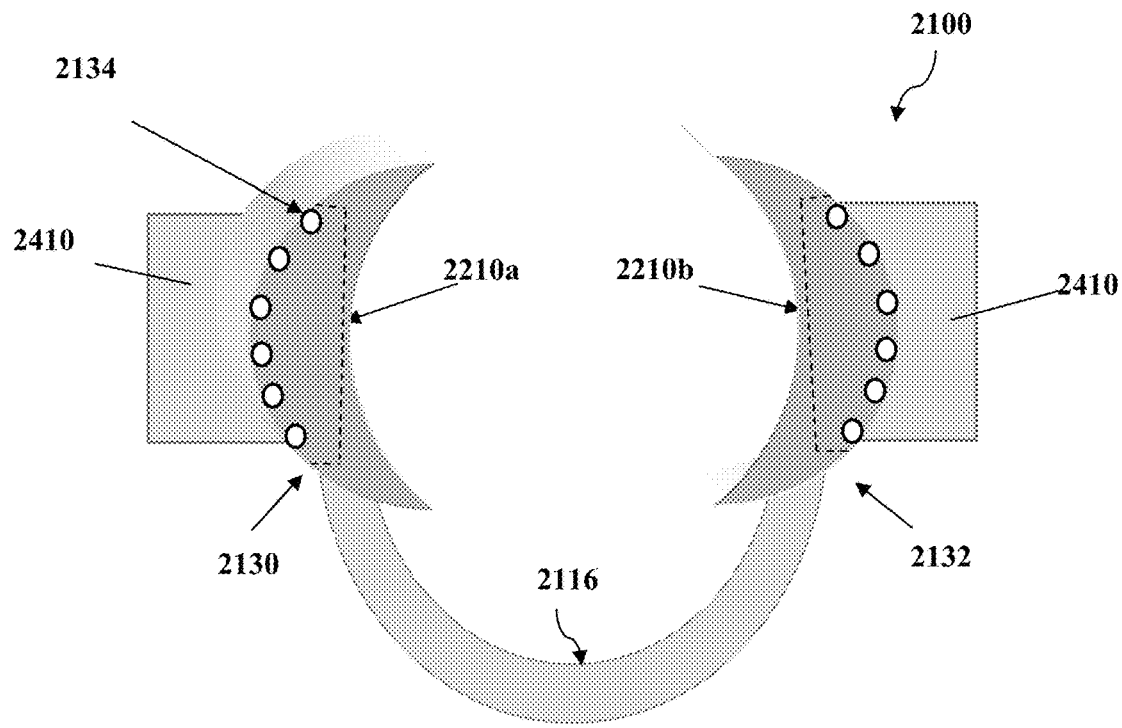
FIG. 54B depicts a front view of a cheek retractor and tie organizer, according to an embodiment.

Referring to FIGS. 54A and 54B, cheek refractor 2100 can further comprise an extended juncture 2116 that can serve as a tray for placement of materials or instruments during oral surgery or other procedures. In another embodiment, a tray 2410 may be fixedly or removably coupled to a portion of juncture 2116 or to an outer edge of first and second tabs 2104, 2106 of cheek retractor 2100. During maxillo-mandibular fixation, for example, the tray 2410 can be used to provide an accessible feature that can be used to store materials such as pre-wound coils 2218 or dental tie devices or to capture materials and/or instruments that fall into the tray 2410. Tray 2410 can vary in size, shape, configuration and/or placement from that depicted in the examples of FIGS. 54A and 54B, in other embodiments.

Figure 55:
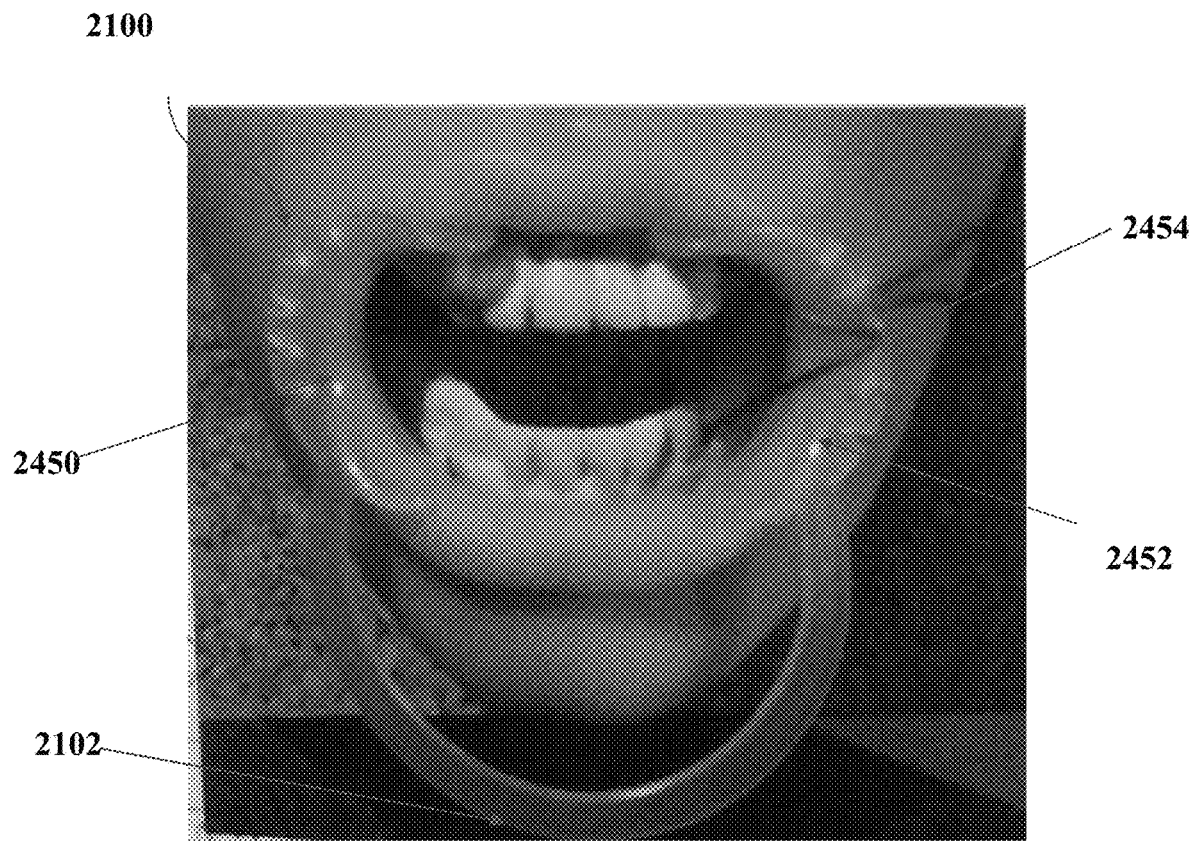
FIG. 55 depicts a front view of a cheek retractor in use, according to an embodiment.

Referring to FIG. 55, a cheek retractor 2100 comprising tie organizers 2130, 2132 is depicted in use according to an embodiment. In embodiments, supporting members 2112, 2114 are gripped and compressed to narrow the cross-sectional area of frame 2102 for oral insertion. Once frame 2102 is narrowed, the first and second tabs 2104, 2106 are positioned in opposing arrangement to each mouth corner 2450, 2452. After the first and second tabs are positioned, the intraoral and extraoral tissue of the lips and cheeks are inserted within the channel of tabs 2104, 2106. The narrowing compression of u-shaped frame 2102 is now released, which allows for simultaneous expansion of a patient's lips and cheeks. The expansion of the lips and cheeks provides a physician with visual and physical access to the oral cavity to perform surgical procedures such as maxillo-manidibular fixation. During a procedure, the upper (maxillary) and lower (mandibular) dentitions are positioned in dental occlusion and secured using dental occlusion or tension band ties 2454, or another device. The ties 2454 are applied to the interdental spaces such as the apical or occlusal embrasure. To facilitate application of the ties, apertures 2134 are utilized to temporarily secure ties 2454 as shown in FIG. 55. In example embodiments, the tie 2454 can be inserted within the cross-sectional area of aperture 2134 after the thread has been looped through an interdental space. In embodiments, each aperture 2134 can be configured to receive individual or multiple ties. The ties can be easily removed from each aperture 2134 by first cutting the tie threads after a tie 2454 has been secured and then removing the loose threads, or by using some other method.

Figure 56:
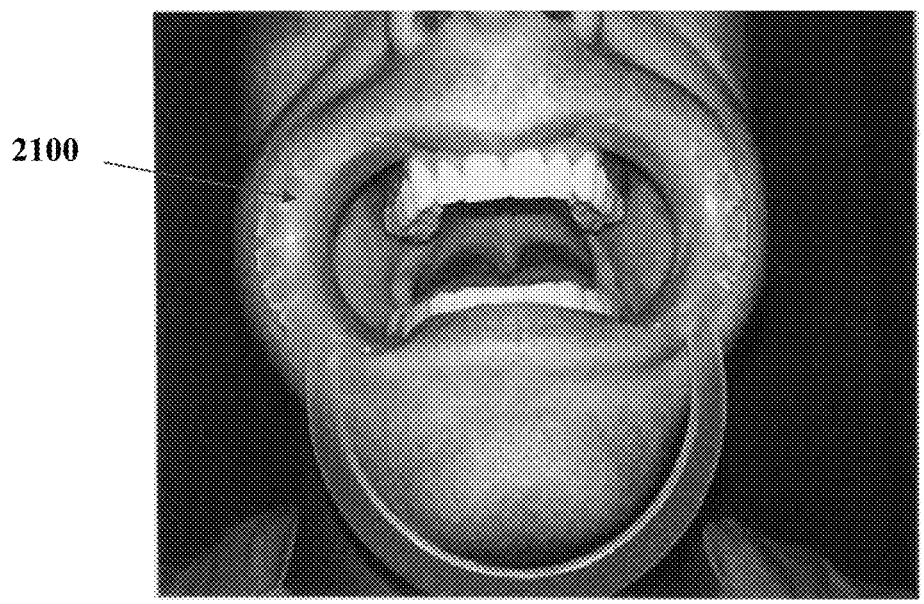
FIGS. 56-80 depict a front view of a cheek retractor in use with methods of applying dental occlusion or tension band ties, according to an embodiment.
Figure 57:
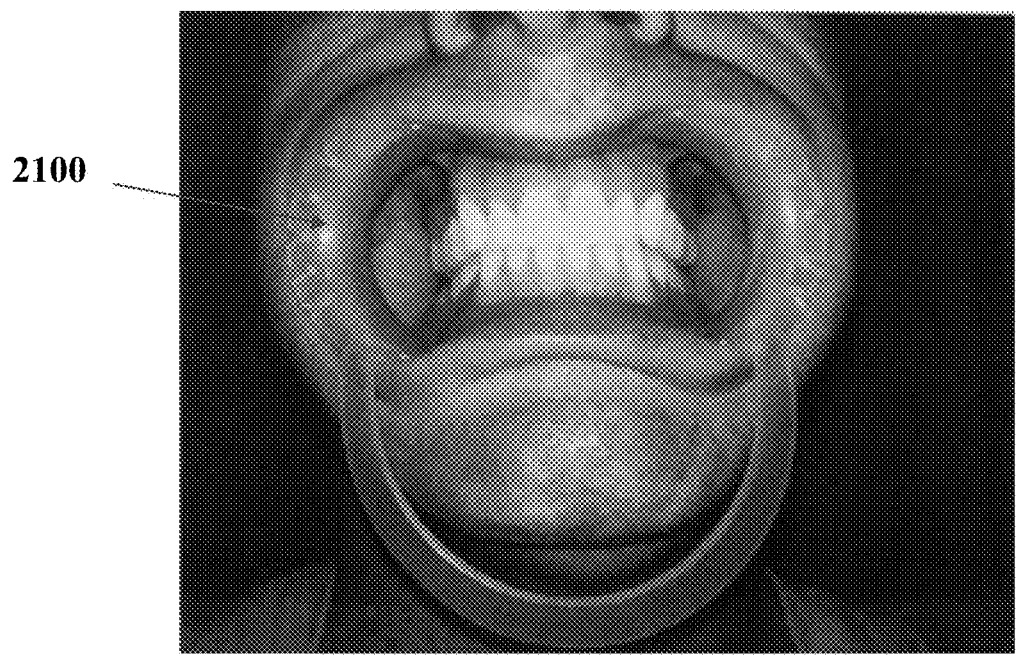

In another example, referring to FIGS. 56-80, a cheek retractor 2100 is depicted in use according to a method of applying dental occlusion or tension band ties. Referring to FIGS. 56-57 specifically, cheek retractor 2100 does not limit temporomandibular joint opening or closure.

Figure 58:
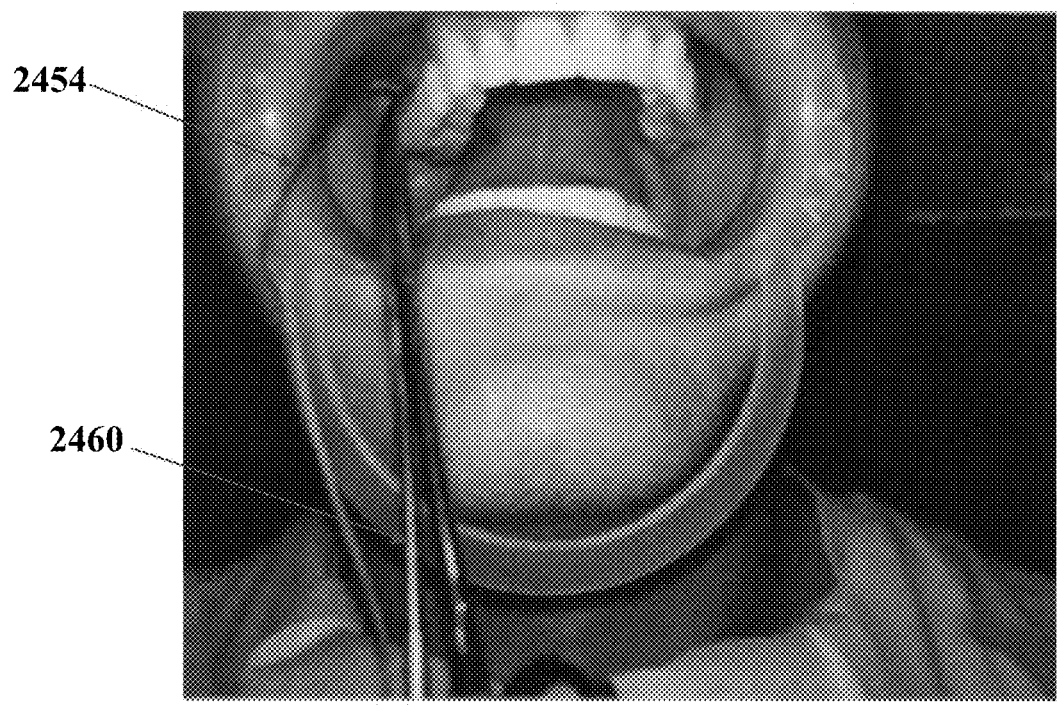
Figure 59:
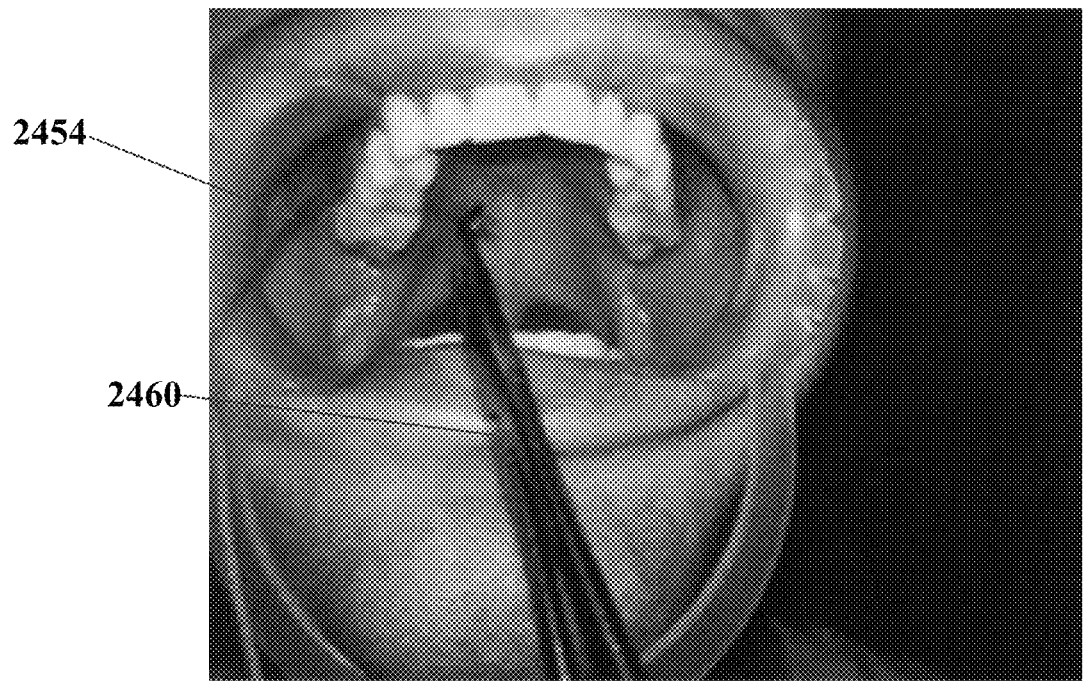
Figure 60:
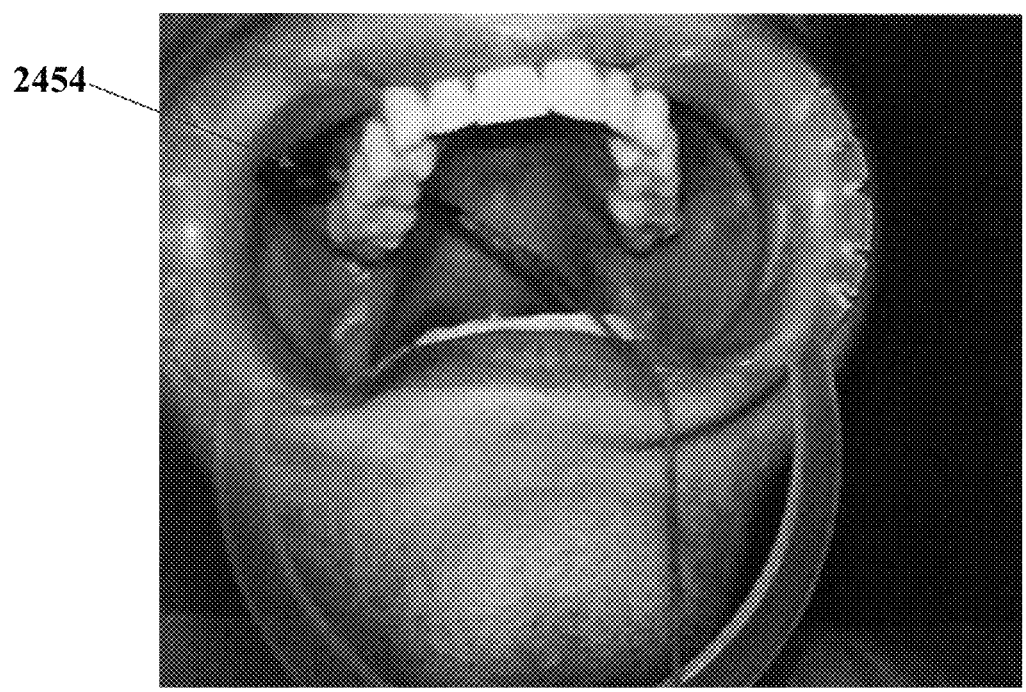

Referring to FIGS. 58-60, dental occlusion or tension band ties are applied through an embrasure between teeth of the upper jaw. In an embodiment of a method of applying dental occlusion or tension band ties, a hemostat 2460 is utilized. In embodiments a "mosquito hemostat" 2460 is utilized. In embodiments, assisting devices such as a mirror can be utilized in application.

Figure 61:
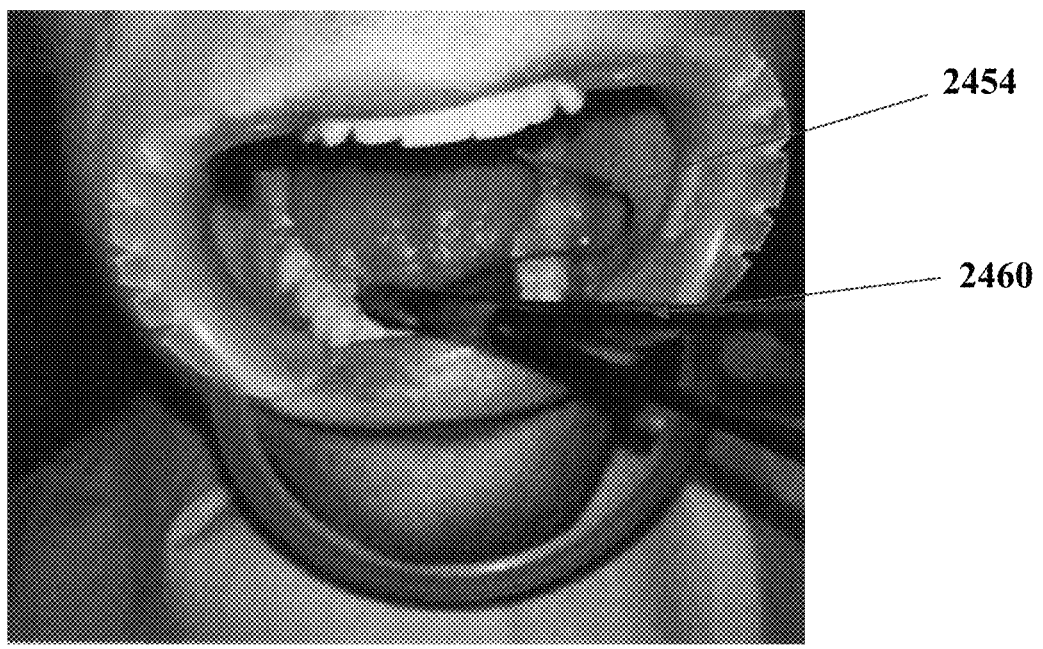
Figure 62:
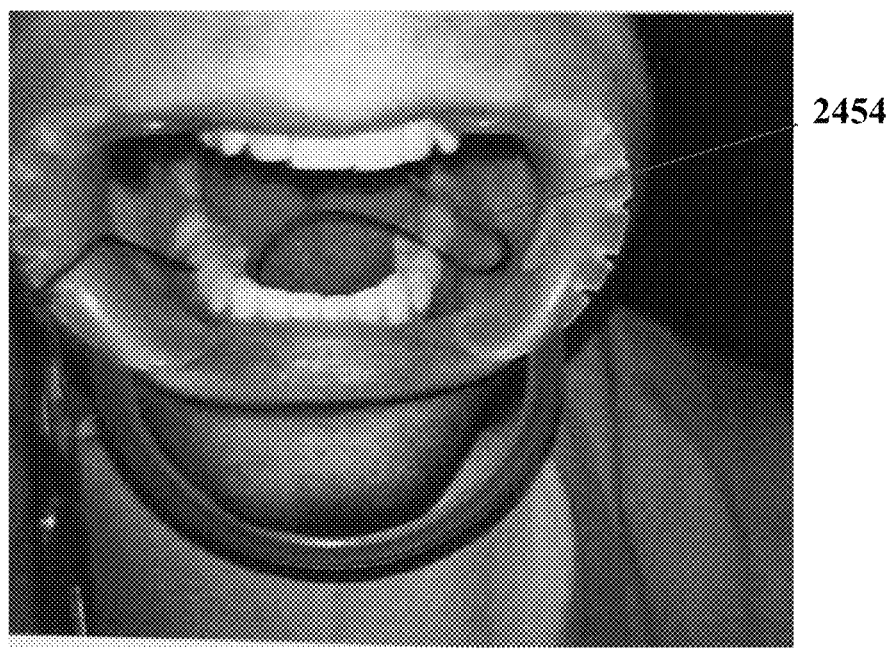
Figure 63:
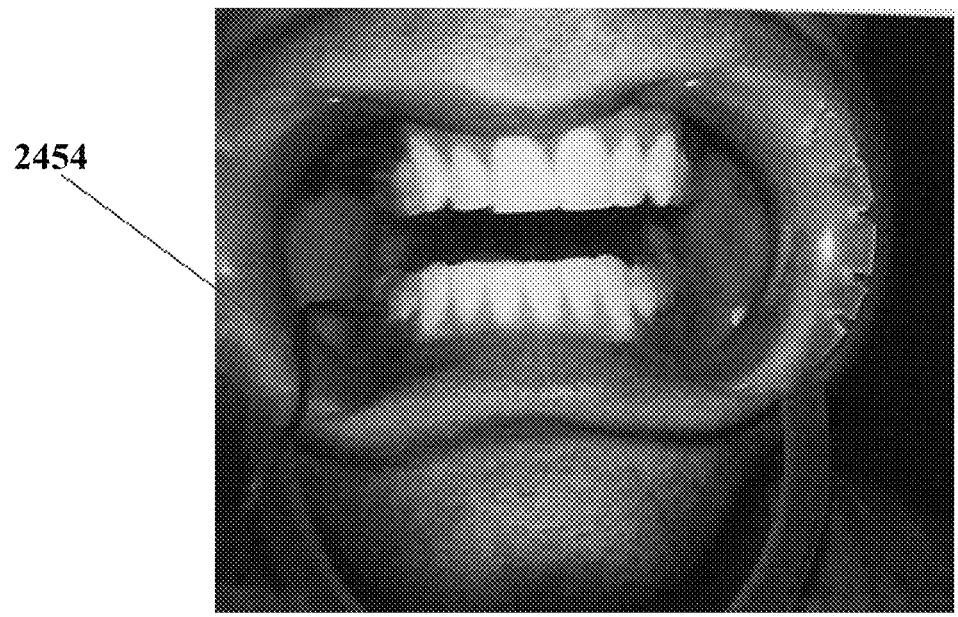

Referring to FIGS. 61-63, a first dental occlusion or tension band tie 2454 is applied through an embrasure between teeth of the lower jaw. As depicted, first dental occlusion or tension band tie 2454 is passed through embrasure #28.

Figure 64:
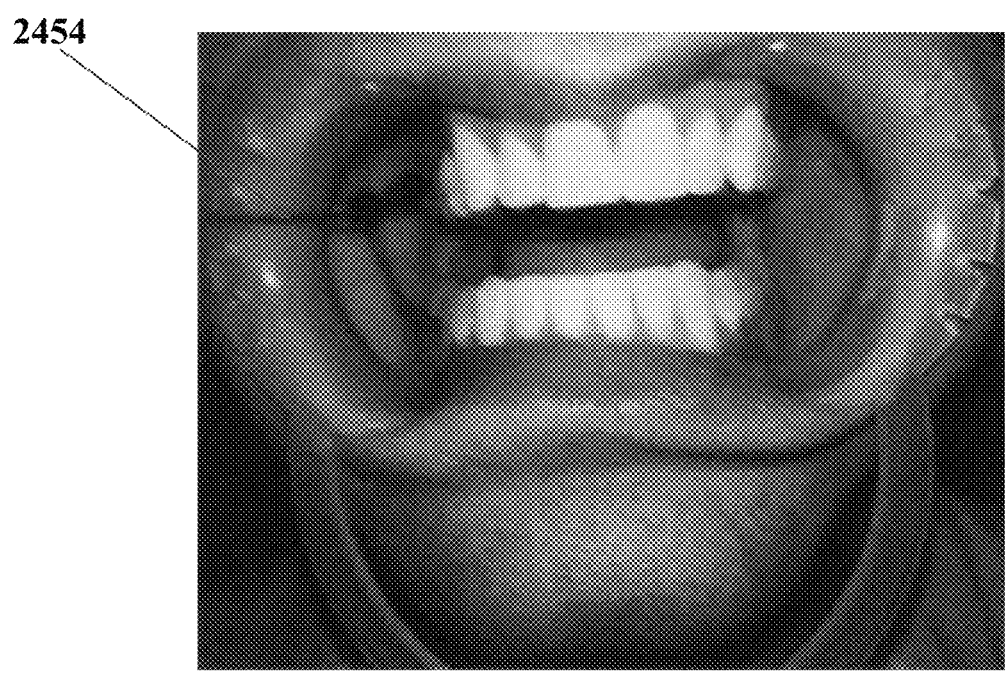

Referring to FIG. 64, a needle portion and proximal thread portion are engaged in the clasp, yet the loop retains enough length or slack to allow the mouth to stay open.

Figure 65:
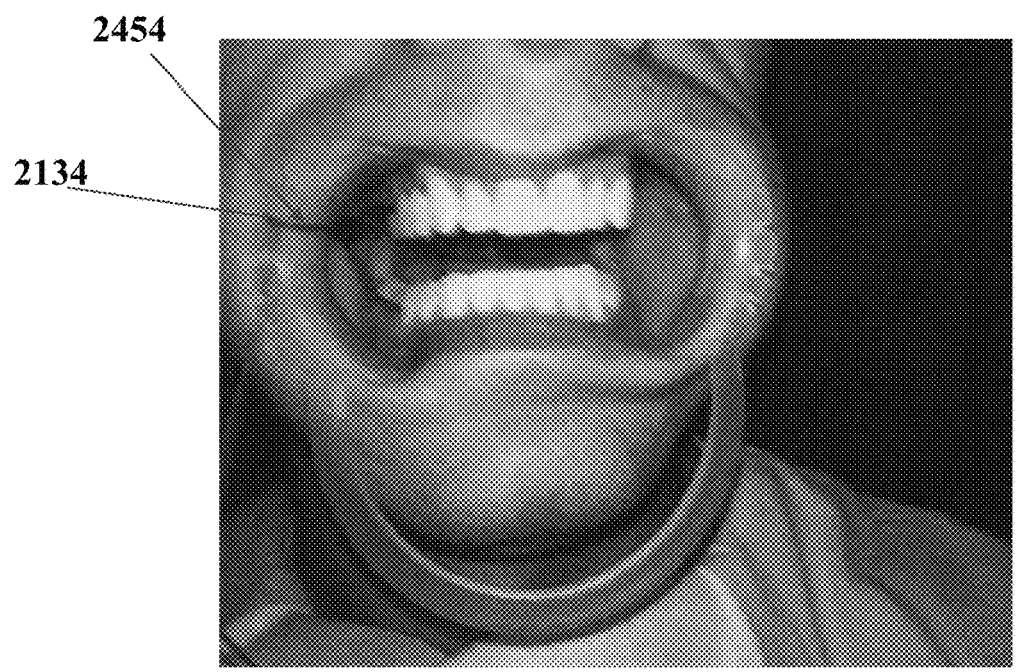
Figure 66:
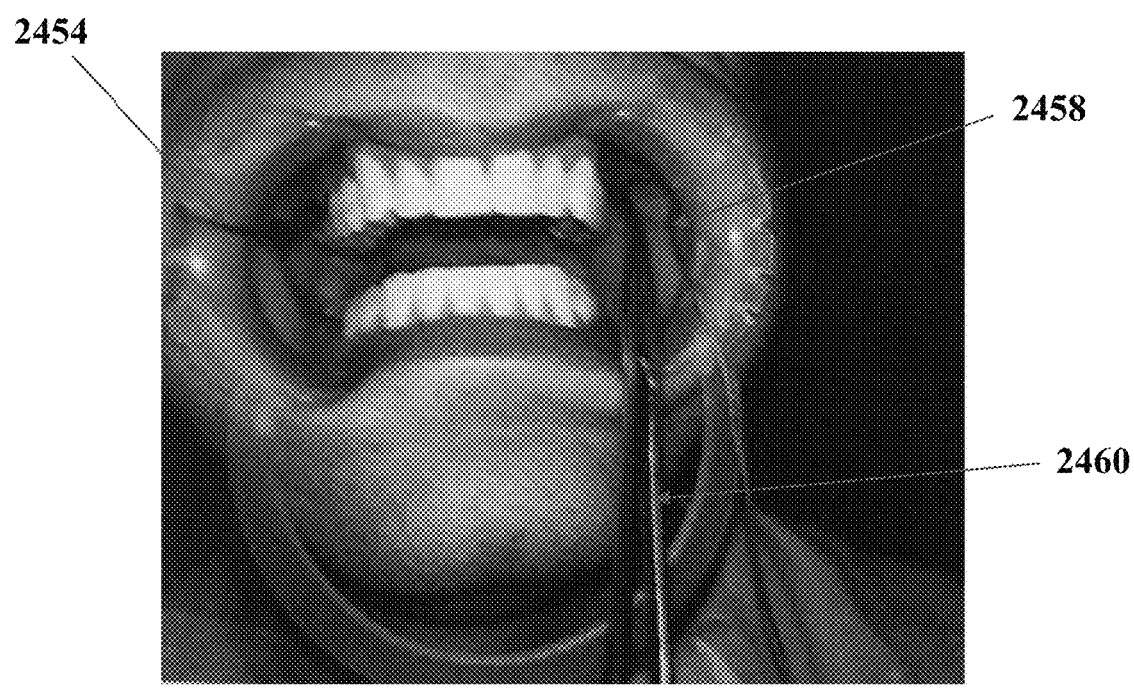
Figure 67:
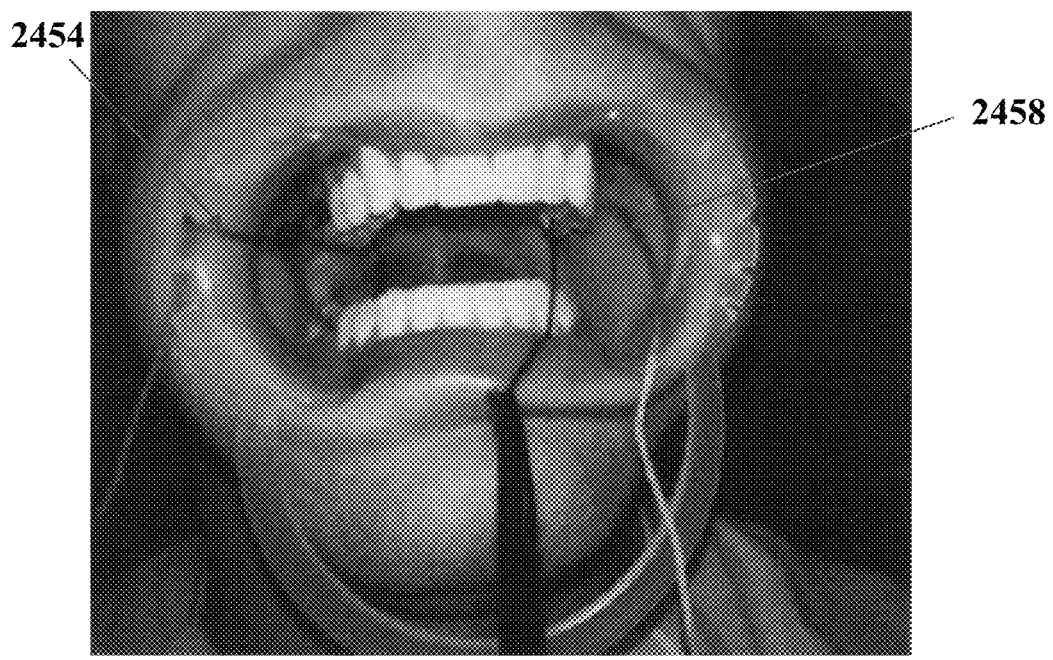
Figure 68:
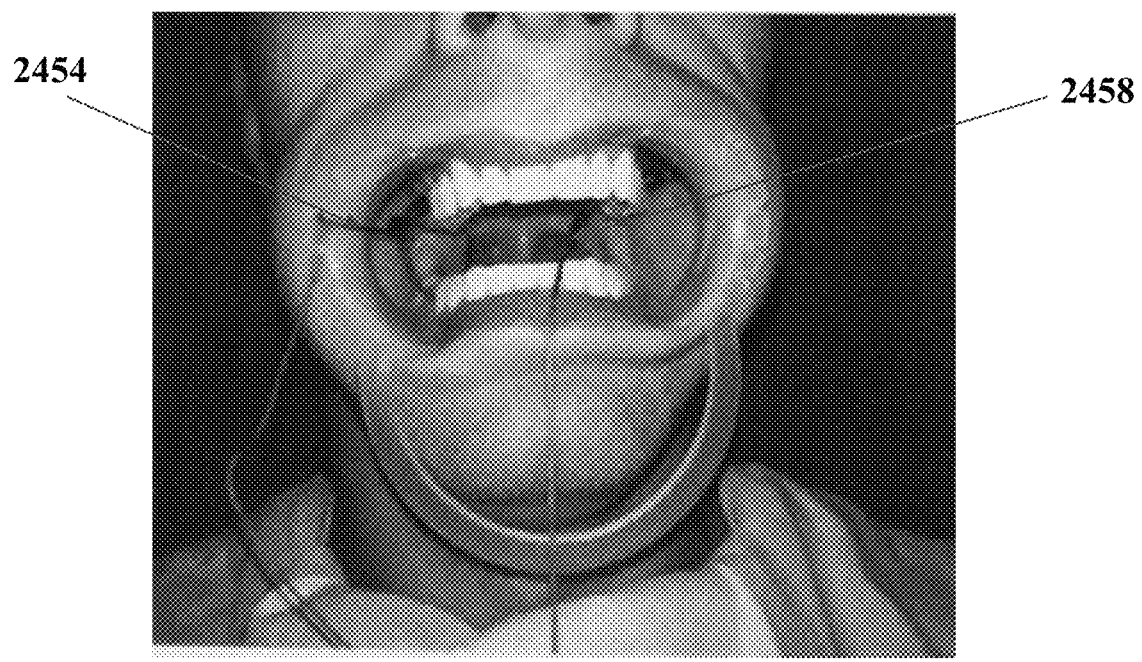
Figure 69:
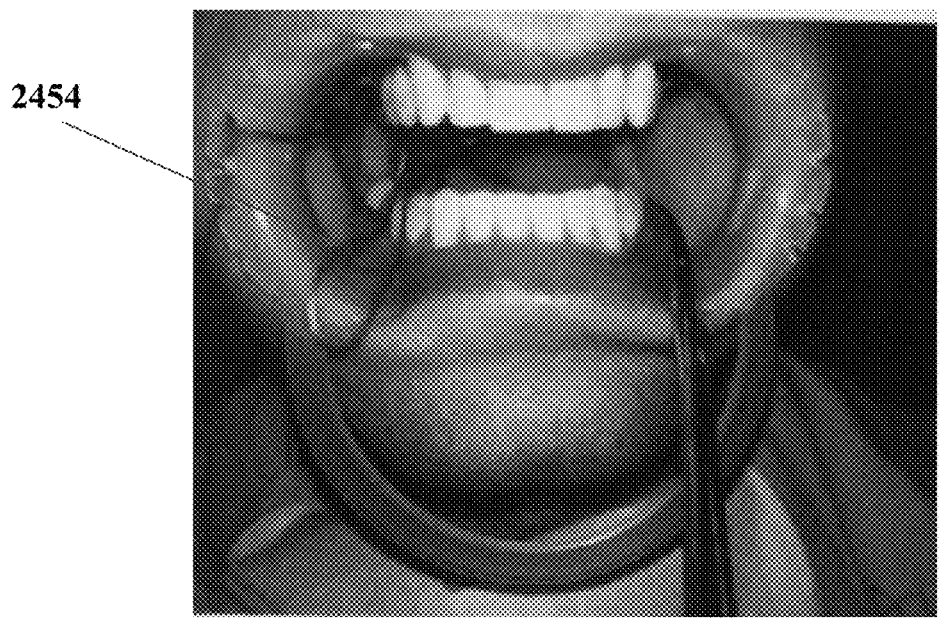

Referring to FIGS. 65-66, first dental occlusion or tension band tie 2454 is temporarily secured in, for example, one of apertures 2134 for the duration of additional dental occlusion or tension band ties 2454 to be applied. In an embodiment, if the lateral edge of cheek retractor 2100 is raised, application of occlusion or tension band ties becomes easier for the applier. Referring to FIGS. 67-69, a second occlusion or tension band tie 2458 is passed through embrasures #13 and #18.

Figure 70:
Figure 71:
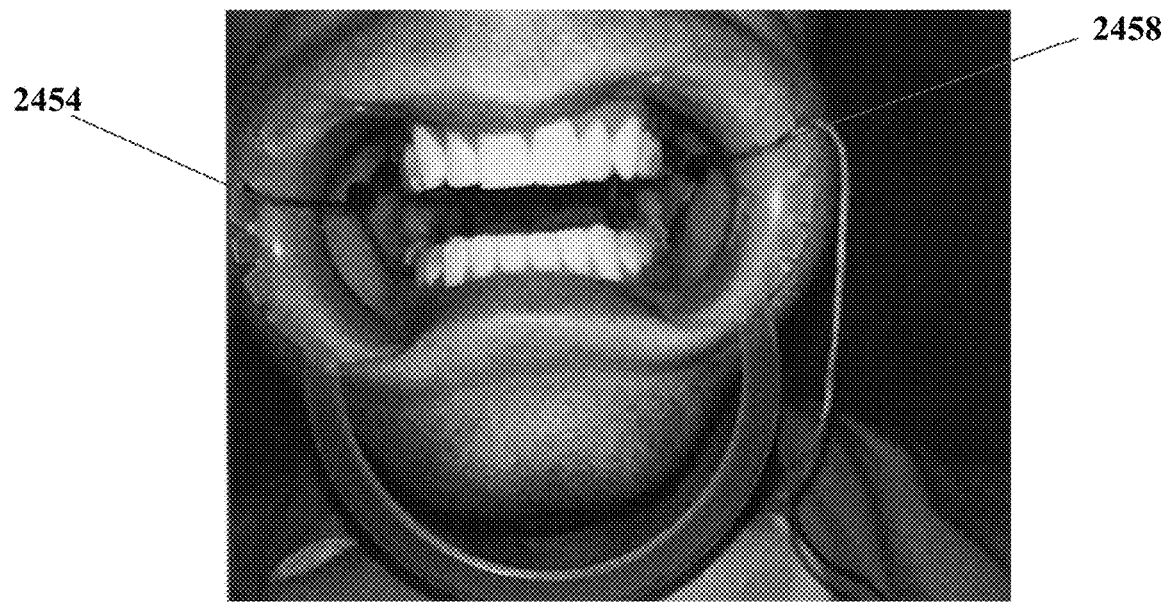

Referring to FIGS. 70-71, second occlusion or tension band tie 2458 is looped through the clasp of second occlusion or tension band tie 2458 and secured.

Figure 72:
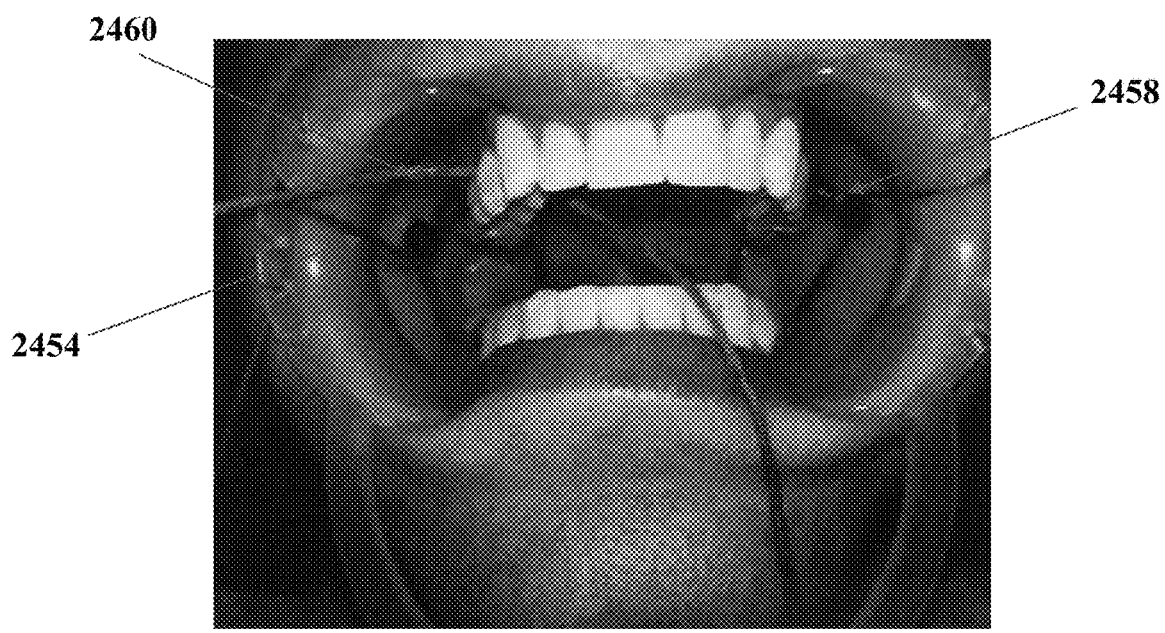
Figure 73:
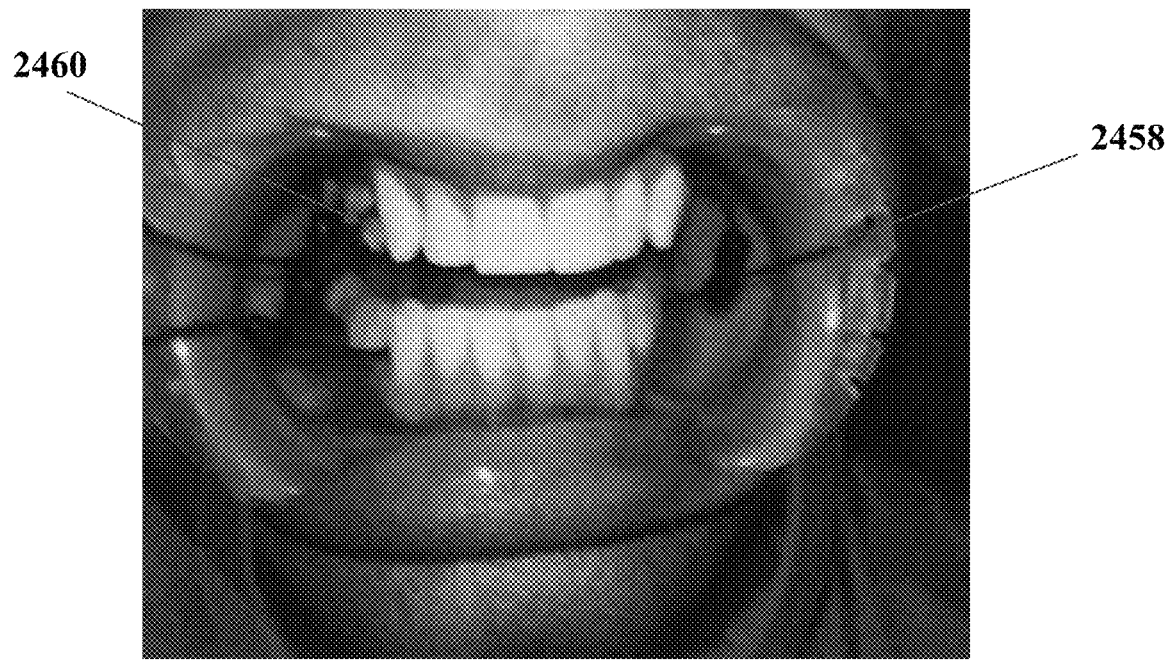

Referring to FIGS. 72-73, a third occlusion or tension band tie 2460 is applied through embrasures of teeth of the upper and lower jaw. According to an embodiment, third occlusion or tension band tie 2460 is a smaller style due to the smaller embrasure. Referring specifically to FIG. 73, third occlusion or tension band tie 2460 is looped through the clasp of third occlusion or tension band tie 2460 and secured. As depicted, third occlusion or tension band tie 2460 is passed through embrasures #4 and #26.

Figure 74:
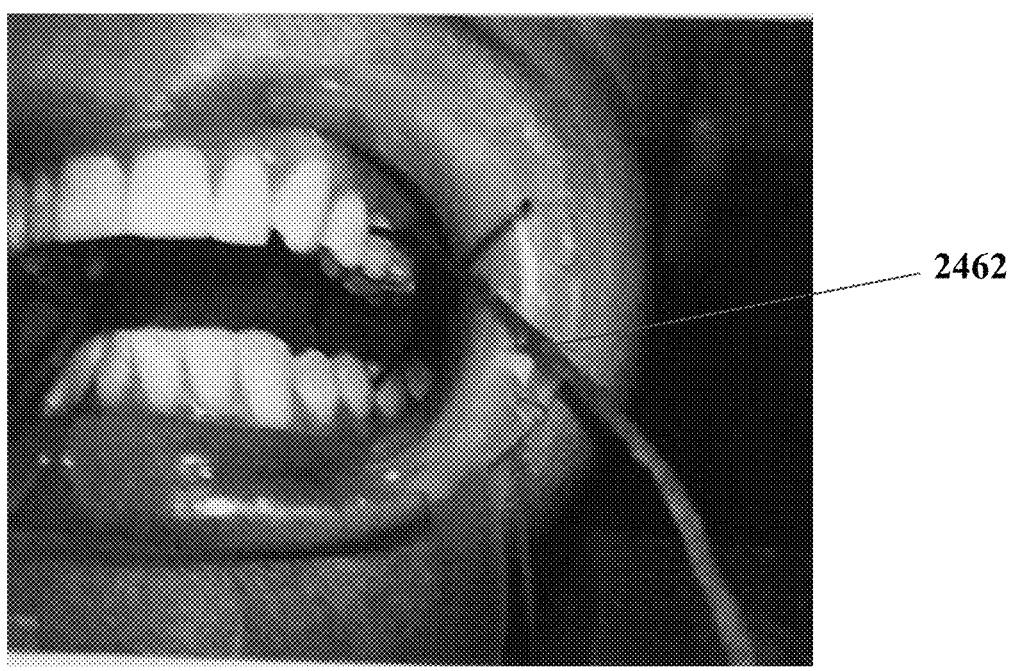

Referring to FIG. 74, a fourth occlusion or tension band tie 2462 is applied through embrasures of teeth of the upper and lower jaw. As depicted, fourth occlusion or tension band tie 2462 is passed through embrasure #12.

Figure 75:
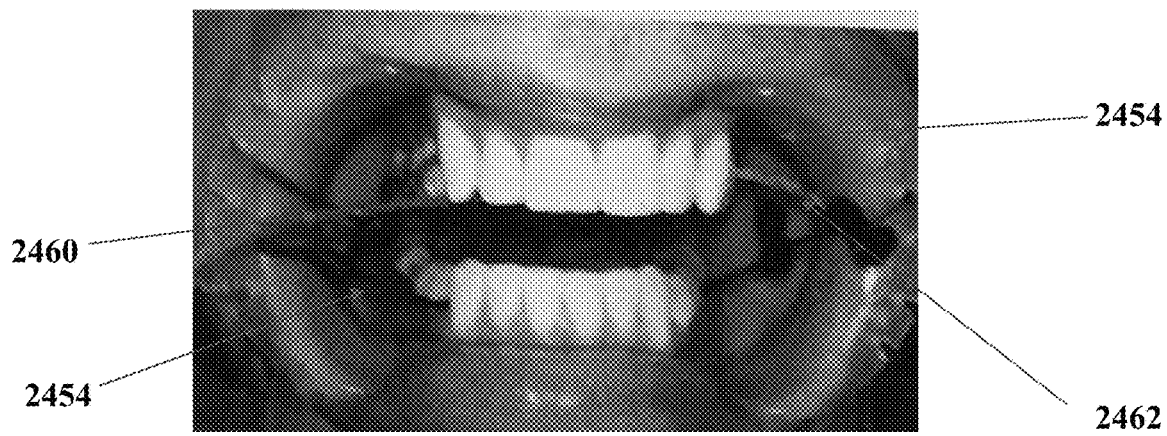

As depicted in FIG. 75, four occlusion or tension band ties are fully looped through embrasures of teeth of the upper and lower jaw; first dental occlusion or tension band tie 2454, second occlusion or tension band tie 2458, third occlusion or tension band tie 2460, and fourth occlusion or tension band tie 2462. Each of the ties 2454, 2458, 2460, and 2462 are respectively organized and secured in a respective aperture 2134.

Figure 76:
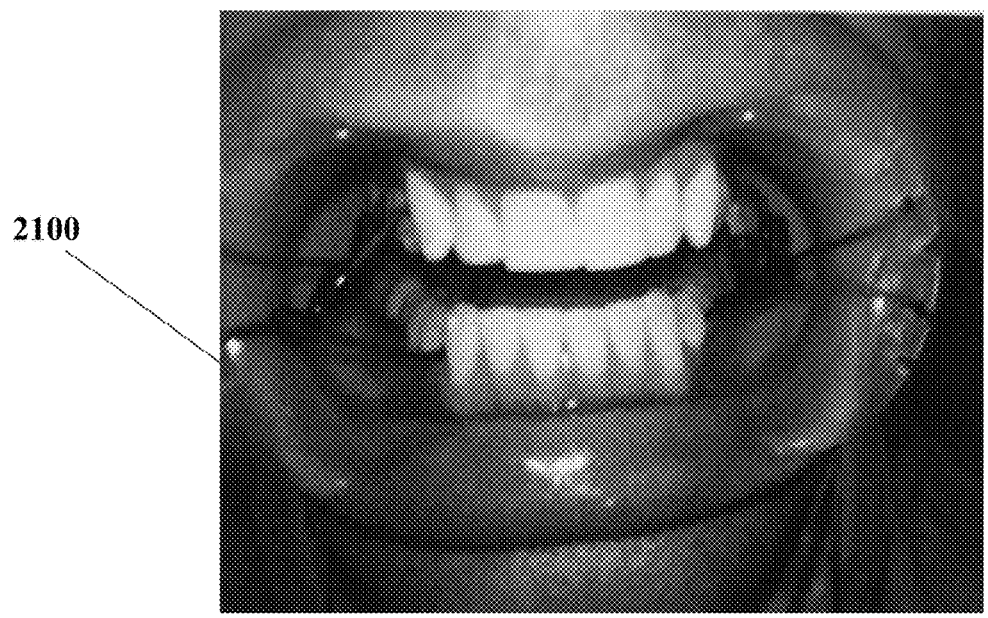
Figure 77:
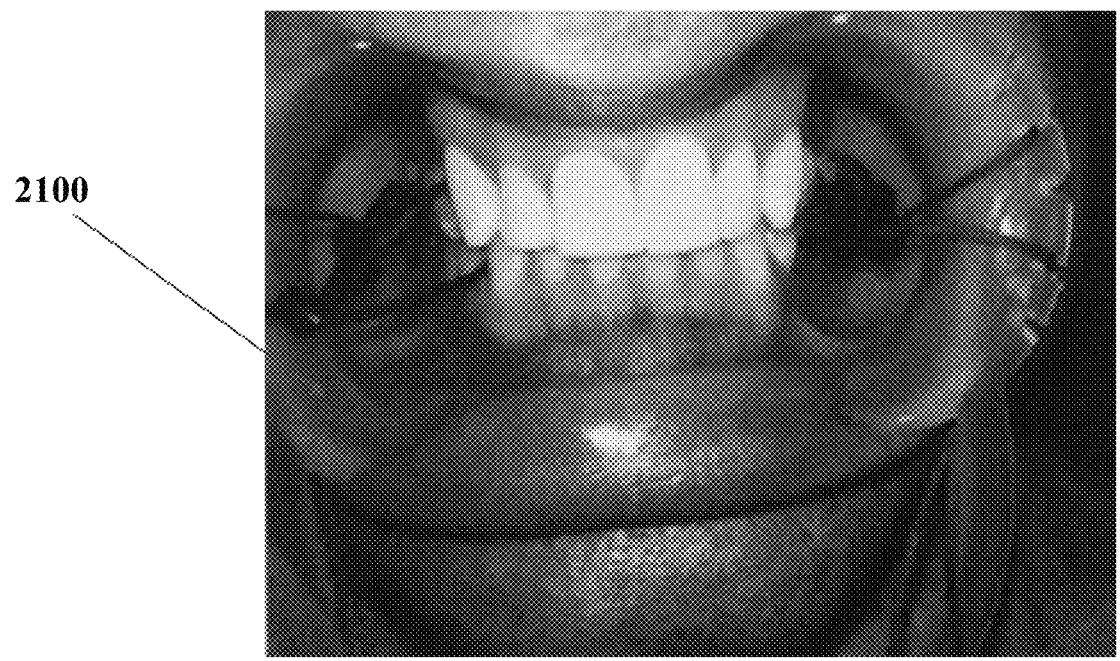

Referring to FIGS. 76-77, the oral cavity can readily move from open (FIG. 76) to closed (FIG. 77). Ties 2454, 2458, 2460, and 2462 remain secure in cheek retractor 2100 and do not dislodge with the closing of the teeth. During application, such closing can be used to check occlusion.

Figure 78:
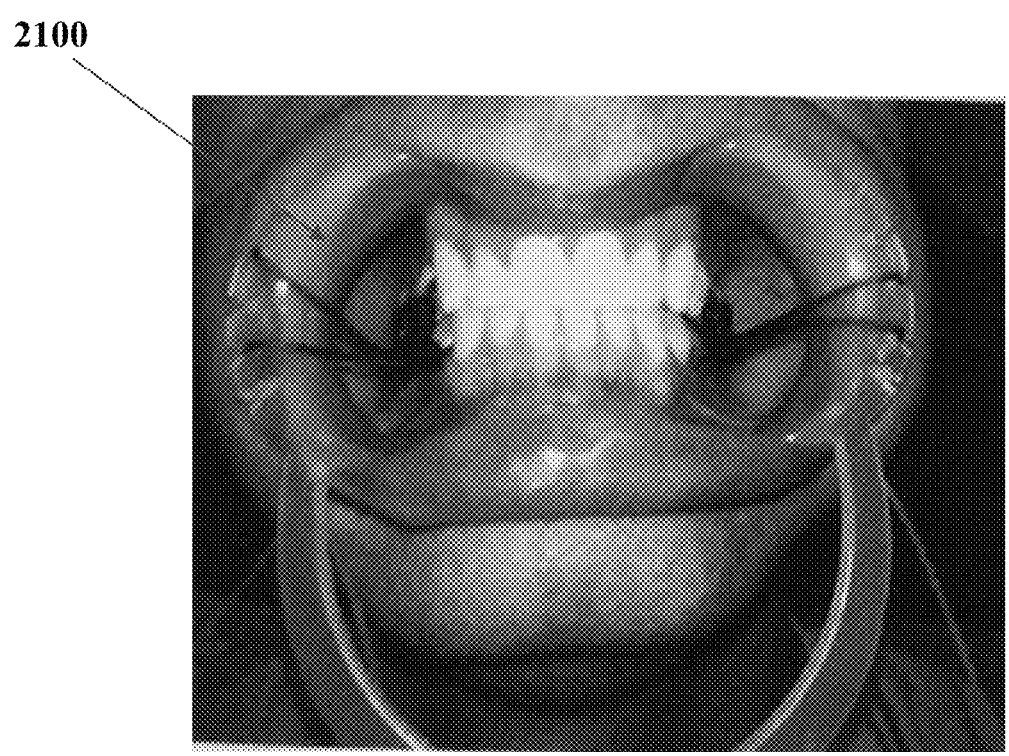

Referring to FIG. 78, ties 2454, 2458, 2460, and 2462 are tightened or cinched from front to back to secure the occlusion. Any remainder or "tail" from ties 2454, 2458, 2460, and 2462 can be organized in cheek retractor 2100.

Figure 79:
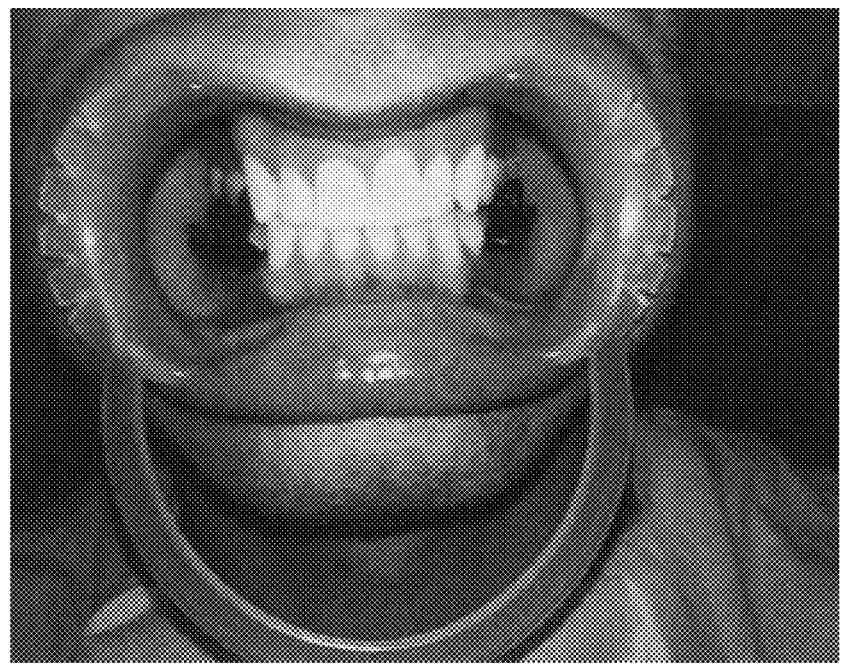

Referring to FIG. 79, ties 2454, 2458, 2460, and 2462 are cut with a cutting tool, and the residual "tails" can be discarded. The aforementioned loops of ties 2454, 2458, 2460, and 2462 remain secure.

Figure 80:
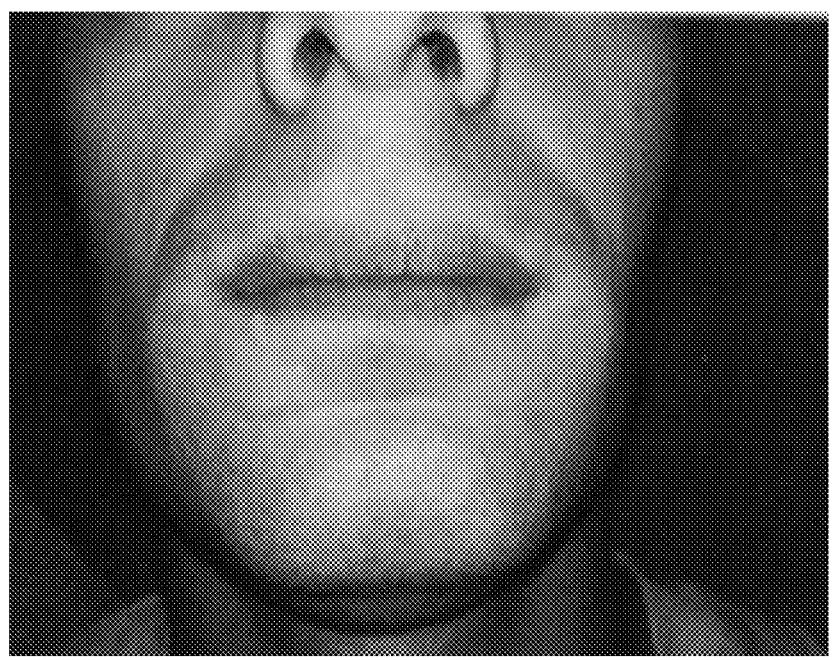

Referring to FIG. 80, the lips of the user easily close over ties 2454, 2458, 2460, and 2462 when applied and secured (consider, in contrast, the arch bars of FIG. 1). A more streamlined profile is thereby achieved according to embodiments of the invention.

Training Devices, Systems, and Kits for MMF

Embodiments relate to training devices, systems, kits and training methods for MMF techniques. In an embodiment, a training system or kit can comprise a practice model assembly including a replica human skull having one or more mandibular and maxillary fractures, and a silicon face cover either permanently or removably coupled to the facial surface of the replica skull. The assembly can optionally comprise a permanently or removably attachable soft tongue insert and/or gingiva insert.

In another embodiment, the system or kit can further comprise one or more removable lip and cheek retractors. In another embodiment, the lip and cheek retractor includes a tie organizer for temporarily organizing and securing tie bands thereto.

In another embodiment, the system or kit can further comprise instrumentation and/or tools for performing MMF techniques. For example, the system or kit can comprise any of a combination of a plurality of dental occlusion ties and/or tension band ties (referred to herein as "DO ties" and "TB ties," respectively), trimming tools, comfort caps, sizing devices, and/or dilation devices, hardware for performing "internal fixation" (plating the fracture through an incision) such as Ivy loop wire, Dimac wire, metal arch bars, and/or stainless steel wires, and/or required surgical or dental instruments for performing the procedures such as mirrors, surgical needles, threading devices, dental picks, or any combination thereof.

In another embodiment, a system or kit can further comprise instructions in the form of a written instruction sheet or manual, and/or a digital format such as, but not limited to, DVD or Blu-ray disc(s), CD-ROM, memory stick, website address, and/or PINs or codes for accessing and/or downloading training materials to a personal device such as a smart phone, tablet, and/or computer.

In another embodiment, a system or kit can comprise a plurality of practice model assemblies of different sizes, such as a pediatric size and an adult size. In an alternative embodiment, a system or kit can comprise one or more non-human animal practice models for training on or more animal types in a veterinary dentistry setting.

In embodiments, the practice model assembly, system, and kit, are useful tools for teaching clinicians the process of applying one or more MMF technologies or techniques in which mandible fractures and/or maxilla fractures require re-establishment of dental occlusion. The practice model assembly of embodiments is designed specifically to emphasize the anatomic challenges of performing MMF technologies. Such challenges can include, for example, cheek restrictions, apical embrasure positions and sizes, hardware, tie, and/or instrumentation dimensions, etc. The practice model assembly, system, and kits, according to embodiments, allow for rapid adoption of MMF techniques.

Figure 81:
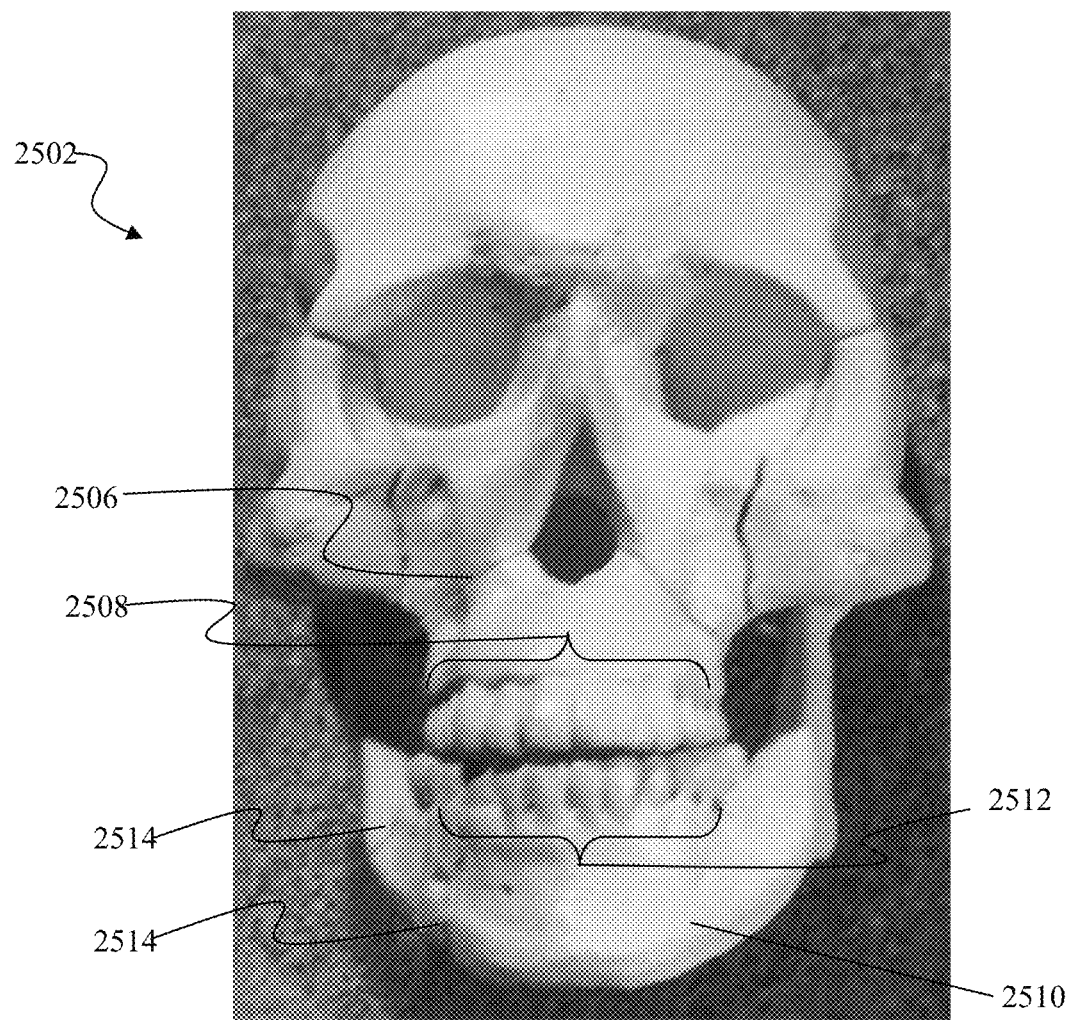
FIG. 81 depicts a front view of a human replica skull of a practice model assembly having one or more mandibular and maxillary fractures, according to an embodiment.
Figure 82:
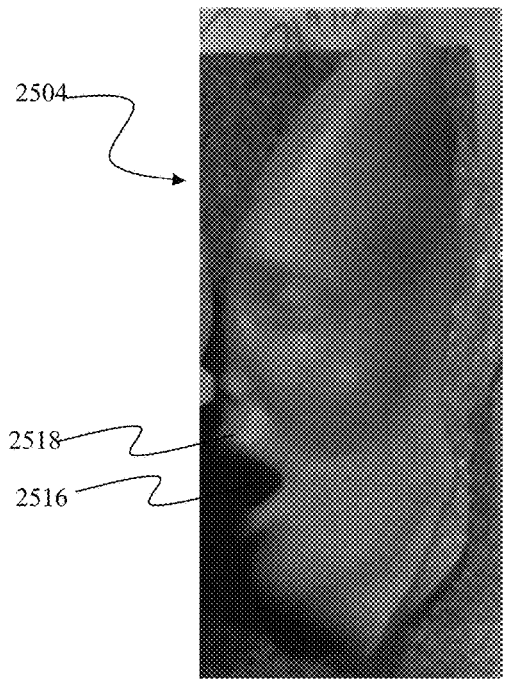
FIG. 82 depicts a side view of a face cover of a practice model assembly, according to an embodiment.
Figure 83:
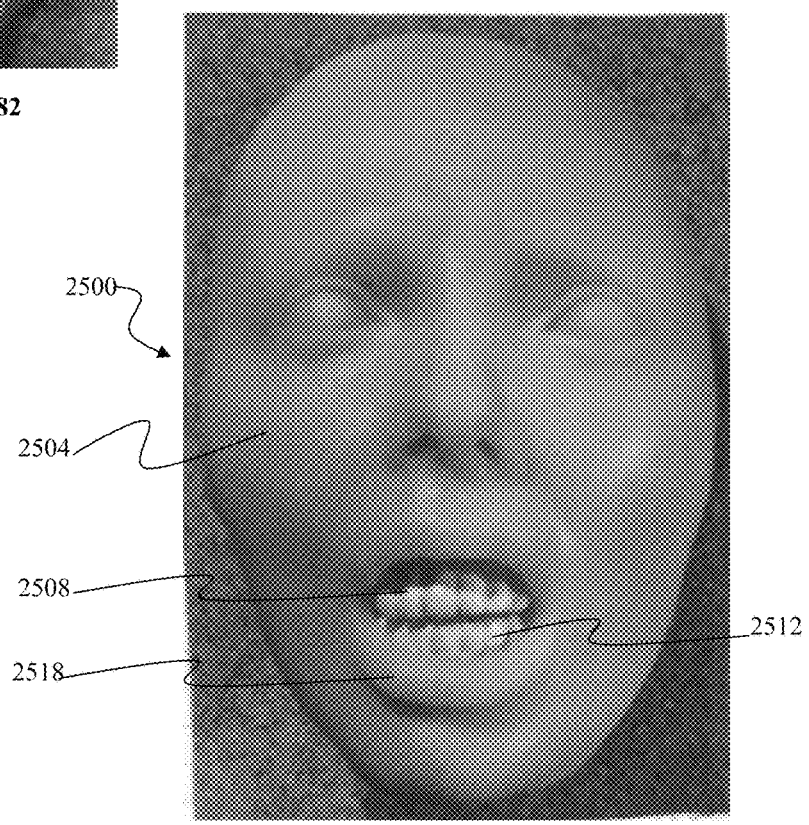
FIG. 83 depicts the face cover of FIG. 82 coupled to the replica skull of FIG. 81 to form a practice model assembly, according to an embodiment.

Referring to FIGS. 81-83, a practice model assembly 2500 for use in training of MMF techniques generally includes a replica skull 2502 and a face cover 2504. Referring to FIG. 81, replica skull 2502 resembles an adult human skull and includes a maxilla 2506 and a set of maxillary teeth 2508, and a mandible 2510 and a set of mandibular teeth 2512. In alternative embodiments, replica skull 2502 can resemble a pediatric human, or any of a variety of non-human animals. Replica skull 2502 further includes one or more mandible fractures 2514, and/or one or more maxillary fractures (not shown). Replica skull 2502 can be formed of any of a variety of rigid materials that resemble bone, such as, for example, plaster or plastic.

Referring to FIG. 82, face cover 2504 resembles an adult human face and is sized to fit over replica skull 2502. Face cover 2504 includes an oral cavity 2516 or mouth and lips 2518. In an alternative embodiment, face cover 2504 resembles a pediatric human, or any of a variety of non-human animals. Face cover 2504 can be formed of a material that resembles the elasticity of skin, such as, for example, silicone.

Referring to FIG. 83, face cover 2504 is coupled to replica skull 2502 such that maxilla teeth 2508 and mandibular teeth 2512 are accessible through oral cavity 2516. Face cover 2504 can be either permanently or removably coupled to replica skull 2502 by any of a variety of coupling mechanisms including, but not limited to, static electricity, friction fit, adhesives such as permanent glues or removable or fugitive glues, snaps, buttons, zippers, hook and loop systems, or combinations thereof.

In some embodiments not shown, the assembly can optionally comprise a permanently or removably attachable soft tongue insert and/or gingiva insert to more closely resemble a patient's mouth and the anatomical challenges associated with accessing the oral cavity to perform a MMF procedure.

Figure 84:
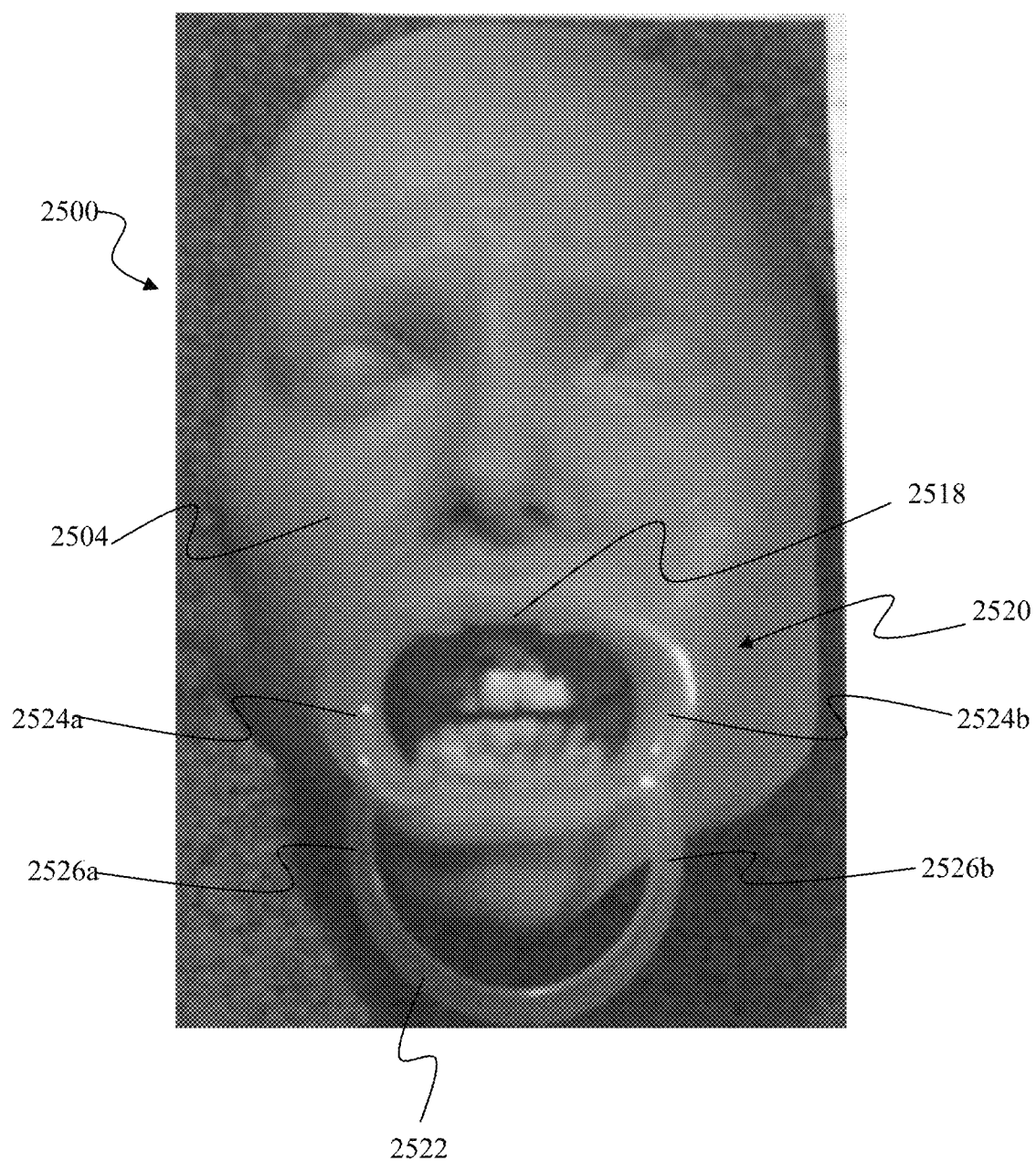
FIG. 84 depicts a front view of the practice model assembly according to FIG. 83 including a standard lip and cheek retractor coupled thereto, according to an embodiment.

Referring to FIG. 84, a standard lip and cheek retractor 2520 is placed around oral cavity 2516 to retract lips 2518. In embodiments, retractor 2520 comprises a u-shaped frame 2522, and first and second tabs 2524a, 2524b for engaging and retracting lips 2518, each tab 2524a and 2524b being coupled to a supporting member 2526a, 2526b, respectively. Supporting members 2526 allow for compression and expansion of cheek retractor 2520 via u-shaped frame 2522. In embodiments, supporting members 2526a, 2526b are coupled to first and second tabs 2524a, 2524b to provide independent movement of tabs 2524 for insertion into oral cavity 2516.

During MMF training, cheek retractor 2520 is compressed via supporting members 2526 of u-shaped frame 2522 for oral insertion. Insertion of retractor 2520 engages the convex channel of tabs 2524 with the interior and exterior of cover 2504, thereby simulating the engagement of intraoral and extraoral tissue of a patient's lips and cheeks. After first and second tabs 2524 are engaged, compressed supporting members 2526 are released to allow for expansion of cover 2504, resembling the expansion or retraction of the lips and cheeks from the teeth. In this position, oral cavity 2516 is visually and physically accessible to perform MMF training procedures, and for the insertion of hardware and instrumentation for performing such training procedures.

Figure 85:
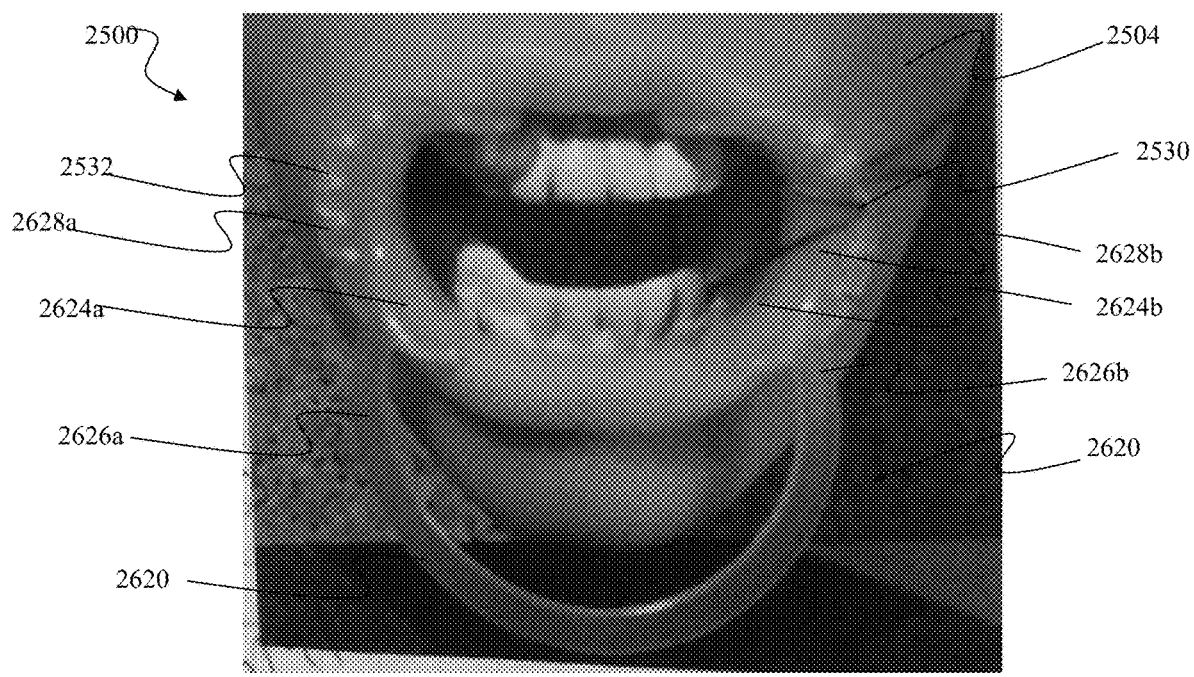
FIG. 85 depicts a front view of practice model assembly according to FIG. 83 including a modified lip and cheek retractor and dental occlusion band, according to another embodiment.
Figure 86:
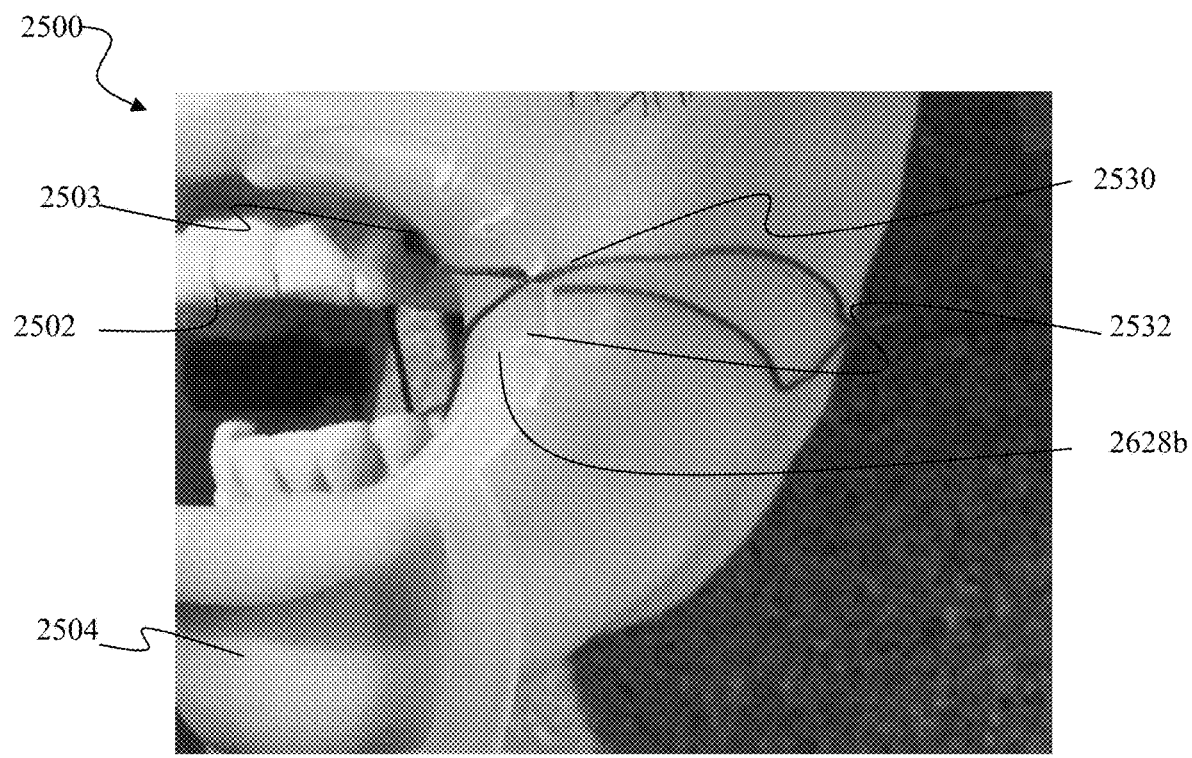
FIG. 86 depicts a front perspective close-up view of one side of the practice model assembly according to FIG. 85.

Referring to FIGS. 85 and 86, in other embodiments in which MMF using tie bands is performed, replica skull 2502 comprises one or more interdental apertures 2503 representing dilated or opened apical embrasures for inserting one or more tie bands. In this embodiment, a modified lip and cheek retractor 2620 may be preferred. Retractor 2620 includes u-shaped frame 2622 and first and second tabs 2624a, 2624b as described with respect to retractor 2620. First and second tabs 2624a, 2624b of retractor 2620 further comprises a first and second tie organizers 2628a, 2628b configured to facilitate the arrangement of one or more DO and/or TB tie threads 2530. In embodiments, tie organizers 2628a, 2628b can comprise a plurality of notch elements 2532 for the insertion of tie threads 2530.

During this training procedure, the upper (maxillary) and lower (mandibular) dentitions are positioned in dental occlusion and secured using dental occlusion or tension band ties. The ties are applied to interdental spaces 2503 of model 2502 such as the apical or occlusal embrasure. Tie thread 2530 can be inserted within the cross-sectional area of notch elements 2532 after the thread has been looped through interdental space 2503. Once all desired threads 2530 are in place, the ties can be tightened and secured accordingly to accomplish dental occlusion and/or tensioning. The tie threads can then be easily removed from each notch element 2532 by first cutting tie threads 2530 after a tie has been secured and then removing the loose threads.

In other embodiments, assembly 2500 can be including as a system or kit that can further comprise instrumentation and/or tools for performing MMF techniques. For example, the system or kit can comprise any of a combination of a plurality of DO ties and TB ties, trimming tools, comfort caps, sizing devices, and/or dilation devices, hardware for performing "internal fixation" (plating the fracture through an incision) such as Ivy loop wire, Dimac wire, metal arch bars, and/or stainless steel wires, and/or any required surgical or dental instruments for performing these procedures.

In other embodiments, a system or kit can comprise instructions in the form of a written instruction sheet or manual, and/or a digital format such as, but not limited to, DVD or Blu-ray disc(s), CD-ROM, memory stick, website address, and/or PINS or codes for accessing and/or downloading training materials to a personal device such as a smart phone, tablet, and/or computer.

In yet other embodiments, a system or kit can comprise a plurality of practice model assemblies 2500 of same or different sizes, such as a pediatric size and an adult size. In an alternative embodiment, a system or kit can comprise one or more non-human animal practice models for training on or more animal types in a veterinary dentistry setting.

In embodiments, the practice model assembly, system, and kit, are useful tools for teaching clinicians the process of applying one or more MMF technologies or techniques in which mandible fractures and/or maxilla fractures require re-establishment of dental occlusion. The practice model assembly of embodiments is designed specifically to emphasize the anatomic challenges of performing MMF technologies on adult humans, children, or any of a variety of animals. Such challenges can include, for example, cheek restrictions, apical embrasure positions and sizes, hardware, tie, and/or instrumentation dimensions, etc. The practice model assembly, system, and kits, according to embodiments, allow for rapid adoption of MMF techniques.

Interdental Dilator Devices, Systems and Methods

Embodiments relate to embrasure dilator devices, systems, methods of dilating embrasures for performing dental procedures and surgeries, such as for achieving MMF. In an embodiment, an embrasure dilator device can comprise an expandable elongate body or insert portion, having a continuous triangular cross-sectional profile along a length of the insert portion. The dilator device expands from a compressed configuration having a reduced cross-sectional area so that the dilator device is readily positioned within an embrasure, to an expanded configuration once positioned within the embrasure, thereby gently compressing the soft tissue around the embrasure to physically dilate the embrasure.

In alternative embodiments, the cross-sectional shape of the dilator device is non-triangular and is instead circular, rectangular, oval, curvilinear (i.e., crescent-shaped) or some other suitable shape or combination thereof. In a particular embodiment, the cross-sectional shape is circular.

In another alternative embodiment of the invention, the cross-sectional profile varies in at least one of shape and dimension along the length of the device. In embodiments, one or both of the insert portion of the dilator device includes a tab portion having a cross-sectional area greater than the cross-sectional area of the elongate body. In such embodiments, the insert portion can optionally be reinforced by a polymer material such as a floss-type material.

In an embodiment, the dilator device is formed of a hydrophilic material, and expands from the compressed configuration to the expanded configuration upon exposure to water or aqueous solutions including, but not limited to, saliva, a medicament solution such as anesthetic solution, or any combination thereof.

In an embodiment, the dilator device is formed of a porous material, and more specifically of an open- or closed-cell sponge or foam. In a particular embodiment, the dilator device is formed from a surgical sponge material such as cellulose or hydroxylated polyvinyl acetyl.

The dilator device can optionally include one or more medicaments, lubricants, and/or therapeutic agents, such as, for example, anesthetics, vasoconstrictors, anti-inflammatories, pain relievers, antibiotics, or any combination thereof for application to the surrounding tissue or gingival papilla. In one embodiment, the dilator device includes a topical anesthetic, topical vasoconstrictor, or combinations thereof. The medicaments can be applied to cover at least a portion of an outer surface of the dilator device, and/or incorporated within the dilator device. In an embodiment, one of a topical anesthetic and a topical vasoconstrictor is applied to an outer surface of the dilator device, while the other is contained within the dilator device.

In a particular non-limiting embodiment, a system or kit can comprise materials and/or tools for performing MMF techniques. For example, the system or kit can comprise a plurality of dilator devices, with or without medicaments, any of a combination of a plurality of dental occlusion ties and/or tension band ties (referred to herein as "DO ties" and "TB ties," respectively), trimming tools, comfort caps, sizing devices, lip and cheek retractors, and/or required surgical or dental instruments for performing the procedures such as mirrors, surgical needles, threading devices, dental picks, instructions, or any combination thereof.

In an embodiment, one or more medicaments are pre-applied to the dilator device, and are activated by the addition of water. In another embodiment, one or more medicaments are separately packaged within the kit for application to the dilator device, such as by coating or soaking the device, just prior to use of the dilator device.

Devices of embodiments are not limited to MMF procedures, and can be used for any of a variety of dental procedures in which dilation of an interdental space is desired or required, such as, for example, maxillomandibular advancements, orthognathic surgery, and temporomandibular joint replacements.

In embodiments, dilator devices comprise an inserting tip that forms a point. In embodiments, the point of the inserting tip is similar to a toothpick point. Dilator devices further maintain adequate rigidity to penetrate the embrasure. Thus, there is a trade-off as decreased cross-sectional area will fit the space easier, but will be less rigid/sturdy. Embodiments therefore trade off cross-sectional shape/dimension (round, oval, elliptical, triangular), durometer (rigidity/stiffness), and "expansile capability" (by what percentage will the material enlarge when moistened and/or what force will it apply on the gingival papilla). According to embodiments, certain dilator devices can comprise "more" in certain categories and "less" in other categories. In embodiments, certain dilator devices can likewise comprise "less" in certain categories and "more" in other categories.

Figure 87A:
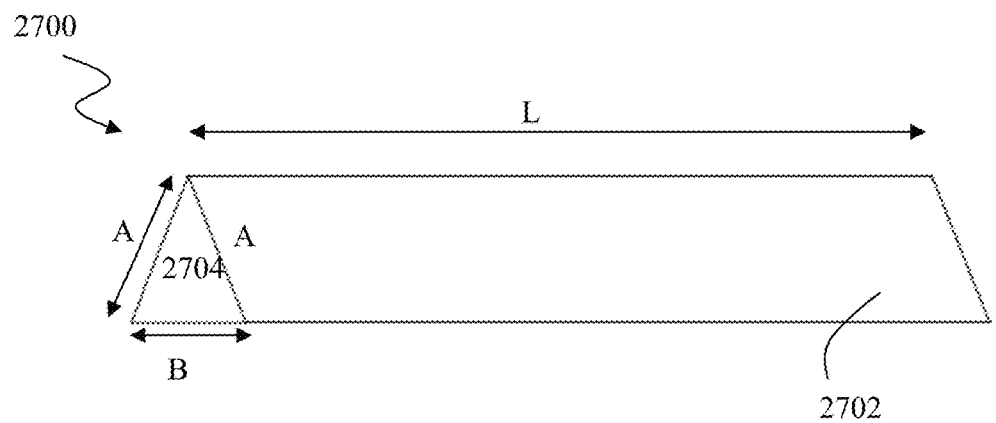
FIG. 87A is a side perspective view of a dilator device having a triangular cross-sectional profile, according to an embodiment.
Figure 87B:
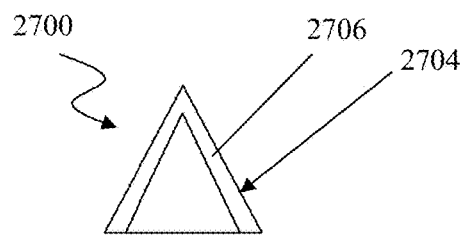
FIG. 87B is a cross-sectional view of the dilator device of FIG. 87A, according to an embodiment.

Dilator devices according to embodiments are generally utilized to dilate an interdental space, such as an apical embrasure, by physically and/or pharmaceutically constricting or compressing the gingival papilla or other soft tissue. As discussed above with respect to FIG. 5, embrasures are defined as the space diverging from the contacting proximal surfaces of two adjacent teeth. An apical embrasure 130 is between the contacting surfaces and the mandible or maxilla, and is substantially filled with gingival papilla 132 (i.e., the gum tissue between the teeth). Typically, apical embrasures are substantially triangular in cross-sectional profile, and more particularly, such triangles are isosceles. When performing MMF with tension band ties and/or occlusion band ties, it is desired to thread the tie through embrasure 130 without causing significant injury or trauma to proximate tissue or teeth. As depicted in the FIGS. 87-90, dilator devices according to embodiments function to dilate embrasure 130 by physically and optionally pharmaceutically compress gingival papilla 132 to provide sufficient access to thread the tie therethrough, Referring to an embodiment depicted in FIG. 87A, dilator device 2700 generally includes an insert portion 2702 comprising an elongate body having a longitudinal length L for inserting within the interdental space, such as an apical embrasure. Longitudinal length L can be sized depending on the anatomical structure of the patient, and can be, for example, in a range from about 0.3 cm to about 1.5 cm, and more particularly about 1 cm.

Device 2700 is shaped to effectively wedge between two adjacent teeth in the apical embrasure 130 (refer, for example, to FIG. 5) while minimally disrupting the gingival papilla 132. In this embodiment, a cross-sectional profile 2704 of insert portion 2702 can comprise an approximate or general isosceles triangle presenting two equal sides A, and a base B. Base B can be sized according to a space between adjacent teeth, and can be, for example, in a range from about 0.10 mm to about 0.80 mm, and more particularly about 0.50 mm. In an alternative embodiment not shown, the cross-sectional profile comprises an equilateral triangle. Any of a variety of other cross-sectional shapes and configurations can be used in other embodiments, some of which are described below. The edges or corners of device 110, in this and other embodiments, can be curved, flat, regular or irregular, square, chamfered, or have some other shape or configuration that aids in insertion, positioning and/or dilation.

In one embodiment, insert portion 2702 has a baseline durometer that is hard enough, such as, for example, a hardness of about 50 to about 100 Shore A durometer, and more particularly from about 60 to about 80 Shore A durometer, that when inserted into the apical embrasure, insert portion 2702 physically displaces or presses on the soft gingival papilla without causing tissue trauma. In another embodiment, insert portion 2702 can comprise a ridge or other extension formed thereon that physically displaces and/or presses on the soft gingival papilla without causing tissue trauma. Mechanically compression of the gingival papilla allows for squeezing of blood and other fluids out of the tissue.

In embodiments, insert portion 2702 can be formed of an expandable material such that the dilator device radially expands from a compressed configuration having a reduced cross-sectional area such that the dilator device is readily positioned within an embrasure, to an expanded configuration once positioned within the embrasure, thereby gently compressing the soft tissue around the embrasure to physically dilate the embrasure. In embodiments, at least one dimension of the cross-sectional profile expands at least two times its original or compressed dimension, and more particularly at least four times its original dimension. In other embodiments, an area of the cross-section profile at least doubles, and more particularly at least quadruples.

In an embodiment, insert portion 2702 is formed of a hydrophilic expandable material, such that expands from the compressed configuration to the expanded configuration upon exposure to water or aqueous solutions including, but not limited to, saliva, a medicament solution such as anesthetic or cleaning solution, or any combination thereof. In an embodiment, the dilator device is formed of a porous material, and more specifically of an open- or closed-cell sponge or foam. In a particular embodiment, insert portion 2702 is formed from a surgical sponge material such as cellulose or hydroxylated polyvinyl acetyl, for example.

The dilator device can optionally include one or more medicaments, lubricants, and/or therapeutic agents, such as, for example, anesthetics, vasoconstrictors, anti-inflammatories, pain relievers, saline, antibiotics, or any combination thereof for application to the surrounding tissue or gingival papilla. In one embodiment, the dilator device includes an anesthetic such as, for example, procaine, articaine, mepivicaine, or lidocaine, for local numbing of the treatment area. In another embodiment, the dilator device includes a vasoconstrictor such as, for example, phenylephrine, epinephrine, or norepinephrine, for achieving pharmaceutical compression of the gingival papilla. The medicaments can be applied to cover at least a portion of an outer surface of the dilator device, and/or incorporated within the dilator device, such as by absorption. For example, referring to FIG. 87B, a cross-sectional view of device 2700 is depicted. Device 2700 further comprises a coating 2706 on at least a portion of the outer surface of the dilator device 2700. In one embodiment, the dilator device includes a topical anesthetic (e.g. viscous lidocaine), topical vasoconstrictor, or combinations thereof. In other embodiments, the dilator device includes an anesthetic (e.g. procaine), vasoconstrictor, or combinations thereof absorbed therein. In an embodiment, one of a topical anesthetic and a topical vasoconstrictor is applied to an outer surface of the dilator device, while the other is contained within the dilator device, such as, by absorption.

The optional inclusion of such agents provides one or more benefits, including, but not limited to, application of one or more agents, such as topical anesthetic and/or vasoconstrictors, to highly focalized locations, application of one or more agents for an extended period of time, and minimal systemic absorption of applied agents.

Figure 88A:
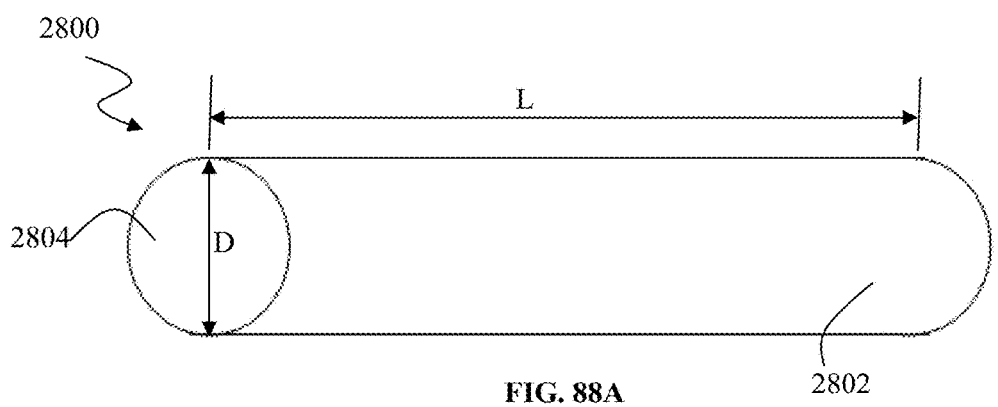
FIG. 88A is a side perspective view of a dilator device having a circular cross-section, according to another embodiment.

In another embodiment, and referring to FIG. 88A, dilator device 2800 comprises an elongate body or an insert portion 2802 presenting a longitudinal length L, and a circular cross-sectional profile 2804 presenting a diameter D. Device 2800 can be formed of the expandable materials described above, and can optionally include one or more medicaments, lubricants, and/or therapeutic agents as described above.

Figure 88B:
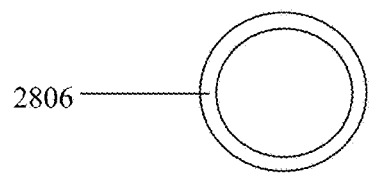
FIG. 88B is a cross-sectional view of the dilator device of FIG. 88A, according to an embodiment.

For example, referring to FIG. 88B, a cross-sectional view of an embodiment of device 2800 is depicted. Device 2800 further comprises a coating 2806 on at least a portion of the outer surface of the dilator device 2700.

Figure 88C:
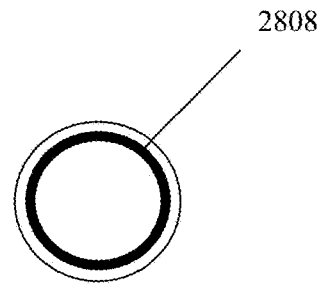
FIG. 88C is a cross-sectional view of the dilator device of FIG. 88A, according to an embodiment.

In another embodiment, referring to FIG. 88C, a cross-sectional view of an embodiment of device 2800 is depicted. Device 2800 further comprises a sponge 2808 incorporated within dilator device 2800, so that one or more medicaments, lubricants, and/or therapeutic agents can be integrated into sponge 2808, such as by absorption.

Figure 89:
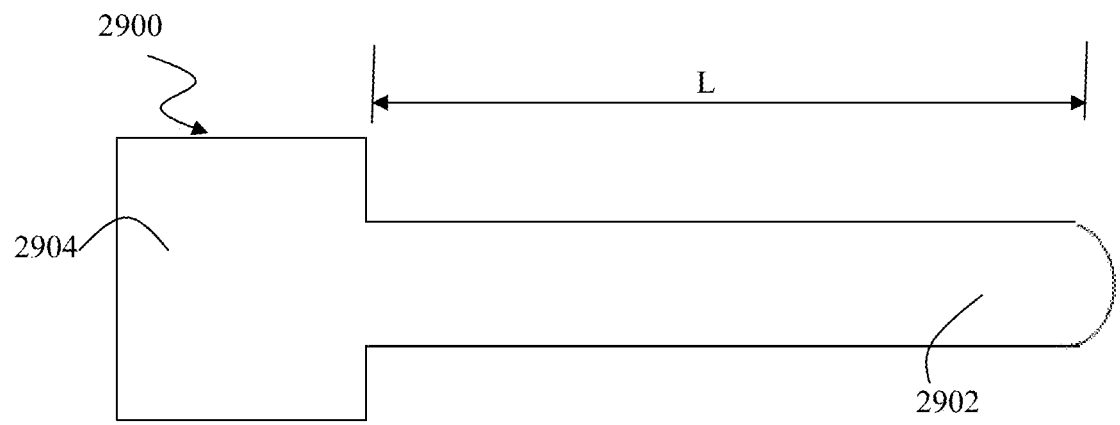
FIG. 89 is a side elevational view of a dilator device having a tab portion and an elongate insert portion, according to another embodiment.

In yet another embodiment, and referring to FIG. 89, dilator device 2900 comprises an insert portion 2902 presenting a longitudinal length L, and a tab portion 2904 for ease of manipulating insert portion 2902. Tab portion 2904 aids in the insertion, securement and/or removal of device 2900 within an interdental space. Insert portion 2902 can comprise any of a variety of cross-sectional profiles as described above, and can be formed of an expandable material as described above. Tab portion 2904 generally comprises a body of any of a variety of cross-sectional profiles, such as square, triangular, rectangular, or circular, and has a cross-sectional area that is greater than a cross-sectional area of insert portion 2902. Tab portion 2904 can be formed of the same expandable material as insert portion 2902 such that dilator device 2900 is monolithic, or alternatively, can be formed of a non-expandable material, such as a plastic or hard foam material, that imparts rigidity to device 2900. Insert portion 2902 can optionally be reinforced by a polymer material such as a floss-type material to impart rigidity.

Optionally, insert portion 2902 and/or tab portion 2904 can optionally include one or more medicaments, lubricants, and/or therapeutic agents as described above.

Figure 90:
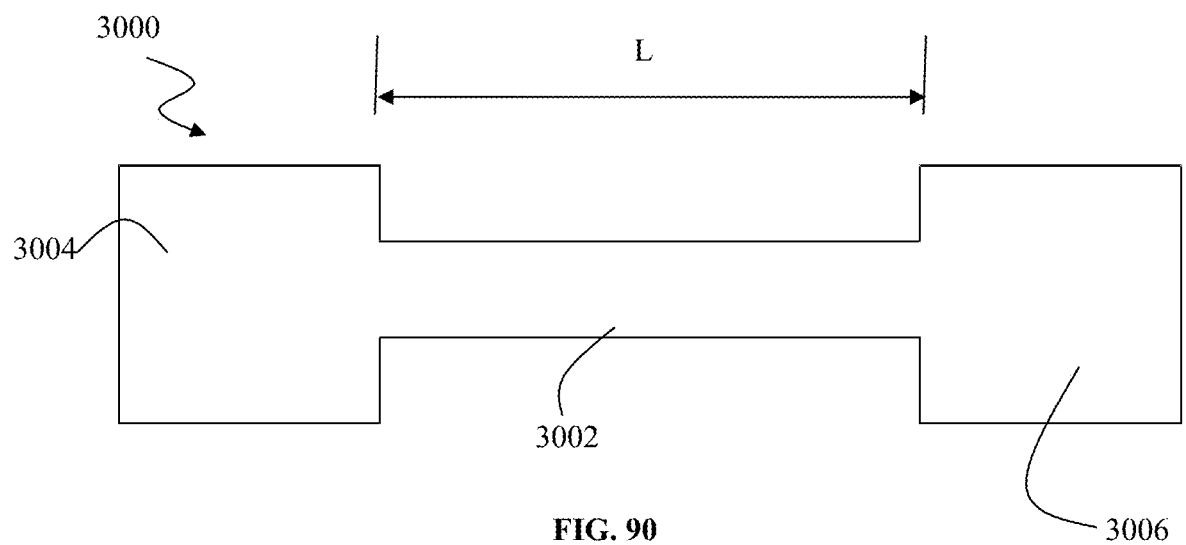
FIG. 90 is a side elevational view of a dilator device having a tab portion on each end of an elongate insert portion, according to another embodiment.

In another alternative embodiment, and referring to FIG. 90, dilator device 3000 comprises an elongate insert portion 3002 having a length L, a first tab portion 3004 coupled to a first end of insert portion 3002, and a second tab portion 3006 coupled to a second end of insert portion 3002. Insert portion 3002 can comprise any of a variety of cross-sectional profiles as described above, and can be formed of an expandable material as described above. First and second tab portions 3004, 3006 generally comprise a body having any of a variety of cross-sectional profiles, such as square, triangular, rectangular, or circular, and have a cross-sectional area that is greater than a cross-sectional area of insert portion 3002. First and second tab portions 3004, 3006 can be formed of the same expandable material as insert portion 3002 such that dilator device 3000 is monolithic, or alternatively, can be formed of a non-expandable material, such as a plastic or hard foam material, that imparts rigidity to device 3000.

In this embodiment, insert portion 3002 can optionally be reinforced by a polymer material such as a floss-type material to impart rigidity to insert portion 3002 between tabs 3004, 3006, such that device 3000 functions similar to a floss pick.

Optionally, insert portion 3002 and/or one or both of tab portions 3004, 3006 can optionally include one or more medicaments, lubricants, and/or therapeutic agents as described above.

In a particular embodiment relating to MMF procedures incorporating DO ties and/or TB ties, in a kit comprising a plurality of DO ties and/or TB ties and an assortment of dilator devices having various sizes, configurations, cross-sectional shapes, materials and other characteristics can be provided such that a medical professional could select the one or ones most suitable for any particular patient and his or her anatomy (e.g. adult vs. pediatric). For example, different cross-sectional shapes of the dilator device and/or DO ties and/or TB ties could be utilized to interact with the different interdental geometries of different teeth (e.g., molars, incisors, canines, etc). The kit can further include any of a variety of trimming tools, comfort caps, sizing devices, lip and cheek retractors, and/or required surgical or dental instruments for performing the procedures such as mirrors, surgical needles, threading devices, dental picks, instructions, or any combination thereof.

In embodiments, one or more medicaments are pre-applied to the dilator devices of the kits, and are activated by the addition of water. In another embodiment, one or more medicaments are separately packaged within the kit for application to the dilator device, such as by coating or soaking the device, prior to use of the dilator device.

Figure 91A:
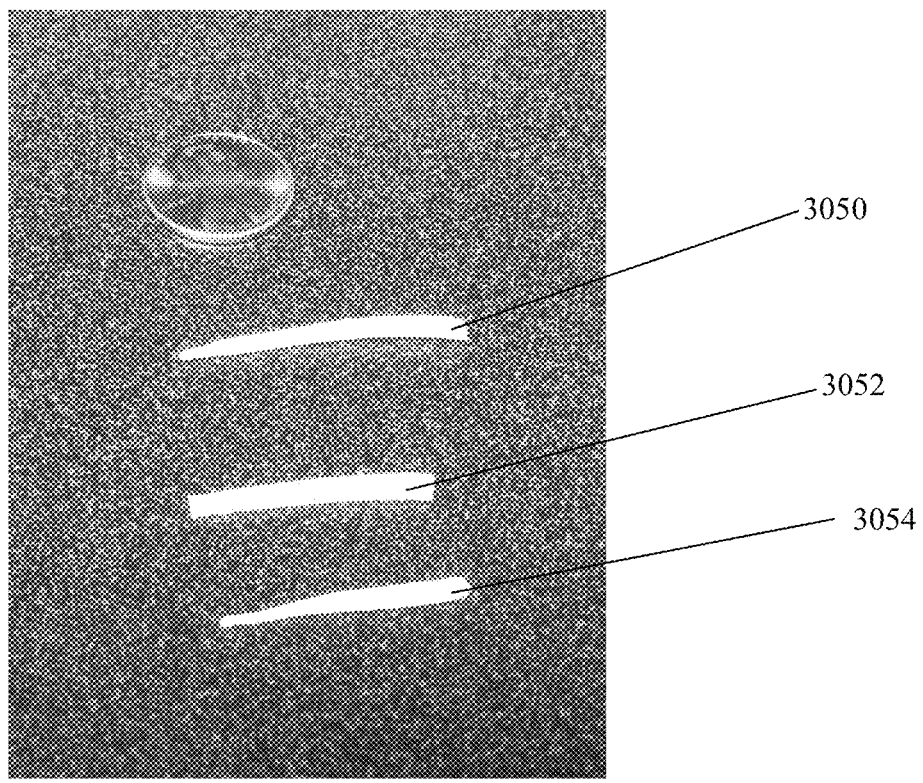
FIGS. 91A-91F are images depicting dilator devices in use, according to embodiments.
Figure 91B:
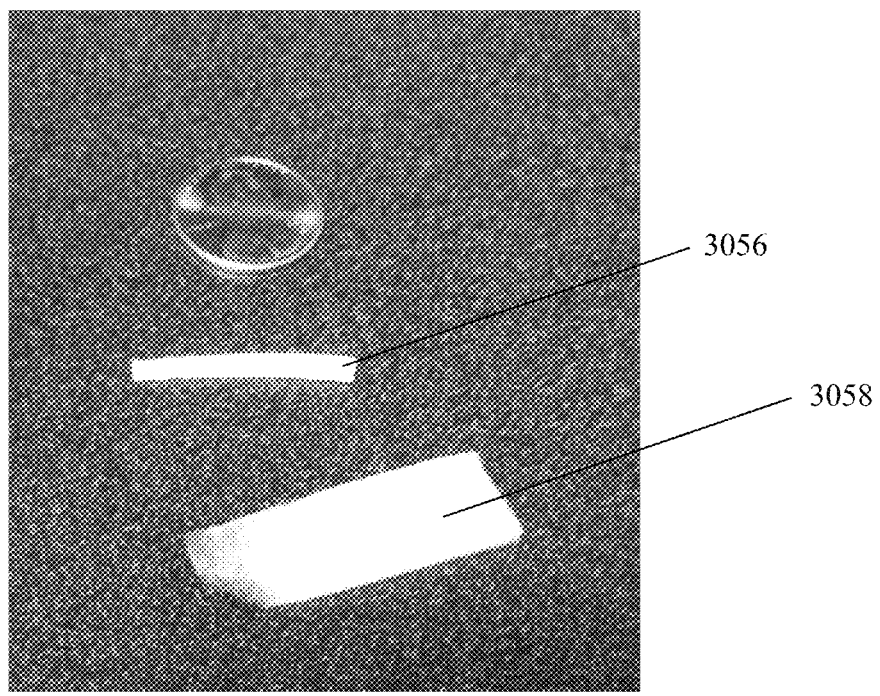

In embodiments, example expanding embrasure dilators are depicted in FIGS. 91A and 91B. For example, dilators 3050, 3052, 3054, and 3056 are illustrated. Expanded dilator 3058 is further depicted.

Figure 91C:
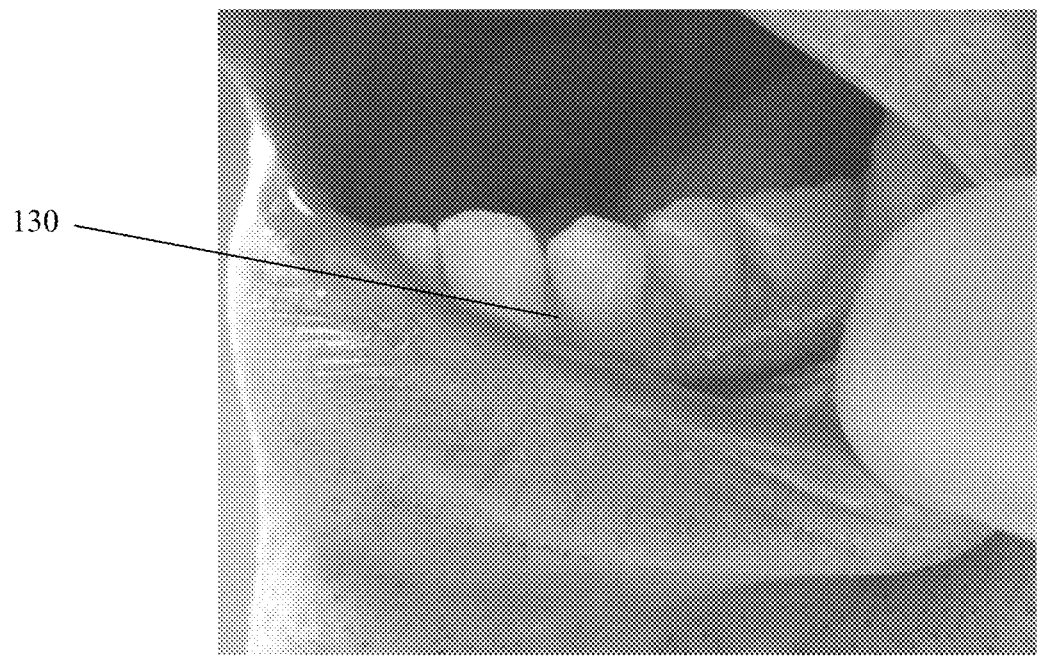
Figure 91D:
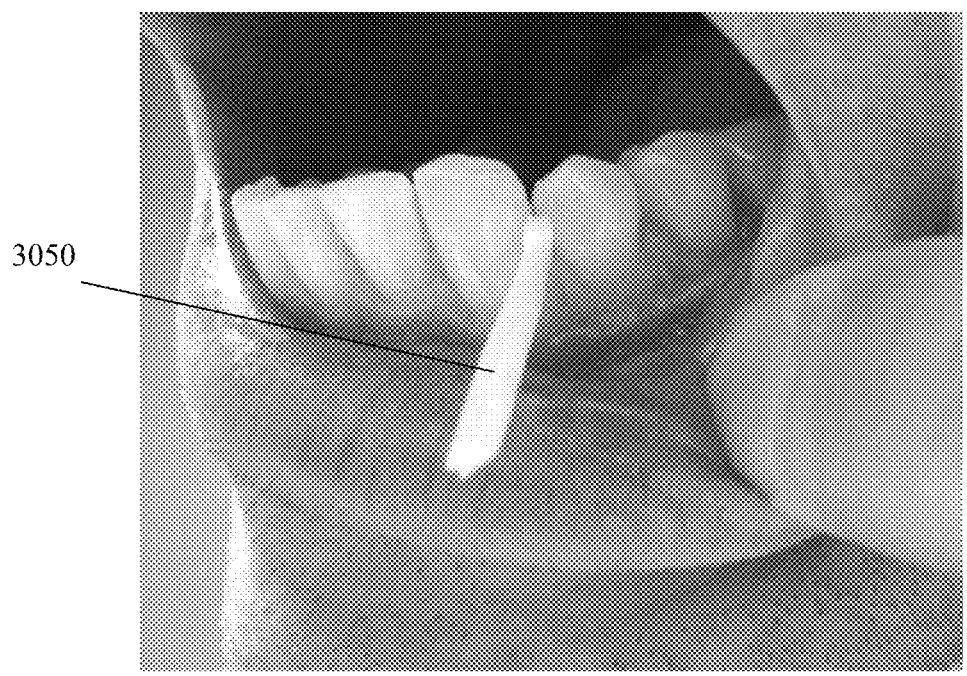
Figure 91E:
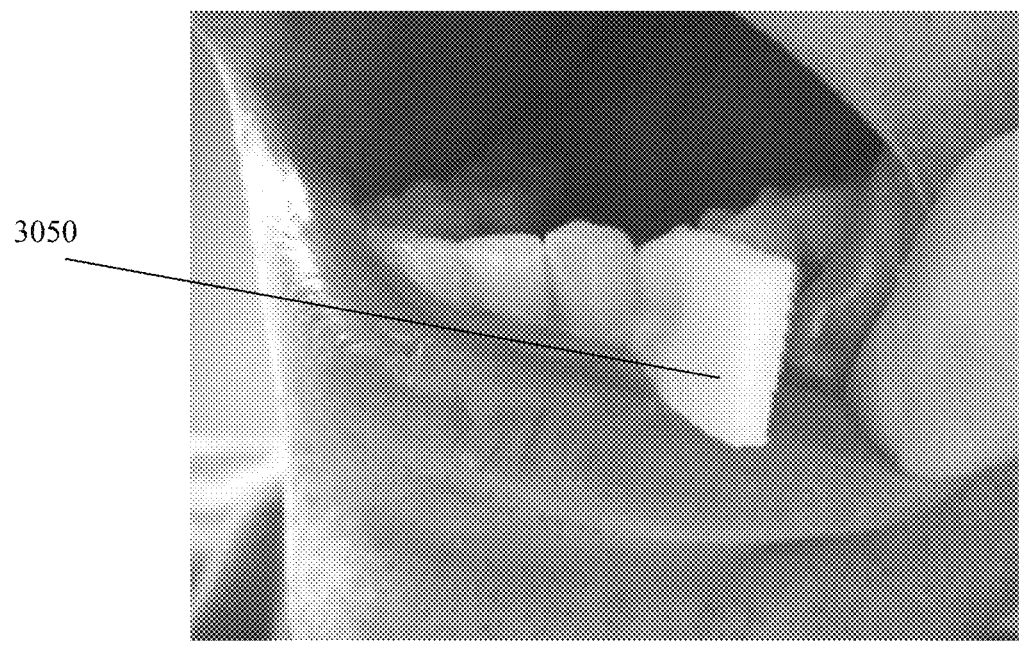

In use, a desired interdental space, such as an apical embrasure defined by two adjacent teeth, is identified and prepped by cleaning and/or drying. For example. FIG. 91C depicts a prepped (pre-dilated) apical embrasure 130. Optionally, a topical and/or injectable anesthetic and/or vasoconstrictor, is applied to the soft tissue or gingival papilla proximate or filling the embrasure. A dilator device is optionally pre-treated by the user and/or manufacturer with one or more medicaments, lubricants, and/or therapeutic agents as described above, such as by coating, dipping, or soaking the dilator device. The dilator device, in its compressed configuration, is then threaded or placed within the embrasure such that the elongate body of the dilator device extends through the embrasure and between the lingual and facial (buccal) surfaces of the adjacent teeth defining the embrasure. For example, referring to FIG. 91D, embrasure 130 undergoing mechanical dilation is depicted. For ease of illustration, FIGS. 91D-91E are depicted with dilator 3050. However, any of the aforementioned dilators can be utilized.

Water or an aqueous solution is applied to the dilator device until the dilator device expands into the expanded configuration, thereby physically dilating the embrasure area by compression of the soft tissue or gingival papilla, while minimizing trauma to the soft tissue. Optional medicaments not previously applied to the dilator device can be applied previously to, simultaneously with, and/or subsequently with the water or aqueous solution. For example, referring to FIG. 91E, embrasure 130 undergoing mechanical and medicinal dilation utilizing dilator 3050, as well as application with a topical anesthetic. In embodiments, medicinal dilation comprises 1% phenylephrine. In embodiments, a topical anesthetic comprises 4% lidocaine. In one embodiment, the dilator device is treated with a topical vasoconstrictor which pharmaceutically compresses the gingival papilla thereby dilating the embrasure.

Figure 91F:
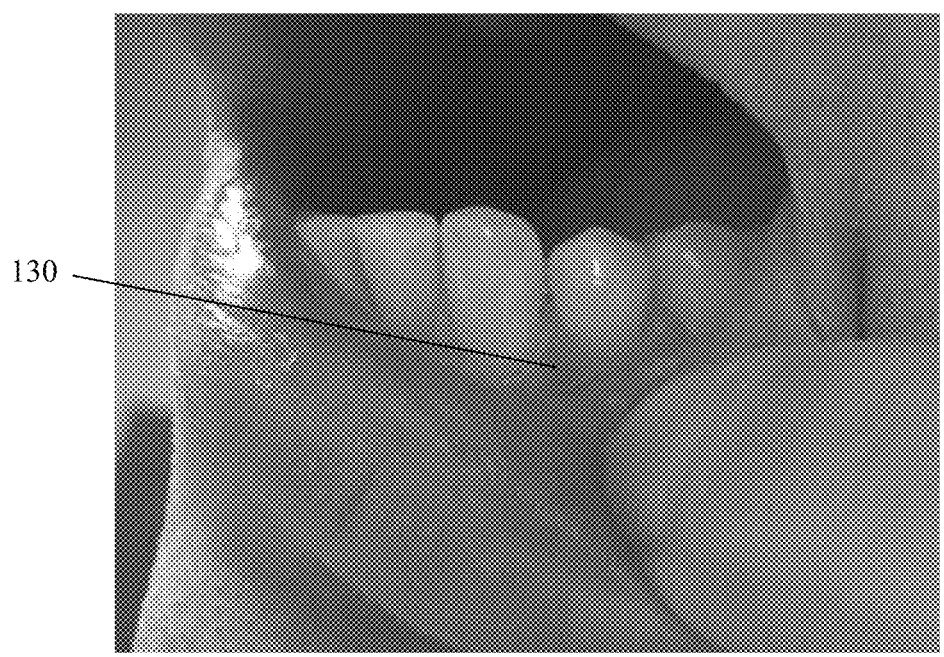

Once sufficient dilation of the embrasure area is complete, the dilator device is removed. For example, referring to FIG. 91F, embrasure 130 is depicted with dilator device 3050 removed. The dark, thin triangle between teeth below their contact point can be compared to, for example, embrasure 130 in FIG. 91C. A desired procedure can be performed such as, but not limited to, MMF procedures, maxillomandibular advancements, orthognathic surgery, and temporomandibular joint replacements. In one non-limiting embodiment relating to MMF procedures incorporating DO ties and/or TB ties, the appropriate tie is threaded through the embrasure. Upon placement of all desired ties, the ties are secured to accomplish dental occlusion and/or tensioning for MMF.

In any of the above embodiments, one or more ends of the insert portion and/or tab portion (if present) can include an attachment device, such as a loop, handle, eyehook, or other such structure in which DO tie and/or TB tie, or other device, can be coupled thereto either before insertion, or while the dilator device is inserted within the interdental space. In use, the insert portion is inserted into the interdental space such that the attachment device is located proximate the lingual surfaces of the teeth. Once the soft tissue is sufficiently dilated, the device is withdrawn from the space by pulling the device towards the facial (buccal) surface of the teeth, thereby threading the tie within the space. Once the device is free from the space, the tie is decoupled from the device such that the tie remains threaded within the space.

Sizing Interdental Spaces

Embodiments relate to embrasure sizing devices, systems, methods of sizing embrasures for achieving MMF. In an embodiment, a sizing device can comprise a tapering probe optionally coupled to an elongate rigid rod portion having a handle at one end. A cross-sectional profile of the probe can be circular, triangular, trapezoidal, or any of a variety of shapes. The tapering probe has a plurality of graduations or markings along its length, corresponding to a depth of insertion of the probe, which is then correlated to a width of the embrasure. The markings can be any of a variety of indicators including numbers, colors, tabs, notches, hashes, or other indicators of size.

In use, the probe is inserted into and threaded through the interdental space, such as an apical embrasure, until it cannot be inserted further. The last visible marking before the embrasure, i.e. the innermost marking that is not inserted into the embrasure, is recorded. The marking correlates to a size or width of the embrasure such that an appropriately sized tie can be selected for threading within the embrasure to minimize soft tissue injury while maximizing MMF.

In one embodiment, the markings of the sizing probe comprise a plurality of color bands. The color of each marking is unique to other markings, and is the same color of a tie corresponding to an appropriately-sized tie. A system or kit can include such sizing probe and a plurality of color-coded tension band ties and/or occlusion band ties.

In another embodiment, the markings of the sizing probe comprise a numbering system. Each number corresponds to an appropriately-sized tie labeled with the same number. A system or kit can include such sizing probe and a plurality of numbered tension band ties and/or occlusion band ties.

The sizing device can optionally include one or more medicaments, lubricants, and/or therapeutic agents, such as, for example, anesthetics, vasoconstrictors, anti-inflammatories, pain relievers, antibiotics, or any combination thereof for application to the surrounding tissue or gingival papilla. In one embodiment, the sizing device includes a topical anesthetic, topical vasoconstrictor, or combinations thereof. The medicaments can be applied to cover at least a portion of an outer surface of the sizing device, and/or incorporated within the sizing device.

In an embodiment, a system or kit can comprise materials and/or tools for performing MMF techniques. For example, the system or kit can comprise one or more embrasure sizing devices, and any of a combination of a plurality of dental occlusion ties and/or tension band ties (referred to herein as "DO ties" and "TB ties," respectively), trimming tools, comfort caps, dilator devices, lip and cheek retractors, and/or required surgical or dental instruments for performing the procedures such as mirrors, surgical needles, threading devices, dental picks, instructions, or any combination thereof. In an embodiment, the embrasure sizing device and ties are color coded. In another embodiment, the embrasure sizing device and ties incorporate a numbering system.

Embrasure sizing devices according to embodiments are generally utilized to measure or size an interdental space, such as an apical embrasure. Referring again to FIG. 5, sizing devices according to embodiments function to measure embrasure 130 by physically and optionally pharmaceutically compress gingival papilla 132 to provide sufficient access to thread the tie therethrough.

Figure 92:
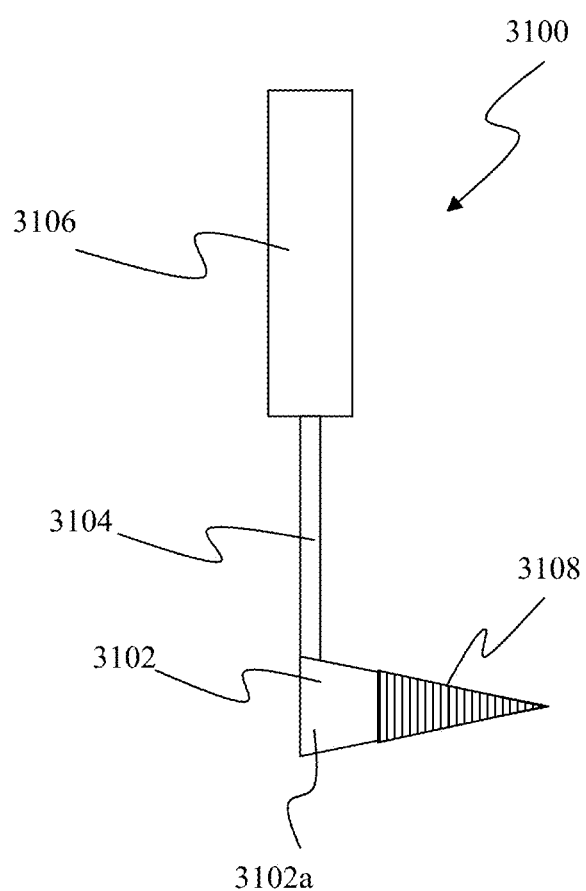
FIG. 92 is a side view of a tapered sizing device, according to an embodiment.

Referring to an embodiment depicted in FIG. 92, interdental sizing device 3100 generally includes a probe 3102 comprising a tapered conical portion formed of a plastic or foam material for at least partial insertion within an interdental space, such as an apical embrasure. A cross-sectional profile can comprise a circle, triangle, trapezoid, square, or any of a variety of shapes. A length of the tapered conical probe can range from about 0.5 cm to about 3.0 cm, and more particularly from about 1 cm to about 2 cm, in embodiments. A plurality of graduated markers or size indicators 3108 can be formed along the length. Each marker can be indicative of a size of the embrasure into which it is placed so that an appropriately sized tension band tie or occlusion tie can be selected for the embrasure, thereby minimizing soft tissue injury and discomfort, while maximizing MMF.

Probe 3102 can be optionally coupled to an elongate rigid rod portion 3104 at an untapered or wide end 3102a of probe 3102. In this embodiment, probe 3102 is coupled to rod portion 3104 such that the length of probe 3102 is substantially perpendicular to the length of rod portion 3104. An ergonomic handle 3106 is optionally coupled to an opposite end of rod portion 3104 from probe 3102. In alternative embodiments, probe 3102 can be coupled to rod portion 3104 at an angle, or can be collinear with rod portion 3104.

In an alternative embodiment not shown, the sizing device includes two probe portions collinearly and oppositely arranged. In this embodiment, the second probe portion can also comprise a plurality of graduated markings such that either end of the sizing device can be used to measure interdental spaces or can include other tools, such as a toothpick having a plurality of radially-extending spines from the surface of the second probe portion.

Plurality of markings 3108 are positioned to probe 3102 to correspond to a width of the embrasure. Markings 3108 can be any of a variety of indicators including numbers, colors, hashes, raised portions, or other indicators of size.

Figure 93:
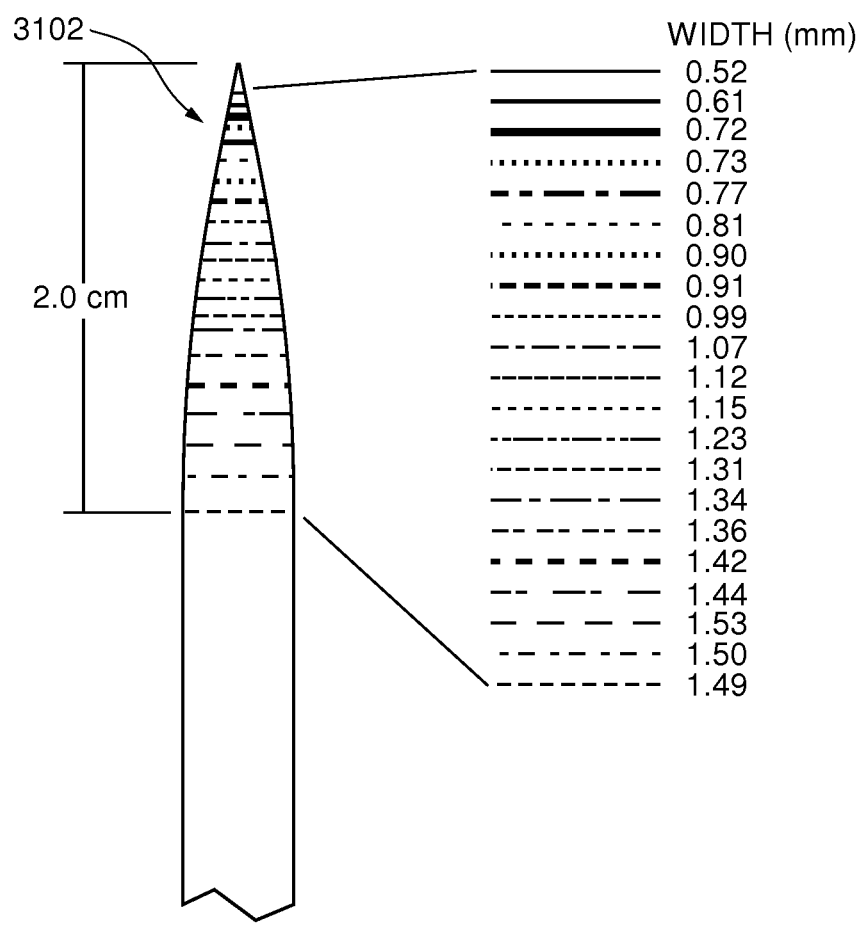
FIG. 93 is a close up of a color-coded tapered sizing probe, according to an embodiment.

Referring to FIG. 93, in one embodiment, markings 3108 comprise a plurality of color bands. The color of each band is the same color of a tie corresponding to an appropriately-sized tie. In this embodiment, the color bands are discrete lines separated by a gap. In an alternative embodiment, the color bands are adjacent to one another such that when probe 3102 is inserted as much as possible, the size of the tie used for the embrasure is determined by which band probe 3102 stops within.

In another embodiment not shown, markers 3108 comprise a plurality of numbers either indicative of the actual size of the embrasure (such as a width), or a numbering system that correlates with appropriately-sized tie labeled with the same number.

In embodiments, markers 3108 can include any number of markings indicative of any range of sizes. For examples, each marking can indicate 0.01 mm to 0.1 mm difference in size from adjacent marking. The tables below are non-limiting examples of sizing systems in which the depth of insertion of the probe is used to link to a marking on the probe to estimate the width of the embrasure:

TABLE 1

Marking system #1

| Marking number | Embrasure width (mm) |
|---|---|
| 1 | 1.59 |
| 2 | 1.53 |
| 3 | 1.50 |
| 4 | 1.44 |
| 5 | 1.42 |
| 6 | 1.36 |
| 7 | 1.34 |
| 8 | 1.31 |
| 9 | 1.23 |
| 10 | 1.15 |
| 11 | 1.12 |
| 12 | 1.07 |
| 13 | 0.99 |
| 14 | 0.91 |
| 15 | 0.90 |
| 16 | 0.81 |
| 17 | 0.77 |
| 18 | 0.73 |
| 19 | 0.72 |
| 20 | 0.61 |
| 21 | 0.52 |

TABLE 2

Marking system #2

| Marking number | Embrasure width (mm) |
|---|---|
| 1 | 1.60 |
| 2 | 1.57 |
| 3 | 1.55 |
| 4 | 1.54 |
| 5 | 1.48 |
| 6 | 1.40 |
| 7 | 1.37 |
| 8 | 1.30 |
| 9 | 1.27 |
| 10 | 1.17 |
| 11 | 1.13 |
| 12 | 1.07 |
| 13 | 1.03 |
| 14 | 0.95 |
| 15 | 0.88 |
| 16 | 0.83 |
| 17 | 0.75 |
| 18 | 0.65 |
| 19 | 0.52 |

The data for Tables 1 and 2 were collected from cadaver studies of various apical embrasures.

Figure 94B:
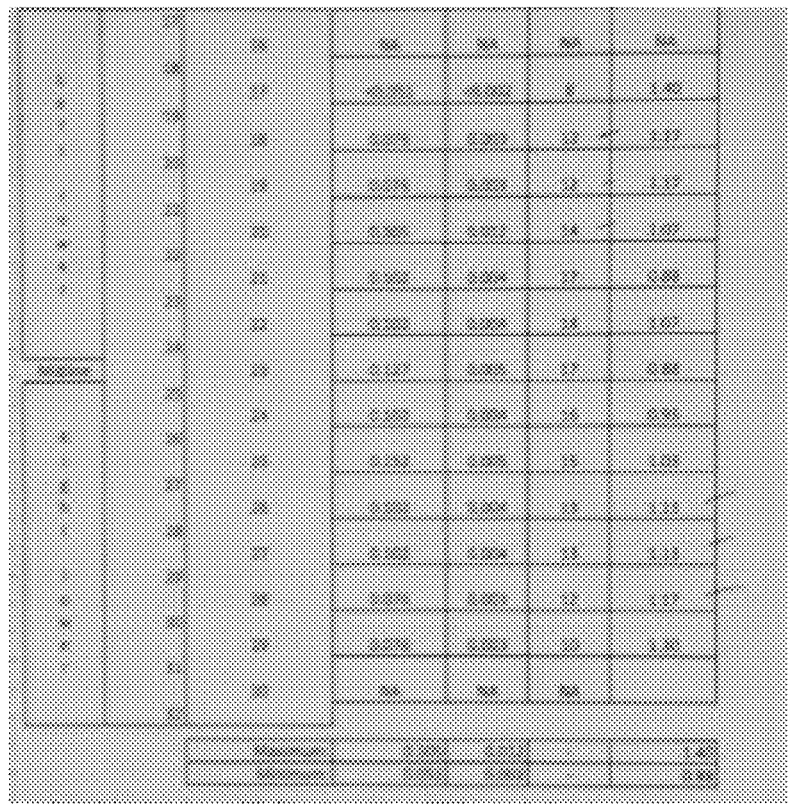

Referring to FIGS. 94A and 94B, the results of human pilot sizing studies are shown, correlating feeler gauge measurements and embrasure sizing device measurements. While the sizing device measurements represent the width of the embrasure, the feeler gauge measurements represent a measure of the "floss out" dimension between adjacent teeth for determining a minimum width of a tie for a particular embrasure; in other words, this is $1/1000^{th}$ of an inch more than the maximum width that can pass between contact regions of two adjacent teeth, similar to a strand of floss. The feeler gauge measurements are determined by insertion of a feeler gauge having $1/1000^{th}$ of an inch increasing widths. The width is increased until the gauge no longer can slide or pass between adjacent teeth.

According to embodiments, a system or kit can include one or more sizing probes with a marking system, such as a color-coded or number system, and a plurality of coded tension band ties and/or occlusion band ties, coded to correspond with the marking of the sizing probes.

Device 3100 is shaped to effectively wedge between two adjacent teeth in the apical embrasure 130 (refer, for example, to FIG. 5) while minimally disrupting the gingival papilla 132. In this embodiment, a cross-sectional profile 3104 of insert portion 3102 can comprise an approximate or general isosceles triangle presenting two equal sides A, and a base B. Base B can be sized according to a space between adjacent teeth, and can be, for example, in a range from about 0.25 mm to about 1 mm, and more particularly about 0.66 mm. In an alternative embodiment not shown, the cross-sectional profile comprises an equilateral triangle. Any of a variety of other cross-sectional shapes and configurations can be used in other embodiments, some of which are described below. The edges or corners of device 3110, in this and other embodiments, can be curved, flat, regular or irregular, square, chamfered, or have some other shape or configuration that aids in insertion, positioning and/or dilation. The kit can further include any of a variety of trimming tools, comfort caps, dilator devices, lip and cheek retractors, and/or required surgical or dental instruments for performing the procedures such as mirrors, surgical needles, threading devices, dental picks, instructions, or any combination thereof.

Figure 95:
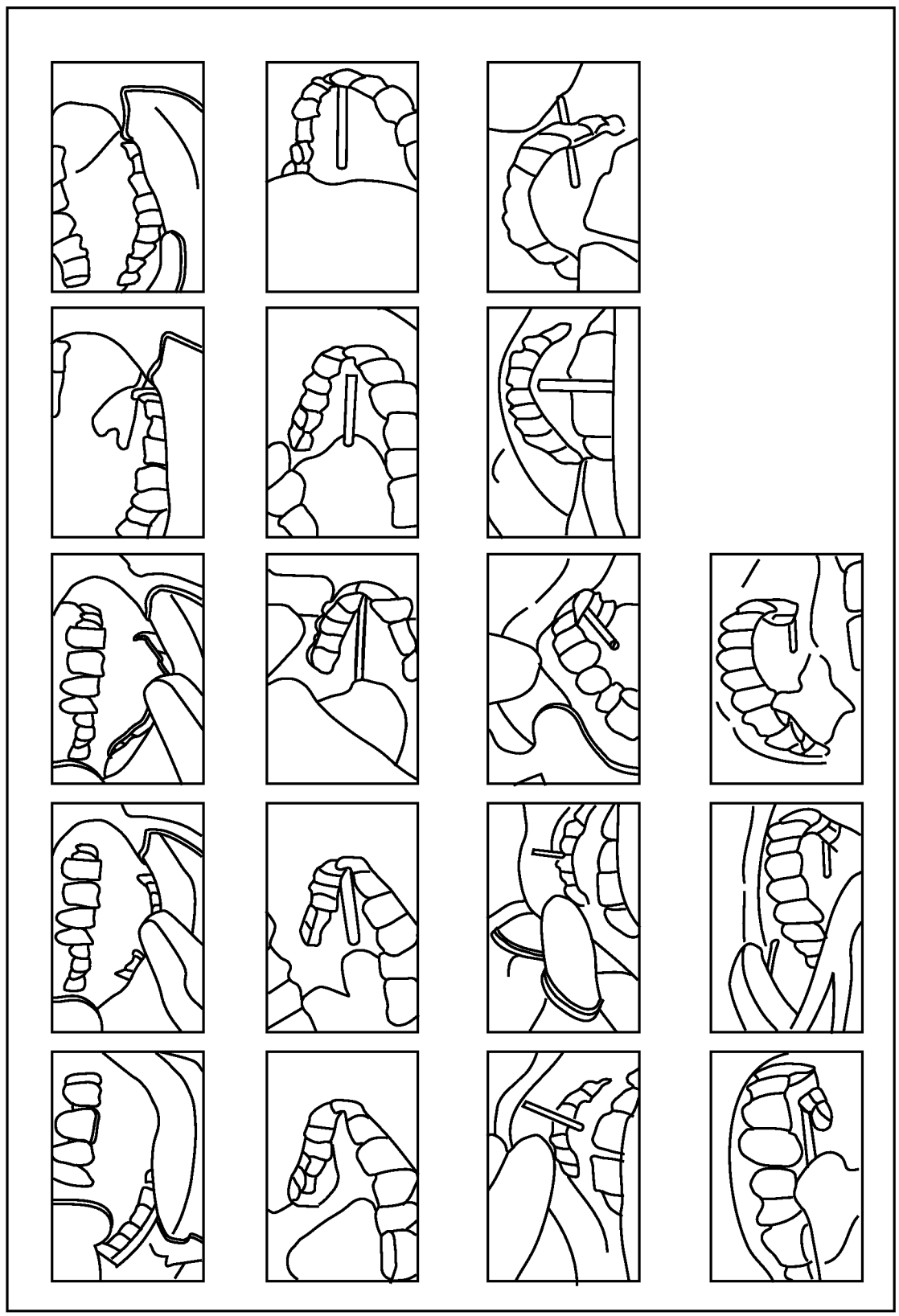
FIG. 95 is a series of images depicting a sizing device being used to measure different apical embrasures, according to an embodiment.

In use, and referring to FIG. 95, a desired interdental space, such as an apical embrasure defined by two adjacent teeth, is identified and prepped by cleaning and/or drying. Optionally, a topical and/or injectable anesthetic is applied to the soft tissue or gingival papilla proximate or filling the embrasure. The probe portion of the sizing device is optionally pre-treated by the user and/or manufacturer with one or more medicaments, lubricants, and/or therapeutic agents as described above, such as by coating, dipping, or soaking the probe portion. The tapered end of the probe portion of the sizing device is then inserted within and through the embrasure from either the lingual and facial surfaces of the adjacent teeth defining the embrasure or vice versa. The probe portion is inserted until resistance is felt. The innermost marking that has not entered the embrasure, indicating the depth of the insertion, is recorded, charted, and/or photographed, and removed. The selected marking is then matched to an appropriately sized tie for threading within and through the embrasure. Upon placement of the desired ties, the ties are secured to accomplish dental occlusion and/or tensioning.

The sizing devices according to embodiments allow for efficient sizing of interdental spaces, and particularly apical embrasures, by making sizing decisions simple and universal, with minimal discomfort to the patient. This technology can be designed to be directly linked to appropriately sized tension band ties and/or occlusion ties used for MMF. However, one of ordinary skill in the art would recognize that the devices are not limited for use in MMF procedures, and can be used for any of a variety of dental applications such as, for example, apical embrasure sizing for periodontists, oral maxillofacial surgeons, and other practitioners.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A unitary device for achieving maxillo-mandibular fixation, the device comprising:
   a first end comprising an insertion portion;
   a second end comprising a clasp, the clasp including a metallic locking mechanism and a polymeric housing at least partially encapsulating the metallic locking mechanism, the polymeric housing defining a pass-through void with a cylindrical input aperture, wherein the metallic locking mechanism is arranged entirely within the polymeric housing and defines at least one resilient tab extending radially into the pass-through void; and
   an elongate body coupled to the clasp and the insertion portion, the elongate body having a circular cross-section and a smooth and continuous outer surface extending from the polymeric housing of the clasp to the insertion portion and configured to be received in the pass-through void and to be locked by the at least one resilient tab of the metallic locking mechanism of the clasp at the smooth and continuous outer surface to form a loop configured to extend between first and second interdental spaces and capable of non-segmental tightening adjustments to have sufficient force to achieve maxillo-mandibular fixation, wherein the insertion portion, the elongate body, and the clasp are coupled to form a single continuous device from the insertion portion at the first end to the clasp at the second end.

2. The device of claim 1, wherein the first interdental space is on the upper jaw and the second interdental space is on the lower jaw.

3. The device of claim 1, wherein the first and second interdental spaces are both on the same one of the upper jaw or the lower jaw.

4. The device of claim 1, further comprising a cover portion configured to be removably coupled to the clasp.

5. The device of claim 1, wherein the circular cross-section is sized to facilitate placement within an interdental space.

6. The device of claim 1, wherein the housing comprises additional material proximate the tab to provide additional support to secure the thread portion within the first aperture.

7. The device of claim 1, further comprising a coupling mechanism configured to allow the device to be coupled to another device.

\* \* \* \* \*